(12) United States Patent
Valamehr et al.

(10) Patent No.: US 12,247,226 B2
(45) Date of Patent: Mar. 11, 2025

(54) CELLULAR REPROGRAMMING USING TEMPORAL AND TRANSIENT PLASMID VECTOR EXPRESSION SYSTEM

(71) Applicant: FATE THERAPEUTICS, INC., San Diego, CA (US)

(72) Inventors: Bahram Valamehr, San Diego, CA (US); Megan Robinson, San Diego, CA (US)

(73) Assignee: FATE THERAPEUTICS, INC., San Diego, CA (US)

( * ) Notice: Subject to any disclaimer, the term of this patent is extended or adjusted under 35 U.S.C. 154(b) by 858 days.

(21) Appl. No.: 16/649,084

(22) PCT Filed: Oct. 10, 2018

(86) PCT No.: PCT/US2018/055208
§ 371 (c)(1),
(2) Date: Mar. 19, 2020

(87) PCT Pub. No.: WO2019/075057
PCT Pub. Date: Apr. 18, 2019

(65) Prior Publication Data
US 2020/0270581 A1 Aug. 27, 2020

Related U.S. Application Data

(60) Provisional application No. 62/571,105, filed on Oct. 11, 2017.

(51) Int. Cl.
*C12N 5/074* (2010.01)
*A61K 35/12* (2015.01)
*C12N 15/85* (2006.01)

(52) U.S. Cl.
CPC ............ *C12N 5/0696* (2013.01); *A61K 35/12* (2013.01); *C12N 15/85* (2013.01); *C12N 2800/10* (2013.01)

(58) Field of Classification Search
CPC ....... C12N 5/0696; C12N 15/85; A61K 35/12
USPC .......................................... 424/93.21, 200.1
See application file for complete search history.

(56) References Cited

U.S. PATENT DOCUMENTS

| | | | |
|---|---|---|---|
| 6,352,694 B1 | 3/2002 | June et al. | |
| 8,546,140 B2 | 10/2013 | Mack et al. | |
| 2004/0101519 A1 | 5/2004 | June et al. | |
| 2006/0034810 A1 | 2/2006 | Riley et al. | |
| 2011/0104125 A1 | 5/2011 | Yu | |
| 2015/0175973 A1 | 6/2015 | Yamanaka et al. | |
| 2017/0073643 A1 | 3/2017 | Valamehr et al. | |
| 2017/0226483 A1* | 8/2017 | Abraham | C12Y 207/01021 |

FOREIGN PATENT DOCUMENTS

| | | |
|---|---|---|
| WO | WO 2012/018933 A2 | 2/2012 |
| WO | WO-2012/087965 A2 | 6/2012 |
| WO | WO-2012/087965 A3 | 6/2012 |
| WO | WO-2015/134652 A1 | 9/2015 |
| WO | WO-2017/066634 A1 | 4/2017 |
| WO | WO-2017/078807 A1 | 5/2017 |
| WO | WO 2017/123789 A1 | 7/2017 |

OTHER PUBLICATIONS

Yu, J., Chau, K. F., Vodyanik, M. A., Jiang, J., & Jiang, Y. (2011). Efficient feeder-free episomal reprogramming with small molecules. PLoS one, 6(3), e17557 (Year: 2011).*
Kaneda, Y., Saeki, Y., Nakabayashi, M., Zhou, W. Z., Kaneda, M. W., & Morishita, R. (2000). Enhancement of transgene expression by cotransfection of oriP plasmid with EBNA-1 expression vector. Human gene therapy, 11(3), 471-479. (Year: 2000).*
Malik, N., & Rao, M. S. (2013). A review of the methods for human iPSC derivation. Pluripotent stem cells, 23-33. (Year: 2013).*
Sipos, F., & Galamb, O. (2012). Epithelial-to-mesenchymal and mesenchymal-to-epithelial transitions in the colon. World journal of gastroenterology: WJG, 18(7), 601. (Year: 2012).*
Adan, A., Alizada, G., Kiraz, Y., Baran, Y., & Nalbant, A. (2016). Flow cytometry: basic principles and applications. Critical reviews in biotechnology, 37(2), 163-176. (Year: 2016).*
Jung et al,. "ONSL and OSKM cocktails act synergistically in reprogramming human somatic cells into induced pluripotent stem cells". Molecular Human Reproduction. vol. 20, Issue 6, Jun. 2014, pp. 538-549) (Year: 2014).*
Mack et al., "Generation of induced pluripotent stem cells from CD34+ cells across blood drawn from multiple donors with non-integrating episomal vectors," *PLoS One*, 6(11):e27956 (2011).
Valamehr et al. (Mar. 11, 2014). "Platform for induction and maintenance of transgene-free hiPSCs resembling ground state pluripotent stem cells," *Stem Cell Reports*, 2(3):366-381.
Ban, H. et al. (Aug. 23, 2011). "Efficient generation of transgene-free human induced pluripotent stem cells (iPSCs) by temperature-sensitive Sendai virus vectors," *PNAS* 108(34):14234-14239.
Brambrink, T. et al. (Feb. 7, 2008). "Sequential expression of pluripotency markers during direct reprogramming of mouse somatic cells," *Cell Stem Cell* 2(2):151-159.

(Continued)

*Primary Examiner* — Allison M Fox
*Assistant Examiner* — Hanan Isam Abuzeineh
(74) *Attorney, Agent, or Firm* — Greenberg Traurig, LLP

(57) ABSTRACT

Provided are methods and compositions for inducing the reprogramming of a non-pluripotent to an iPSC having desirable properties using a vector system providing transient and temporal expression of transgenes that are short-lived. Also provided are reprogramming cells and iPSC populations or clonal cell lines using the provided reprogramming methods and compositions. Further provided are genome-engineered iPSCs and derived cells redifferentiated therefrom to comprise targeted editing involving insertions and deletions in one or more selected genomic loci.

39 Claims, 10 Drawing Sheets
Specification includes a Sequence Listing.

(56) References Cited

OTHER PUBLICATIONS

Cheng, L. et al. (Mar. 2, 2012). "Low incidence of DNA sequence variation in human induced pluripotent stem cells generated by nonintegrating plasmid expression," *Cell Stem Cell* 10(3):337-344.
Drozd, A.M. et al. (Jun. 19, 2015). "Generation of human iPSCs from cells of fibroblastic and epithelial origin by means of the oriP/EBNA-1 episomal reprogramming system," *Stem Cell Research* 6(1):122).
Fusaki, N. et al. (2009). "Efficient induction of transgene-free human pluripotent stem cells using a vector based on Sendai virus, an RNA virus that does not integrate into the host genome," *Proc Jpn Acad Ser B Phys Biol Sci* 85(8):348-362.
Gil, J.S. et al. (Oct. 2010, e-published May 13, 2010). "Delivery of an EBV episome by a self-circularizing helper-dependent adenovirus: long-term transgene expression in immunocompetent mice," *Gene Ther* 17(10):1288-1293.
Howden, S.E et al. (Aug. 2006). "Chromatin-binding regions of EBNA1 protein facilitate the enhanced transfection of Epstein-Barr virus-based vectors," *Human Gene Therapy* 17(8):833-844.
International Search Report mailed on Feb. 8, 2019, for PCT Application No. PCT/US2018/055208, filed Oct. 10, 2018, 4 pages.
Kaneda, Y. et al. (Feb. 10, 2000). "Enhancement of transgene expression by cotransfection of oriP plasmid with EBNA-1 expression vector," *Human Gene Therapy* 11(3):471-479.
Leight, E.R. et al. (Jul. 2001). "Establishment of an oriP replicon is dependent upon an infrequent, epigenetic event," *Mol Cell Biol* 21(13):4149-4161.
Malik, N. et al. (2013). "A review of the methods for human iPSC derivation," *Methods Mol Biol* 997:23-33.
Mazda, O. et al. (May 26, 1997). "Extremely efficient gene transfection into lympho- hematopoietic cell lines by Epstein-Barr virus-based vectors," *J. Immunol. Methods* 204(2):143-151.
Miller, J.D. et al. (Dec. 5, 2013). "Human iPSC-based modeling of late-onset disease via progerin-induced aging," *Cell Stem Cell.* 13(6):691-705.
Narsinh, K.H. et al. (Jan. 2011, e-published Dec. 23, 2010). "Generation of adult human induced pluripotent stem cells using nonviral minicircle DNA vectors," *Nat Protoc* 6(1):78-88.
Nishimura, T. et al. (Jan. 3, 2013). "Generation of rejuvenated antigen-specific T cells by reprogramming to pluripotency and redifferentiation," *Cell Stem Cell* 12(1):114-126.
Okita, K. et al. ((Nov. 7, 2008, e-published Oct. 9, 2008). "Generation of mouse induced pluripotent stem cells without viral vectors," *Science* 322(5903):949-953.
Qian, J. et al. (Sep. 2001). "Development of a K562 cell-based assay for screening anticancer agents," *Acta Pharmacol Sin.* 22(9):821-826.
Seki, T. et al. (Jul. 2, 2010). "Generation of induced pluripotent stem cells from human terminally differentiated circulating T cells," *Cell Stem Cell* 7(1):11-14.
Stadtfeld, M. et al. (Mar. 6, 2008, e-published Feb. 14, 2008). "Defining molecular cornerstones during fibroblast to iPS cell reprogramming in mouse," *Cell Stem Cell* 2(3):230-240.
Stadtfeld, M. et al. (Nov. 7, 2008, e-published Sep. 25, 2008). "Induced pluripotent stem cells generated without viral integration," *Science* 322(5903):945-949.
Stockwell, B.R. et al. (Feb. 1999). "High-throughput screening of small molecules in miniaturized mammalian cell-based assays involving post-translational modifications," *Chem Biol.* 6(2):71-83.
Sugden, B. et al. (Feb. 1985). "A vector that replicates as a plasmid and can be efficiently selected in B-lymphocytes transformed by Epstein-Barr virus," *Mol. Cell. Biol.* 5(2):410-413.
Warren, L. et al. (Nov. 5, 2010, Sep. 30, 2010). "Highly efficient reprogramming to pluripotency and directed differentiation of human cells using synthetic modified mRNA," *Cell Stem Cell* 7 (5):618-630.
Wen, W. et al. (Jun. 14, 2016, e-published May 5, 2016). "Enhanced Generation of Integration-free iPSCs from Human Adult Peripheral Blood Mononuclear Cells with an Optimal Combination of Episomal Vectors," *Stem Cell Reports* 6(6):873-884.
Written Opinion mailed on Feb. 8, 2019, for PCT Application No. PCT/US2018/055208, filed Oct. 10, 2018, 10 pages.
Yates, J.L. et al. (Feb. 28-Mar. 6, 1985). "Stable replication of plasmids derived from Epstein-Barr virus in various mammalian cells," *Nature* 313(6005):812-815.
Yu, J. et al. (May 8, 2009, e-published Mar. 26, 2009). "Human induced pluripotent stem cells free of vector and transgene sequences," *Science* 324(5928):797-801.
Zhou, H. et al. (May 2009, e-published Apr. 23, 2009). "Generation of induced pluripotent stem cells using recombinant proteins," *Cell Stem Cell* 4(5):381-384.
Zhou, W. et al. (Nov. 2009). "Adenoviral gene delivery can reprogram human fibroblasts to induced pluripotent stem cells," *Stem Cells* 27(11):2667-2674.

\* cited by examiner

| Vector | Vector Description |
|---|---|
| 1A | pCEP4-OCT4-P2A-OCT4-OriP |
| 1B | pCEP4-NANOG-P2A-SOX2-T2A-SV40 Large T-OriP |
| 2 | pCDNA – EBNA-1 |
| 3 | pCEP4-OriP – EBNA-1 |

CELLULAR REPROGRAMMING USING TEMPORAL AND TRANSIENT PLASMID VECTOR EXPRESSION SYSTEM

RELATED APPLICATION

This application claims priority to U.S. Provisional Application Ser. No. 62/571,105, filed Oct. 11, 2017, the disclosure of which is hereby incorporated by reference in its entirety.

REFERENCE TO SEQUENCE LISTING SUBMITTED ELECTRONICALLY

This application incorporates by reference a Computer Readable Form (CRF) of a Sequence Listing in ASCII text format submitted with this application, entitled 13601-187-228_SEQ_LISTING.txt, was created on Oct. 9, 2018, and is 9,600 bytes in size.

FIELD OF THE INVENTION

The present disclosure is broadly concerned with the field of generating human induced pluripotent stem cells (iPSCs or iPS cells). More particularly, the present disclosure is concerned with the use of combinations of plasmid vectors to obtain foot-print free iPSCs having desirable properties with a high efficiency.

BACKGROUND OF THE INVENTION iPSCs were originally generated using integrating viral systems to express key transcription factors. Retroviral and lentiviral systems including polycistronic and inducible systems have now been successfully employed in iPSC generation. However, permanent genomic changes due to insertional mutagenesis and the potential for exogenous gene reactivation post iPSC differentiation may present potential problems for subsequent drug screening and therapeutic applications of cells generated by these methods. Indeed, significant differences between iPSC clones generated using the same viral systems have been reported, with a large percentage of clones forming tumors in rodents when transplanted as differentiated neurospheres. Research suggests that iPSCs generated using the same viral methods may behave differently once differentiated. Differences in ectopic gene integration site may result in different insertional mutagenesis and epigenetic regulation of transgene expression. For iPSC generation methods that include integrating systems, many clones may need to be derived and screened to identify those that are stable in both pluripotent and differentiated states.

Various non-integrating systems for iPSC generation have been demonstrated, which include viral and non-viral methods. The non-integrating viral systems for reprogramming include adenovirus vector, Sendai virus vector, and Epstein-Barr virus based episomal vector. The examples of non-integrating non-viral systems for reprogramming include minicircle vector (minimal DNA vector), PiggyBac (transposon), RNA (mRNA or miRNA), and protein (recombinant polypeptides).

There is a substantial need in the art for an efficient production of a homogenous population of foot-print free iPSCs, preferably in a "naïve" or "grounded" state of pluripotency, and preferably in defined culture conditions. The "naïve" or "grounded" state of pluripotency imparts the iPSCs qualities including, but not limited to, high clonality, sustainable self-renewal, minimal spontaneous differentiation and genomic abnormality, and high survivability as dissociated single cells. Methods and compositions, and specifically the novel plasmid vector systems, of the present invention address this need and provide other related advantages in the field of cellular reprogramming.

SUMMARY OF THE INVENTION

By using an efficient but transient and temporal expression system that minimizes the presence of exogenous genes for reduced probability of host genome integration, it is an object of the present disclosure to provide methods and compositions efficient in generating an iPSC without comprising exogenous DNA introduced to a non-pluripotent cell for induction of reprogramming. It is an object of the present disclosure to provide a combinational plasmid system to efficiently produce iPSCs with a "naïve" or "grounded" state of pluripotency and/or high clonality. iPSCs having ground state pluripotency enable long term survival and genetic stability of single cell dissociated iPSCs, and thus make it possible to generate clonal iPSC lines suitable for banking and manipulation such as single cell sorting and/or depletion, clonal iPSC targeted genomic editing, and directed redifferentiation of a homogenous population of iPSCs. Therefore, it is also an object of the present disclosure to provide methods and compositions to generate single cell derived iPSC clonal lines, or derivative cells therefrom, comprising one or several genetic modifications at selected sites, which include polynucleotides insertion, deletion, and substitution, and which modifications are retained and remain functional in subsequently derived cells after differentiation, dedifferentiation, reprogramming, expansion, passaging and/or transplantation.

One aspect of the present application provides a method of reprogramming a non-pluripotent cell to generate a pluripotent cell or a population thereof, which method comprises transfecting a non-pluripotent cell with one or more first plasmids, wherein the first plasmid comprises a replication origin, and a polynucleotide encoding one or more reprogramming factors but does not encode an EBNA or a derivative thereof, wherein at least one of the one or more first plasmids comprises a polynucleotide encoding OCT4; wherein the introduction of one or more first plasmids induces reprogramming process; and optionally introducing to the non-pluripotent cell one of the following: a second plasmid comprising a nucleotide sequence encoding an EBNA, wherein the second plasmid does not comprise a replication origin or polynucleotide(s) encoding reprogramming factor(s); an EBNA mRNA; and an EBNA protein. The transfected cells are then cultured to generate a reprogramming cell which comprises a morphological change from the starting non-pluripotent cell, is essentially free of EBNA, yet lacks the pluripotent cell morphology and does not comprise endogenous OCT4 expression. When the reprogramming cell is further cultured for a sufficient amount of time, one or more pluripotent cells are generated. The reprogramming method provided herein minimizes the pluripotent cell's exposure to the expression of exogenous transgenes that have the potential to integrate into the cell genome and reactivate to either elicit de-differentiation when generating derivative cells or increase propensity for oncogenesis when used in a clinical setting.

In one embodiment, the reprogramming method comprises first introducing to the non-pluripotent cell a combination of plasmids to induce reprogramming. Said combination of plasmids comprises one or more first plasmids, wherein the first plasmid comprises a replication origin, and a polynucleotide encoding one or more reprogramming factors but does not encode an EBNA or a derivative thereof, and wherein at least one first plasmid comprises a polynucleotide encoding OCT4. Said combination of plasmids comprising the one or more first plasmids further comprise a second plasmid which comprises a nucleotide sequence encoding an EBNA, but not a replication origin or polynucleotide(s) encoding reprogramming factor(s). After introducing the plasmid system to the non-pluripotent cell to induce reprogramming, the cells are cultured to generate a reprogramming cell which comprises a morphological change from the starting non-pluripotent cell, to which the combination of plasmids is introduced. The reprogramming cell presenting a morphological change becomes essentially free of EBNA, yet lacks the pluripotent cell morphology; and does not comprise endogenous OCT4 expression. In the provided method of reprogramming, said reprogramming cell is further cultured for a sufficient amount of time to generate one or more pluripotent cells. In some embodiments, the culturing of the reprogramming cell is in the presence of small molecule compounds comprising at least one of a TGFβ inhibitor, a GSK3 inhibitor, a MEK inhibitor and a ROCK inhibitor. In some embodiments, the small molecule compounds comprise a combination of a TGFβ inhibitor, a GSK3 inhibitor, a MEK inhibitor and a ROCK inhibitor.

In some embodiments, the above general method further comprises a step of dissociating the pluripotent cells to obtain single cell dissociated pluripotent cells. In some embodiments, the single cell dissociated pluripotent cells are suspended in a medium. In some embodiments, the single cell dissociated pluripotent cells are sorted by selecting and isolating cells expressing one or more pluripotency markers to enrich for pluripotent cells expressing the selected marker (s). In some other embodiments, the pluripotent cells, or the single dissociated cells, suspended, sorted, or enriched therefrom are cultured to maintain pluripotency in the presence of small molecule compounds comprising at least one of GSK3 inhibitor, a MEK inhibitor and a ROCK inhibitor. In some embodiments, the long-term pluripotency maintenance is at least for 5, 10, 15, or 20 passages, or more.

In some embodiments, the above method is used for inducing reprogramming of a somatic cell, a progenitor cell, or a multipotent cell. In some embodiments of the method, the non-pluripotent cell for reprogramming is a human cell. In some embodiments of the method, the non-pluripotent cell for reprogramming is an immune cell. In some other embodiments, the immune cell for reprogramming may be patient-specific, drug response-specific, or disease condition-specific. In one embodiment, when the non-pluripotent cell for reprogramming using the method as disclosed, a morphological change presented by the reprogramming cell is that of MET (mesenchymal to epithelial transition).

In one embodiment of said method, the reprogramming cell is essentially free of EBNA carried by the second plasmid. In one embodiment, the reprogramming cell is essentially free of the second plasmid. Some embodiments of the method provide reprogramming cells that have been induced for about 4 to 10 days (i.e., 4-10 days post transfection of the plasmids), 5 to 10 days, 6 to 10 days, or for any days in-between, of the plasmid combination. Some embodiments of the method provide reprogramming cells 4 to 12 days, or for any days in-between, post transfection. Yet some embodiments of the method provide reprogramming cells that are 4 to 14 days, or for any days in-tween post transfection. Still some other embodiments of the method provide reprogramming cells 4 to 21 or 4 to 25 days, or for any days in-between, post transfection.

In some embodiments, the method produces pluripotent cells having reduced pluripotency reversion or spontaneous differentiation, for example, as compared to cells introduced with an additional plasmid comprising both oriP and EBNA. In some other embodiments, said method produces pluripotent cells that are essentially free of the polynucleotides of the plasmid combination. In some embodiments, the pluripotent cells essentially free of the polynucleotides of the plasmids are produced without the need for selection or extensive passaging the pluripotent cell. In one embodiment, the method generates pluripotent cells having at least one of the properties: high clonality, genetic stability, and ground state pluripotency. In some embodiments, the method generates pluripotent cells comprising reactivated genes associated with extraembryonic cells.

In some embodiments, the method involves the use of the second plasmid which has a high rate of loss; and thus the expression of EBNA by the second plasmid is short-lived, transient and temporal, in the sense that the EBNA is lost rapidly, and is expressed in cytoplasm, and prior to the appearance of iPSC morphology or endogenous pluripotency gene expression. In some embodiments of the method, the replication origin and/or EBNA comprised in first and second plasmid respectively are EBV-based. In some embodiments of the method, the reprogramming process is conducted under a feeder-free condition, i.e., in medium that is feeder-free. In some other embodiments of the method, the ROCK inhibitor comprised in the medium is thiazovivin.

Another aspect of the present application provides a reprogramming cell or a population thereof obtained after transfecting a non-pluripotent cell with one or more first plasmids, wherein the first plasmid comprises a replication origin, and a polynucleotide encoding one or more reprogramming factors but does not encode an EBNA or a derivative thereof; wherein at least one of the one or more first plasmids comprises a polynucleotide encoding OCT4; and optionally one of: a second plasmid comprising a nucleotide sequence encoding an EBNA, wherein the second plasmid does not comprise a replication origin or polynucleotide(s) encoding reprogramming factor(s), an EBNA mRNA, and an EBNA protein; wherein the reprogramming cell comprises a morphological change from the non-pluripotent cell prior to the introduction of the combination of plasmids, and is essentially free of EBNA or the derivative thereof; wherein the reprogramming cell does not comprise: (i) pluripotent cell morphology; and (ii) endogenous OCT4 expression; and wherein the reprogramming cell is capable of establishing stable pluripotency given a sufficient amount of time to generate a pluripotent cell. In one embodiment, a second plasmid comprising a nucleotide sequence encoding an EBNA is used to generate reprogramming cells and iPSCs, wherein the second plasmid does not comprise a replication origin or polynucleotide(s) encoding reprogramming factor(s). In one embodiment, instead of a second plasmid, an EBNA mRNA is used with the one or more first plasmids to induce reprogramming and generate reprogramming cells and iPSCs having the properties as disclosed. In another embodiment, an EBNA protein or polypeptide is used with the one or more first plasmids to induce reprogramming and generate reprogramming cells and iPSCs having the properties as disclosed.

In some embodiments of the reprogramming cell or a population thereof, the cell has been induced for about 4 to 10, to 12, to 14, to 21, to 25 days, or to any days in-between. In some embodiments, the reprogramming cell or a population thereof is cultured in the presence of a TGFβ inhibitor, a GSK3 inhibitor, a MEK inhibitor and a ROCK inhibitor. In some other embodiments, the reprogramming cell or a population thereof is induced from a fibroblast, as such the morphological change of the reprogramming comprises that of MET (mesenchymal to epithelial transition). In some embodiments, the reprogramming cell or a population thereof is essentially free of first and second plasmids. In some embodiments, the reprogramming cell gives rise to a pluripotent cell that is essentially free of the polynucleotides of the plasmids without the need for selection or extensive passaging the pluripotent cell. In some other embodiments, the reprogramming cell or a population thereof gives rise to a pluripotent cell that has reduced pluripotency reversion or spontaneous differentiation, for example, as compared to cells introduced with an additional plasmid comprising both oriP and EBNA. In yet some other embodiments, the reprogramming cell or a population thereof gives rise to a pluripotent cell that has at least one of the properties: high clonality; genetic stability, and ground state pluripotency. In still another embodiment, the reprogramming cell or a population thereof gives rise to a pluripotent cell that comprises reactivated genes associated with extraembryonic cells.

Another aspect of the present application thus provides a composition comprising the reprogramming cell or a population thereof as described above. In some embodiments, the composition further comprises a medium comprising a TGFβ inhibitor, a GSK3 inhibitor, a MEK inhibitor and a ROCK inhibitor. In one embodiment, the ROCK inhibitor comprised in the medium of the composition is thiazovivin. In other embodiments, the medium is feeder-free. A further aspect of the present application provides an isolated pluripotent cell or a pluripotent cell line produced by said method disclosed herein. In some embodiments, the isolated pluripotent cell or a pluripotent cell line so produced may be further genomically engineered and/or re-differentiated to a non-natural derived cell. In some embodiments, the non-natural derived cell redifferentiated from the isolated pluripotent cell or a pluripotent cell line is an immune cell, including but not being limited to a CD34 cell, a hemogenic endothelium cell, a hematopoietic stem or progenitor cell, a hematopoietic multipotent progenitor cell, a T cell progenitor, an NK cell progenitor, a T cell, a NKT cell, an NK cell, a B cell, and an immune regulatory cell. In some embodiments, the non-natural cells derived from the pluripotent cell or a pluripotent cell line are rejuvenated cells comprising at least one of the properties: global increase of heterochromatin; improved mitochondrial function; increased DNA damage responses; telomere elongation and decrease of percentage of short telomere; decrease in the fraction of senescent cells; and higher potential for proliferation, survival, persistence, or memory like functions, in comparison to its natural cell counterpart.

A further aspect of the present application provides a composition for therapeutic use comprising a pluripotent cell obtained by the method as described herein, and optionally one or more additional therapeutic agents. Also provided is a composition for therapeutic use comprising a genomically engineered pluripotent cell or a derived non-natural cell of claims obtained by the methods as described herein, and optionally one or more additional therapeutic agents. In some embodiments, these compositions for therapeutic use are for use in treating a subject in need thereof. The present application also provides a composition for use in manufacturing a pluripotent cell for application in cell-based therapies. In some embodiments, the pluripotent cell is allogeneic, i.e., reprogrammed from a cell from a subject different from the one who is to receive the cell-based therapies; or autologous, i.e., reprogrammed from cell from the same subject who is to receive the cell-based therapies.

A kit comprising a pluripotent cell obtained by said method as described is provided. In some embodiments, the pluripotent cell comprised in the kit is genomically engineered. Also provided is a kit comprising non-natural cells derived from the pluripotent cell obtained by said method as described.

Still another aspect of the present application provides an in vitro system for initiating reprogramming in a non-pluripotent cell, wherein the system comprises: (1) one or more first plasmids, wherein the first plasmid comprises a replication origin, and a polynucleotide encoding one or more reprogramming factors but does not encode an EBNA or a derivative thereof; wherein at least one of the one or more first plasmids comprises a polynucleotide encoding OCT4; and optionally (2) one of (i) a second plasmid comprising a nucleotide sequence encoding an EBNA, wherein the second plasmid does not comprise a replication origin or polynucleotide(s) encoding reprogramming factor (s), (ii) an EBNA mRNA, and (iii) an EBNA protein. In some embodiments, the second plasmid of the system has a high rate of loss; and wherein the expression of EBNA by the second plasmid is short-lived, transient and temporal. In some other embodiments, the system does not provide EBNA replication and/or continuous expression in the nucleus. In one embodiment, the system could enable a transient/cytoplasmic expression of EBNA for a short duration, and prior to the appearance of pluripotency cell morphology and the induced expression of endogenous pluripotency genes. In some embodiments, the short duration for EBNA expression is about 4, 5, 6, 7, or 8 days post transfection, but no more than 14, 15, 16, 17, 18, 20, 21, 22, 22, 23, 24, or 25 days post transfection. In some other embodiments, the system also enables a transient/cytoplasmic expression of one or more reprogramming factors comprised in first plasmid(s) for a short duration, and prior to the appearance of pluripotency cell morphology and the induced expression of endogenous pluripotency genes.

In one embodiment of the system, the replication origin of first plasmid(s) is one selected from the group consisting of a Polyomavirinae virus, a Papillomavirinae virus, and a Gammaherpesvirinae virus. In some embodiments, the replication origin is one selected from the group consisting of SV40, BK virus (BKV), bovine papilloma virus (BPV), or Epstein-Barr virus (EBV). In one particular embodiment, the replication origin corresponds to, or is derived from, the wild-type replication origin of EBV In some other embodiments, the EBNA of the second plasmid in the system is EBV-based. In some embodiments, the system provides one or more first plasmids collectively comprise polynucleotides encoding reprogramming factor(s) comprising one or more of OCT4, SOX2, NANOG, KLF, LIN28, c-MYC, ECAT1, UTF1, ESRRB, HESRG, CDH1, TDGF1, DPPA4, DNMT3B, ZIC3, and L1TD1. In some embodiments, the polynucleotides encoding reprogramming factors are comprised in a polycistronic construct or non-polycistronic construct in a first plasmid. In one embodiment of a polycistronic construct, it comprises a single open reading frame or multiple open reading frames. In the embodiment where the system comprises two or more first plasmids, each first plasmid may comprise the same or different reprogramming factors encoded by at least one copy of polynucleotide. In those embodiments, where the system comprises two or more first plasmids, the system offers a control of reprogramming factor stoichiometry.

In some embodiments of the system, the first plasmid comprises more than one polynucleotides encoding reprogramming factors, wherein the adjacent polynucleotides are operatively connected by a linker sequence encoding a self-cleaving peptide or an IRES. In one embodiment, the self-cleaving peptide is a 2A peptide is selected from the group comprising F2A, E2A, P2A and T2A. In another embodiment, the 2A peptides comprised in a first plasmid construct may be the same or different. In yet another embodiment where the plasmid of the system comprises multiple 2As, the two 2A peptides in neighboring positions are different. In some other embodiments of the system, the first and the second plasmid each comprises one or more promoters for expression of reprogramming factors and EBNA, and the one or more promoters comprise at least one of CMV, EF1α, PGK, CAG, UBC, and other suitable promoters that are constitutive, inducible, endogenously regulated, or temporal-, tissue- or cell type-specific. In one embodiment, the first and the second plasmid each comprises a CAG promoter.

Also provided is a kit comprising the in vitro system as described herein.

Various objects and advantages of the use of the present methods and compositions will become apparent from the following description taken in conjunction with the accompanying drawings wherein are set forth, by way of illustration and example, certain embodiments of this invention.

DETAILED DESCRIPTION OF THE INVENTION

Definitions

Figure 1:
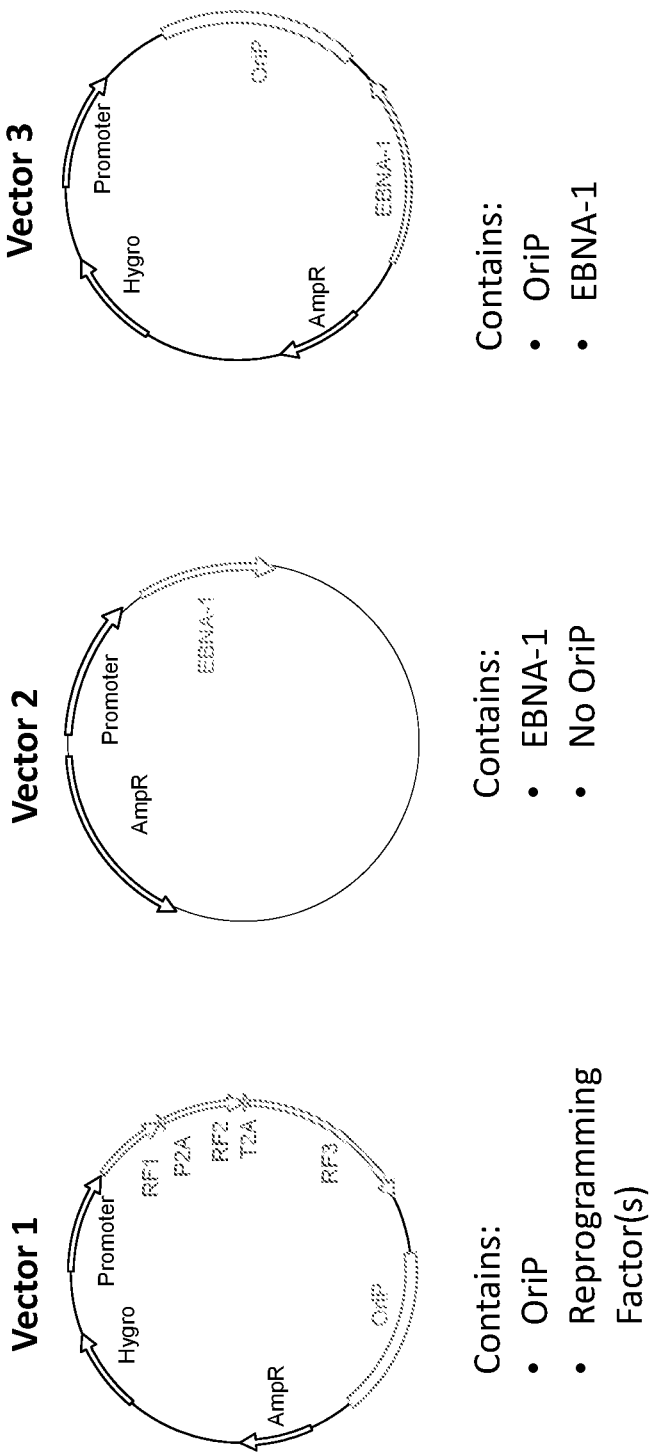
FIG. 1 shows a diagram of DNA constructs of vector 1 and vector 2 used in a STTR (Short-lived Transient and Temporal Reprogramming) system, and an additional vector 3 to be used with vectors 1 and 2 for an EmTTR (EBNA-mediated Transient and Temporal Reprogramming) system.

Unless defined otherwise, all technical and scientific terms used herein have the same meaning as commonly understood by those of ordinary skill in the art to which the invention belongs. For the purposes of the present invention, the following terms are defined below. The articles "a," "an," and "the" are used herein to refer to one or to more than one (i.e. to at least one) of the grammatical object of the article. By way of example, "an element" means one element or more than one element.

The use of the alternative (e.g., "or") should be understood to mean either one, both, or any combination thereof of the alternatives. The term "and/or" should be understood to mean either one, or both of the alternatives.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% compared to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length±15%, ±10%, ±9%, ±8%, ±7%, ±6%, ±5%, ±4%, ±3%, ±2%, or 1% about a reference quantity, level, value, number, frequency, percentage, dimension, size, amount, weight or length.

As used herein, the term "substantially" or "essentially" refers to a quantity, level, value, number, frequency, percentage, dimension, size, amount, weight or length that is about 90%, 91%, 92%, 93%, 94%, 95%, 96%, 97%, 98%, or 99% or higher compared to a reference quantity, level, value, number, frequency, percentage, dimension, size, amount, weight or length. In one embodiment, the terms "essentially the same" or "substantially the same" refer a range of quantity, level, value, number, frequency, percentage, dimension, size, amount, weight or length that is about the same as a reference quantity, level, value, number, frequency, percentage, dimension, size, amount, weight or length.

As used herein, the terms "substantially free of" and "essentially free of" are used interchangeably, and when used to describe a composition, such as a cell population or culture media, refer to a composition that is free of a specified substance or its source thereof, such as, 95% free, 96% free, 97% free, 98% free, 99% free of the specified substance or its source thereof, or is undetectable as measured by conventional means. The term "free of" or "essentially free of" a certain ingredient or substance in a composition also means that no such ingredient or substance is (1) included in the composition at any concentration, or (2) included in the composition functionally inert, but at a low concentration. Similar meaning can be applied to the term "absence of," where referring to the absence of a particular substance or its source thereof of a composition.

As used herein, the term "isolated" or the like refers to a cell, or a population of cells, which has been separated from its original environment, i.e., the environment of the isolated cells is substantially free of at least one component as found in the environment in which the "un-isolated" reference cells exist. The term includes a cell that is removed from some or all components as it is found in its natural environment, for example, tissue, biopsy. The term also includes a cell that is removed from at least one, some or all components as the cell is found in non-naturally occurring environments, for example, culture, cell suspension. Therefore, an isolated cell is partly or completely separated from at least one component, including other substances, cells or cell populations, as it is found in nature or as it is grown, stored or subsisted in non-naturally occurring environments. Specific examples of isolated cells include partially pure cells, substantially pure cells and cells cultured in a medium that is non-naturally occurring. Isolated cells may be obtained from separating the desired cells, or populations thereof, from other substances or cells in the environment, or from removing one or more other cell populations or subpopulations from the environment.

As used herein, the term "purify" or the like refers to increasing purity. For example, the purity can be increased to at least 50%, 60%, 70%, 80%, 90%, 95%, 99%, or 100%.

Throughout this specification, unless the context requires otherwise, the words "comprise," "comprises" and "comprising" will be understood to imply the inclusion of a stated step or element or group of steps or elements but not the exclusion of any other step or element or group of steps or elements. In particular embodiments, the terms "include," "has," "contains," and "comprise" are used synonymously.

By "consisting of" is meant including, and limited to, whatever follows the phrase "consisting of." Thus, the phrase "consisting of" indicates that the listed elements are required or mandatory, and that no other elements may be present.

By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

The term "ex vivo" refers generally to activities that take place outside an organism, such as experimentation or measurements done in or on living tissue in an artificial environment outside the organism, preferably with minimum alteration of the natural conditions. In particular embodiments, "ex vivo" procedures involve living cells or tissues taken from an organism and cultured in a laboratory apparatus, usually under sterile conditions, and typically for a few hours or up to about 24 hours, but including up to 48 or 72 hours or longer, depending on the circumstances. In certain embodiments, such tissues or cells can be collected and frozen, and later thawed for ex vivo treatment. Tissue culture experiments or procedures lasting longer than a few days using living cells or tissue are typically considered to be "in vitro," though in certain embodiments, this term can be used interchangeably with ex vivo.

The term "in vivo" refers generally to activities that take place inside an organism.

As used herein, the terms "reprogramming" or "dedifferentiation" or "increasing cell potency" or "increasing developmental potency" refers to a method or a process of increasing the pluripotency of a cell or dedifferentiating the cell to a less differentiated state. For example, a cell that has an increased cell pluripotency has more developmental plasticity (i.e., can differentiate into more cell types) compared to the same cell in the non-reprogrammed state. In other words, a reprogrammed cell is one that is in a less differentiated state than the same cell in a non-reprogrammed state. A "reprogramming cell," as opposed to a reprogrammed cell, refers to a non-pluripotent cell undergoing reprogramming/dedifferentiation to a pluripotent state, presenting a transitional morphology (i.e., a change in morphology) yet without the hallmarks of a pluripotent cell, including pluripotent stem cell morphology or stable endogenous pluripotency gene expression such as OCT4, NANOG SOX2, SSEA4, TRA181, CD30 and/or CD50. The transitional morphology of a reprogramming cell distinguishes the cell from the starting non-pluripotent cell prior to reprogramming induction, as well as from a reprogrammed cell having the embryonic stem cell hallmark morphology. For example, when reprogramming a fibroblast, the morphological change of the reprogramming cell comprises MET (mesenchymal to epithelial transition). A person skilled in the art understands and identifies readily such transitional morphology for various types of somatic cell induced to reprogram. In some embodiments, the reprogramming cells are intermediary cells that have been induced to reprogram for at least 1, 2, 3, 4, 5, 6, 7, 8, or more days, but no more than 21, 22, 24, 26, 28, 30, 32, 35, 40 days or any number of days in between, wherein the cells have not entered a self-maintaining or self-sustaining pluripotent state. A non-pluripotent cell is induced to reprogram when the cell is introduced with one or more reprogramming factors. A reprogramming cell that has been induced to reprogram for 1, 2, 3, or 4 days is a cell 1, 2, 3, or 4 days post transduction of the reprogramming factors (the day of transduction is day 0). Unlike the somatic cell prior to the exposure to the exogenous expression of reprogramming factors, a reprogramming cell can progress the reprogramming process to reach a stable pluripotent state and becomes a reprogrammed cell even without the presence of the exogenous expression reprogramming factors, so long as a sufficient time period is given.

As used herein, the term "induced pluripotent stem cells" or, "iPSCs", means that the stem cells are produced from differentiated adult, neonatal or fetal cells that have been induced or changed (i.e., reprogrammed) into cells capable of differentiating into tissues of all three germ or dermal layers: mesoderm, endoderm, and ectoderm.

As used herein, the term "embryonic stem cell" refers to naturally occurring pluripotent stem cells of the inner cell mass of the embryonic blastocyst. Embryonic stem cells are pluripotent and give rise during development to all derivatives of the three primary germ layers: ectoderm, endoderm and mesoderm. They do not contribute to the extraembryonic membranes or the placenta and are not totipotent.

As used herein, the term "multipotent stem cell" refers to a cell that has the developmental potential to differentiate into cells of one or more germ layers (ectoderm, mesoderm and endoderm), but not all three. Thus, a multipotent cell can also be termed a "partially differentiated cell." Multipotent cells are well known in the art, and examples of multipotent cells include adult stem cells, such as for example, hematopoietic stem cells and neural stem cells. "Multipotent" indicates that a cell may form many types of cells in a given lineage, but not cells of other lineages. For example, a multipotent hematopoietic cell can form the many different types of blood cells (red, white, platelets, etc.), but it cannot form neurons. Accordingly, the term "multipotency" refers to a state of a cell with a degree of developmental potential that is less than totipotent and pluripotent.

As used herein, the term "pluripotent" refers to the ability of a cell to form all lineages of the body or soma (i.e., the embryo proper). For example, embryonic stem cells are a type of pluripotent stem cells that are able to form cells from each of the three germs layers, the ectoderm, the mesoderm, and the endoderm. Pluripotency is a continuum of developmental potencies ranging from the incompletely or partially pluripotent cell (e.g., an epiblast stem cell or EpiSC), which is unable to give rise to a complete organism to the more primitive, more pluripotent cell, which is able to give rise to a complete organism (e.g., an embryonic stem cell).

Pluripotency can be determined, in part, by assessing pluripotency characteristics of the cells. Pluripotency characteristics include, but are not limited to: (i) pluripotent stem cell morphology; (ii) the potential for unlimited self-renewal; (iii) expression of pluripotent stem cell markers including, but not limited to SSEA1 (mouse only), SSEA3/4, SSEA5, TRA1-60, TRA1-81, TRA1-85, TRA2-54, GCTM-2, TG343, TG30, CD9, CD29, CD133/prominin, CD140a, CD56, CD73, CD90, CD105, OCT4, NANOG SOX2, CD30 and/or CD50; (iv) ability to differentiate to all three somatic lineages (ectoderm, mesoderm and endoderm); (v) teratoma formation consisting of the three somatic lineages; and (vi) formation of embryoid bodies consisting of cells from the three somatic lineages.

Two types of pluripotency have previously been described: the "primed" or "metastable" state of pluripotency akin to the epiblast stem cells (EpiSC) of the late blastocyst, and the "Naïve" or "Ground" state of pluripotency akin to the inner cell mass of the early/preimplantation blastocyst. While both pluripotent states exhibit the characteristics as described above, the naïve or ground state further exhibits: (i) pre-inactivation or reactivation of the X-chromosome in female cells; (ii) improved clonality and survival during single-cell culturing; (iii) global reduction in DNA methylation; (iv) reduction of H3K27me3 repressive chromatin mark deposition on developmental regulatory gene promoters; and (v) reduced expression of differentiation markers relative to primed state pluripotent cells. Standard methodologies of cellular reprogramming in which exogenous pluripotency genes are introduced to a somatic cell, expressed, and then either silenced or removed from the resulting pluripotent cells are generally seen to have characteristics of the primed-state of pluripotency. Under standard pluripotent cell culture conditions such cells remain in the primed state unless the exogenous transgene expression is maintained, wherein characteristics of the ground-state are observed.

As used herein, the term "pluripotent stem cell morphology" refers to the classical morphological features of an embryonic stem cell. Normal embryonic stem cell morphology is characterized by being round and compact in shape, with a high nucleus-to-cytoplasm ratio, the notable presence of nucleoli, and typical inter-cell spacing.

A "pluripotency factor," or "reprogramming factor," refers to an agent or a combination of agents used for inducing or increasing the developmental potency of a cell. Pluripotency factors include, without limitation, polynucleotides, polypeptides, and small molecules capable of increasing the developmental potency of a cell. Exemplary pluripotency factors include, for example, transcription factors OCT4 and SOX2, and small molecule reprogramming agents, for example, TGFβ inhibitor, GSK3 inhibitor, MEK inhibitor and ROCK inhibitor.

As used herein, the term "differentiation" is the process by which an unspecialized ("uncommitted") or less specialized cell acquires the features of a specialized cell such as, for example, a blood cell or a muscle cell. A differentiated or differentiation-induced cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type.

Differentiation of pluripotent stem cells requires a change in the culture system, such as changing the stimuli agents in the culture medium or the physical state of the cells. The most conventional strategy utilizes the formation of embryoid bodies (EBs) as a common and critical intermediate to initiate the lineage-specific differentiation. "Embryoid bodies" are three-dimensional clusters that have been shown to mimic embryo development as they give rise to numerous lineages within their three-dimensional area. Through the differentiation process, typically few hours to days, simple EBs (for example, aggregated pluripotent stem cells elicited to differentiate) continue maturation and develop into a cystic EB at which time, typically days to few weeks, they are further processed to continue differentiation. EB formation is initiated by bringing pluripotent stem cells into close proximity with one another in three-dimensional multilayered clusters of cells, typically this is achieved by one of several methods including allowing pluripotent cells to sediment in liquid droplets, sedimenting cells into "U" bottomed well-plates or by mechanical agitation. To promote EB development, the pluripotent stem cell aggregates require further differentiation cues, as aggregates maintained in pluripotent culture maintenance medium do not form proper EBs. As such, the pluripotent stem cell aggregates need to be transferred to differentiation medium that provides eliciting cues towards the lineage of choice. EB-based culture of pluripotent stem cells typically results in generation of differentiated cell populations (ectoderm, mesoderm and endoderm germ layers) with modest proliferation within the EB cell cluster. Although proven to facilitate cell differentiation, EBs, however, give rise to heterogeneous cells in variable differentiation state because of the inconsistent exposure of the cells in the three-dimensional structure to differentiation cues from the environment. In addition, EBs are laborious to create and maintain. Moreover, cell differentiation through EB is accompanied with modest cell expansion, which also contributes to low differentiation efficiency.

In comparison, "aggregate formation," as distinct from "EB formation," can be used to expand the populations of pluripotent stem cell derived cells. For example, during aggregate-based pluripotent stem cell expansion, culture media are selected to maintain proliferation and pluripotency. Cell proliferation generally increases the size of the aggregates forming larger aggregates, these aggregates can be routinely mechanically or enzymatically dissociated into smaller aggregates to maintain cell proliferation within the culture and increase numbers of cells. As distinct from EB culture, cells cultured within aggregates in maintenance culture maintain markers of pluripotency. The pluripotent stem cell aggregates require further differentiation cues to induce differentiation.

As used herein, "monolayer differentiation" is a term referring to a differentiation method distinct from differentiation through three-dimensional multilayered clusters of cells, i.e., "EB formation." Monolayer differentiation, among other advantages disclosed herein, avoids the need for EB formation for differentiation initiation. Because monolayer culturing does not mimic embryo development such as EB formation, differentiation towards specific lineages are deemed as minimal as compared to all three germ layer differentiation in EB.

As used herein, a "dissociated" cell refers to a cell that has been substantially separated or purified away from other cells or from a surface (e.g., a culture plate surface). For example, cells can be dissociated from an animal or tissue by mechanical or enzymatic methods. Alternatively, cells that aggregate in vitro can be dissociated from each other, such as by dissociation into a suspension of clusters, single cells or a mixture of single cells and clusters, enzymatically or mechanically. In yet another alternative embodiment, adherent cells are dissociated from a culture plate or other surface. Dissociation thus can involve breaking cell interactions with extracellular matrix (ECM) and substrates (e.g., culture surfaces), or breaking the ECM between cells.

As used herein, "feeder cells" or "feeders" are terms describing cells of one type that are co-cultured with cells of a second type to provide an environment in which the cells of the second type can grow, as the feeder cells provide growth factors and nutrients for the support of the second cell type. The feeder cells are optionally from a different species as the cells they are supporting. For example, certain types of human cells, including stem cells, can be supported by primary cultures of mouse embryonic fibroblasts, or immortalized mouse embryonic fibroblasts. The feeder cells may typically be inactivated when being co-cultured with other cells by irradiation or treatment with an anti-mitotic agent such as mitomycin to prevent them from outgrowing the cells they are supporting. Feeder cells may include endothelial cells, stromal cells (for example, epithelial cells or fibroblasts), and leukemic cells. Without limiting the foregoing, one specific feeder cell type may be a human feeder, such as a human skin fibroblast. Another feeder cell type may be mouse embryonic fibroblasts (MEF). In general, various feeder cells can be used in part to maintain pluripotency, direct differentiation towards a certain lineage and promote maturation to a specialized cell types, such as an effector cell.

As used herein, a "feeder-free" (FF) environment refers to an environment such as a culture condition, cell culture or culture media which is essentially free of feeder cells, and/or which has not been pre-conditioned by the cultivation of feeder cells. "Pre-conditioned" medium refers to a medium harvested after feeder cells have been cultivated within the medium for a period of time, such as for at least one day. Pre-conditioned medium contains many mediator substances, including growth factors and cytokines secreted by the feeder cells. In some embodiments, a feeder-free environment is free of both feeder cells and is also not preconditioned by the cultivation of feeder cells. Feeder cells include, but without limitation, stromal cells, mouse embryonic fibroblasts, human fibroblasts, keratinocytes, and embryonic stem cells.

"Culture" or "cell culture" refers to the maintenance, growth and/or differentiation of cells in an in vitro environment. "Cell culture media," "culture media" (singular "medium" in each case), "supplement" and "media supplement" refer to nutritive compositions that cultivate cell cultures.

"Cultivate," or "maintain," refers to the sustaining, propagating (growing) and/or differentiating of cells outside of tissue or the body, for example in a sterile plastic (or coated plastic) cell culture dish or flask. "Cultivation," or "maintaining," may utilize a culture medium as a source of nutrients, hormones and/or other factors helpful to propagate and/or sustain the cells.

As used herein, "passage" or "passaging" refers to the act of splitting the cultured cells by subdividing and plating cells into multiple cell culture surfaces or vessels when the cells have proliferated to a desired extent. In some embodiments "passage" or "passaging" refers to subdividing, diluting and plating the cells. As cells are passaged from the primary culture surface or vessel into a subsequent set of surfaces or vessels, the subsequent cultures may be referred to herein as "secondary culture" or "first passage," etc. Each act of subdividing and plating into a new culture vessel is considered one passage. In some embodiments, the cultured cells are passaged every 1, 2, 3, 4, 5, 6, 7, or more, days. In some embodiments, the initially selected iPSCs after reprogramming are passaged once every 3-7 days.

"Functional" as used in the context of genomic editing or modification of iPSC, and derived non-pluripotent cells differentiated therefrom, or genomic editing or modification of non-pluripotent cells and derived iPSCs reprogrammed therefrom, refers to (1) at the gene level—successful knocked-in, knocked-out, knocked-down gene expression, transgenic or controlled gene expression such as inducible or temporal expression at a desired cell development stage, which is achieved through direct genomic editing or modification, or through "passing-on" via differentiation from or reprogramming of a starting cell that is initially genomically engineered; or (2) at the cell level-successful removal, adding, or altering a cell function/characteristics via (i) gene expression modification obtained in said cell through direct genomic editing, (ii) gene expression modification maintained in said cell through "passing-on" via differentiation from or reprogramming of a starting cell that is initially genomically engineered; (iii) down-stream gene regulation in said cell as a result of gene expression modification that only appears in an earlier development stage of said cell, or only appears in the starting cell that gives rise to said cell via differentiation or reprogramming; or (iv) enhanced or newly attained cellular function or attribute displayed within the mature cellular product, initially derived from the genomic editing or modification conducted at the iPSC, progenitor or dedifferentiated cellular origin.

As used herein, the term "genetic imprint" refers to genetic or epigenetic information that contributes to preferential therapeutic attributes in a source cell or an iPSC, and is retainable in the source cell derived iPSCs, and/or the iPSC-derived non-natural hematopoietic lineage cells. As used herein, "a source cell" is a non-pluripotent cell that may be used for generating iPSCs through reprogramming, and the source cell derived iPSCs may be further differentiated to specific cell types including any hematopoietic lineage cells. The source cell derived iPSCs, and differentiated cells therefrom are sometimes collectively called "derived cells" depending on the context. As used herein, the genetic imprint(s) conferring a preferential therapeutic attribute is incorporated into the iPSCs either through reprogramming a selected source cell that is donor-, disease-, or treatment response-specific, or through introducing genetically modified modalities to iPSC using genomic editing. In the aspect of a source cell obtained from a specifically selected donor, disease or treatment context, the genetic imprint contributing to preferential therapeutic attributes may include any context specific genetic or epigenetic modifications which manifest a retainable phenotype, i.e. a preferential therapeutic attribute, that is passed on to derivative cells of the selected source cell, irrespective of the underlying molecular events being identified or not. Donor-, disease-, or treatment response-specific source cells may comprise genetic imprints that are retainable in iPSCs and derived hematopoietic lineage cells, which genetic imprints include but are not limited to, prearranged monospecific TCR, for example, from a viral specific T cell or invariant natural killer T (iNKT) cell; trackable and desirable genetic polymorphisms, for example, homozygous for a point mutation that encodes for the high-affinity CD16 receptor in selected donors; and predetermined HLA requirements, i.e., selected HLA-matched donor cells exhibiting a haplotype with increased population. As used herein, preferential therapeutic attributes include improved engraftment, trafficking, homing, viability, self-renewal, persistence, immune response regulation and modulation, survival, and cytotoxicity of a derived cell. A preferential therapeutic attribute may also relate to antigen targeting receptor expression; HLA presentation or lack thereof; resistance to tumor microenvironment; induction of bystander immune cells and immune modulations; improved on-target specificity with reduced off-tumor effect; resistance to treatment such as chemotherapy.

As used herein, "genetic modification" refers to genetic editing including those (1) naturally derived from rearrangements, mutations, genetic imprinting and/or epigenetic modification, or (2) obtained through genomic engineering through insertion, deletion or substitution in the genome of a cell. Genetic modification, as used herein, also includes one or more retainable therapeutic attributes of a source-specific immune cell that is donor-, disease-, or treatment response-specific.

The term "enhanced therapeutic property" as used herein, refers to a therapeutic property of a cell that is enhanced as compared to a typical cell of the same general cell type. In the context of immune cells, for example, an NK cell with an "enhanced therapeutic property" will possess an enhanced, improved, and/or augmented therapeutic property as compared to a typical, unmodified, and/or naturally occurring NK cell. Therapeutic properties of an immune cell may include, but are not limited to, cell engraftment, trafficking, homing, viability, self-renewal, persistence, immune response regulation and modulation, survival, and cytotoxicity. Therapeutic properties of an immune cell are also manifested by antigen targeting receptor expression; HLA presentation or lack thereof; resistance to tumor microenvironment; induction of bystander immune cells and immune modulations; improved on-target specificity with reduced off-tumor effect; resistance to treatment such as chemotherapy.

By "integration" it is meant that one or more nucleotides of a construct is stably inserted into the cellular genome, i.e., covalently linked to the nucleic acid sequence within the cell's chromosomal DNA. By "targeted integration" it is meant that the nucleotide(s) of a construct is inserted into the cell's chromosomal or mitochondrial DNA at a pre-selected site or "integration site". The term "integration" as used herein further refers to a process involving insertion of one or more exogenous sequences or nucleotides of the construct, with or without deletion of an endogenous sequence or nucleotide at the integration site. In the case, where there is a deletion at the insertion site, "integration" may further comprise replacement of the endogenous sequence or a nucleotide that is deleted with the one or more inserted nucleotides.

A "construct" refers to a macromolecule or complex of molecules comprising a polynucleotide to be delivered to a host cell, either in vitro or in vivo. A "vector," as used herein refers to any nucleic acid construct capable of directing the delivery or transfer of a foreign genetic material to target cells, where it can be replicated and/or expressed. The term "vector" as used herein comprises the construct to be delivered. A vector can be a linear or a circular molecule. A vector can be integrating or non-integrating. The major types of vectors include, but are not limited to, plasmids, episomal vector, viral vectors, cosmids, and artificial chromosomes. Viral vectors include, but are not limited to, adenovirus vector, adeno-associated virus vector, retrovirus vector, lentivirus vector, Sendai virus vector, and the like.

As used herein, the term "encoding" refers to the inherent property of specific sequences of nucleotides in a polynucleotide, such as a gene, a cDNA, or a mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein, the term "exogenous" in intended to mean that the referenced molecule or the referenced activity is introduced into the host cell. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the cell. The term "endogenous" refers to a referenced molecule or activity that is present in the host cell. Similarly, the term when used in reference to expression of an encoding nucleic acid refers to expression of an encoding nucleic acid contained within the cell and not exogenously introduced.

As used herein, a "gene of interest" or "a polynucleotide sequence of interest" is a DNA sequence that is transcribed into RNA and in some instances translated into a polypeptide in vivo when placed under the control of appropriate regulatory sequences. A gene or polynucleotide of interest can include, but is not limited to, prokaryotic sequences, cDNA from eukaryotic mRNA, genomic DNA sequences from eukaryotic (e.g., mammalian) DNA, and synthetic DNA sequences. For example, a gene of interest may encode an miRNA, an shRNA, a native polypeptide (i.e. a polypeptide found in nature) or fragment thereof; a variant polypeptide (i.e. a mutant of the native polypeptide having less than 100% sequence identity with the native polypeptide) or fragment thereof; an engineered polypeptide or peptide fragment, a therapeutic peptide or polypeptide, an imaging marker, a selectable marker, and the like.

As used herein, the term "polynucleotide" refers to a polymeric form of nucleotides of any length, either deoxyribonucleotides or ribonucleotides or analogs thereof. The sequence of a polynucleotide is composed of four nucleotide bases: adenine (A); cytosine (C); guanine (G); thymine (T); and uracil (U) for thymine when the polynucleotide is RNA. A polynucleotide can include a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. Polynucleotide also refers to both double- and single-stranded molecules.

As used herein, the term "peptide," "polypeptide," and "protein" are used interchangeably and refer to a molecule having amino acid residues covalently linked by peptide bonds. A polypeptide must contain at least two amino acids, and no limitation is placed on the maximum number of amino acids of a polypeptide. As used herein, the terms refer to both short chains, which are also commonly referred to in the art as peptides, oligopeptides and oligomers, for example, and to longer chains, which generally are referred to in the art as polypeptides or proteins. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural polypeptides, recombinant polypeptides, synthetic polypeptides, or a combination thereof.

"Operably-linked" refers to the association of nucleic acid sequences on a single nucleic acid fragment so that the function of one is affected by the other. For example, a promoter is operably-linked with a coding sequence or functional RNA when it is capable of affecting the expression of that coding sequence or functional RNA (i.e., the coding sequence or functional RNA is under the transcriptional control of the promoter). Coding sequences can be operably-linked to regulatory sequences in sense or antisense orientation.

As used herein, the term "engager" refers to a molecule, e.g. a fusion polypeptide, which is capable of forming a link between an immune cell, e.g. a T cell, a NK cell, a NKT cell, a B cell, a macrophage, a neutrophil, and a tumor cell; and activating the immune cell. Examples of engagers include, but are not limited to, bi-specific T cell engagers (BiTEs), bi-specific killer cell engagers (BiKEs), tri-specific killer cell engagers, or multi-specific killer cell engagers, or universal engagers compatible with multiple immune cell types.

As used herein, the term "surface triggering receptor" refers to a receptor capable of triggering or initiating an immune response, e.g. a cytotoxic response. Surface triggering receptors may be engineered, and may be expressed on effector cells, e.g. a T cell, a NK cell, a NKT cell, a B cell, a macrophage, a neutrophil. In some embodiments, the surface triggering receptor facilitates bi- or multi-specific antibody engagement between the effector cells and specific target cell e.g. a tumor cell, independent of the effector cell's natural receptors and cell types. Using this approach, one may generate iPSCs comprising a universal surface triggering receptor, and then differentiate such iPSCs into populations of various effector cell types that express the universal surface triggering receptor. By "universal", it is meant that the surface triggering receptor can be expressed in, and activate, any effector cells irrespective of the cell type, and all effector cells expressing the universal receptor can be coupled or linked to the engagers having the same epitope recognizable by the surface triggering receptor, regardless of the engager's tumor binding specificities. In some embodiments, engagers having the same tumor targeting specificity are used to couple with the universal surface triggering receptor. In some embodiments, engagers having different tumor targeting specificity are used to couple with the universal surface triggering receptor. As such, one or multiple effector cell types can be engaged to kill one specific type of tumor cells in some case, and to kill two or more types of tumors in some other cases. A surface triggering receptor generally comprises a co-stimulatory domain for effector cell activation and an anti-epitope that is specific to the epitope of an engager. A bi-specific engager is specific to the anti-epitope of a surface triggering receptor on one end, and is specific to a tumor antigen on the other end.

As used herein, the term "safety switch protein" refers to an engineered protein designed to prevent potential toxicity or otherwise adverse effects of a cell therapy. In some instances, the safety switch protein expression is conditionally controlled to address safety concerns for transplanted engineered cells that have permanently incorporated the gene encoding the safety switch protein into its genome. This conditional regulation could be variable and might include control through a small molecule-mediated post-translational activation and tissue-specific and/or temporal transcriptional regulation. The safety switch could mediate induction of apoptosis, inhibition of protein synthesis, DNA replication, growth arrest, transcriptional and post-transcriptional genetic regulation and/or antibody-mediated depletion. In some instance, the safety switch protein is activated by an exogenous molecule, e.g. a prodrug, that when activated, triggers apoptosis and/or cell death of a therapeutic cell. Examples of safety switch proteins, include, but are not limited to suicide genes such as caspase 9 (or caspase 3 or 7), thymidine kinase, cytosine deaminase, B-cell CD20, modified EGFR, and any combination thereof. In this strategy, a prodrug that is administered in the event of an adverse event is activated by the suicide-gene product and kills the transduced cell.

As used herein, the term "pharmaceutically active proteins or peptides" refer to proteins or peptides that are capable of achieving a biological and/or pharmaceutical effect on an organism. A pharmaceutically active protein has healing curative or palliative properties against a disease and may be administered to ameliorate relieve, alleviate, reverse or lessen the severity of a disease. A pharmaceutically active protein also has prophylactic properties and is used to prevent the onset of a disease or to lessen the severity of such disease or pathological condition when it does emerge. Pharmaceutically active proteins include an entire protein or peptide or pharmaceutically active fragments thereof. It also includes pharmaceutically active analogs of the protein or peptide or analogs of fragments of the protein or peptide. The term pharmaceutically active protein also refers to a plurality of proteins or peptides that act cooperatively or synergistically to provide a therapeutic benefit. Examples of pharmaceutically active proteins or peptides include, but are not limited to, receptors, binding proteins, transcription and translation factors, tumor growth suppressing proteins, antibodies or fragments thereof, growth factors, and/or cytokines.

As used herein, the term "signaling molecule" refers to any molecule that modulates, participates in, inhibits, activates, reduces, or increases, the cellular signal transduction. Signal transduction refers to the transmission of a molecular signal in the form of chemical modification by recruitment of protein complexes along a pathway that ultimately triggers a biochemical event in the cell. Signal transduction pathways are well known in the art, and include, but are not limited to, G protein coupled receptor signaling, tyrosine kinase receptor signaling, integrin signaling, toll gate signaling, ligand-gated ion channel signaling, ERK/MAPK signaling pathway, Wnt signaling pathway, cAMP-dependent pathway, and IP3/DAG signaling pathway.

As used herein, the term "targeting modality" refers to a molecule, e.g., a polypeptide, that is genetically incorporated into a cell to promote antigen and/or epitope specificity that includes but not limited to i) antigen specificity as it related to a unique chimeric antigen receptor (CAR) or T cell receptor (TCR), ii) engager specificity as it related to monoclonal antibodies or bispecific engager, iii) targeting of transformed cell, iv) targeting of cancer stem cell, and v) other targeting strategies in the absence of a specific antigen or surface molecule.

As used herein, the term "specific" or "specificity" can be used to refer to the ability of a molecule, e.g., a receptor or an engager, to selectively bind to a target molecule, in contrast to non-specific or non-selective binding.

"HLA deficient", including HLA-class I deficient, or HLA-class II deficient, or both, refers to cells that either lack, or no longer maintain, or have reduced level of surface expression of a complete MHC complex comprising a HLA class I protein heterodimer and/or a HLA class II heterodimer, such that the diminished or reduced level is less than the level naturally detectable by other cells or by synthetic methods. HLA class I deficiency can be achieved by functional deletion of any region of the HLA class I locus (chromosome 6p21), or deletion or reducing the expression level of HLA class-I associated genes including, not being limited to, beta-2 microglobulin (B2M) gene, TAP 1 gene, TAP 2 gene and Tapasin. HLA class II deficiency can be achieved by functional deletion or reduction of HLA-II associated genes including, not being limited to, RFXANK, CIITA, RFX5 and RFXAP. It was unclear, prior to this invention, whether HLA complex deficient or altered iPSCs have the capacity to enter development, mature and generate functional differentiated cells while retaining modulated activity. In addition, it was unclear, prior to this invention, whether HLA complex deficient differentiated cells can be reprogrammed to iPSCs and maintained as pluripotent stem cells while having the HLA complex deficiency. Unanticipated failures during cellular reprogramming, maintenance of pluripotency and differentiation may be related to aspects including, but not limited to, development stage specific gene expression or lack thereof, requirements for HLA complex presentation, protein shedding of introduced surface expressing modalities, need for proper and efficient clonal reprogramming, and need for reconfiguration of differentiation protocols.

"Modified HLA deficient iPSC," as used herein, refers to HLA deficient iPSC that is further modified by introducing genes expressing proteins related but not limited to improved differentiation potential, antigen targeting, antigen presentation, antibody recognition, persistence, immune evasion, resistance to suppression, proliferation, co-stimulation, cytokine stimulation, cytokine production (autocrine or paracrine), chemotaxis, and cellular cytotoxicity, such as non-classical HLA class I proteins (e.g., HLA-E and HLA-G), chimeric antigen receptor (CAR), T cell receptor (TCR), CD16 Fc Receptor, BCL11b, NOTCH, RUNX1, IL15, 41BB, DAP10, DAP12, CD24, CD3z, 41BBL, CD47, CD113, and PDL1. The cells that are "modified HLA deficient" also include cells other than iPSCs.

"Fc receptors," abbreviated FcR, are classified based on the type of antibody that they recognize. For example, those that bind the most common class of antibody, IgG are called Fc-gamma receptors (FcγR), those that bind IgA are called Fc-alpha receptors (FcaR) and those that bind IgE are called Fc-epsilon receptors (FccR). The classes of FcR's are also distinguished by the cells that express them (macrophages, granulocytes, natural killer cells, T and B cells) and the signalling properties of each receptor. Fc-gamma receptors (FcγR) includes several members, FcγRI (CD64), FcγRIIA (CD32), FcγRIIB (CD32), FcγRIIIA (CD16a), FcγRIIIB (CD16b), which differ in their antibody affinities due to their different molecular structure.

CD16 has been identified as two isoforms, Fc receptors FcγRIIIa (CD16a) and FcγRIIIb (CD16b). CD16a is a transmembrane protein expressed by NK cells, which binds monomeric IgG attached to target cells to activate NK cells and facilitate antibody-dependent cell-mediated cytotoxicity (ADCC). "High affinity CD16," "non-cleavable CD16," or "high affinity non-cleavable CD16," as used herein, refers to a variant of CD16. The wildtype CD16 has low affinity and is subject to extodomain shedding, a proteolytic cleavage process that regulates the cells surface density of various cell surface molecules on leukocytes upon NK cell activation. F176V and F158V are exemplary CD16 variants having high affinity; whereas S197P variant is an example of non-cleavable version of CD16.

The term "adoptive cell therapy" as used herein refers to a cell-based immunotherapy that, as used herein, relates to the transfusion of autologous or allogeneic lymphocytes, such as CD34 cells, hemogenic endothelium cells, hematopoietic stem or progenitor cells, hematopoietic multipotent progenitor cells, T cell progenitor, NK cell progenitor, T cells, NKT cells, NK cells, B cells, or immune regulatory cells, genetically modified or not, that have been expanded ex vivo prior to said transfusion.

A "therapeutically sufficient amount", as used herein, includes within its meaning a non-toxic but sufficient and/or effective amount of the particular therapeutic and/or pharmaceutical composition to which it is referring to provide a desired therapeutic effect. The exact amount required will vary from subject to subject depending on factors such as the patient's general health, the patient's age and the stage and severity of the condition. In particular embodiments, a therapeutically sufficient amount is sufficient and/or effective to ameliorate, reduce, and/or improve at least one symptom associated with a disease or condition of the subject being treated.

As used herein, the term "subject" refers to any animal, preferably a human patient, livestock, or other domesticated animal.

As used herein, the terms "treat," "treatment" and the like, when used in reference to a subject in need of a therapeutic treatment, refer to obtaining a desired pharmacologic and/or physiologic effect, including without limitation achieving an improvement or elimination of the symptoms of a disease. The effect can be prophylactic in terms of completely or partially preventing a disease or symptom thereof and/or can be therapeutic in terms of achieving an improvement or elimination of symptoms, or providing a partial or complete cure for a disease and/or adverse effect attributable to the disease. The term "treatment" includes any treatment of a disease in a mammal, particularly in a human, and includes: (a) preventing the disease from occurring in a subject which can be predisposed to the disease but has not yet been diagnosed as having it; (b) inhibiting the disease, or arresting its development; (c) relieving the disease, or causing regression of the disease, or completely or partially eliminating symptoms of the disease; and (d) restoring the individual to a pre-disease state, such as reconstituting the hematopoietic system.

I. A Novel Reprogramming System and the Cells Generated Therefrom

Generally the present disclosure provides a reprogramming process initiated by contacting non-pluripotent cells with at least one reprogramming factor, and optionally in the presence of a combination of a TGFβ receptor/ALK inhibitor, a MEK inhibitor, a GSK3 inhibitor and a ROCK inhibitor (FRM; Table 1).

| Conventional hESC Medium (Conv.) | Fate Reprogramming Medium (FRM) | Fate Maintenance Medium (FMM) |
|---|---|---|
| DMEM/F12 | DMEM/F12 | DMEM/F12 |
| Knockout Serum | Knockout Serum<br>N2<br>B27 | Knockout Serum |
| Glutamine | Glutamine | Glutamine (1x) |
| Non-Essential Amino Acids | Non-Essential Amino Acids | Non-Essential Amino Acids |
| β-mercaptoethanol | β-mercaptoethanol | β-mercaptoethanol |
| bFGF (0.2-50 ng/mL) | bFGF (2-500 ng/mL) | bFGF (2-500 ng/mL) |
|  | LIF (0.2-50 ng/mL) | LIF (0.2-50 ng/mL) |
|  | Thiazovivin (0.1-25 μM) | Thiazovivin (0.1-25 μM) |
|  | PD0325901 (0.005-2 μM) | PD0325901 (0.005-2 μM) |
|  | CHIR99021 (0.02-5 μM) | CHIR99021 (0.02-5 μM) |
|  | SB431542 (0.04-10 μM) |  |
| In combination with MEF | Feeder-free, in combination with Matrigel ™ or Vitronectin | |

One aspect of the present invention provides a method of obtaining footprint-free iPSCs using a plasmid system that mediates transient and temporal transgene expression. The plasmid system comprises one or more first plasmids (V1) carrying a replication origin and polynucleotides encoding reprogramming factor(s) but without EBNA, and a second plasmid (V2) comprising EBNA encoding polynucleotides but without a replication origin or reprogramming factor encoding sequences.

The combination of the plasmids enables cytoplasmic expression of transgenes (EBNA and exogenous reprogramming factors) temporally in the cell upon transduction, and generates a population of EBNA-free intermediary cells that present a transitional morphology, or a morphological change (for example mesenchymal to epithelial transition (MET)), but lacks any pluripotent cell morphology or endogenous pluripotency gene expression, such as OCT4, yet are capable of entering a stable self-sustaining pluripotent state. This distinct cell population is thus termed as "reprogramming cells". A reprogramming cell as described herein also differs from the somatic cell prior to the introduction of the reprogramming factors not only morphologically but functionally as well, in that it is capable of reprogramming to a pluripotent state given a sufficient time period under a culture condition that supports the reprogramming process (for example, FMM). As such, one aspect of the present disclosure provides an EBNA-free reprogramming cell having a transitional morphology and capable of carrying on the reprogramming process to establish a stable pluripotent state. In some embodiments, the EBNA-free reprogramming cells are transgene-free. The resultant iPSC population and the iPSCs are therefore footprint-free without the need of either selection against EBNA, or continuous passaging to eliminate EBNA and transgenes as required in episomal reprogramming. Further, the iPSCs generated using this transient and temporal short-lived plasmid system have at least one of the properties including improved clonality and genetic stability, high homogeneity, high rate of normal karyotype, minimal reversion or spontaneous differentiation; and are capable of single cell survival and sorting, long-term expansion and self-renewal, and monolayer differentiation, with or without feeder conditions.

It is generally accepted in the field that the exogenously introduced reprogramming factors need to be expressed for at least 10-12 days in order to generate iPSCs (Okita et al., Science (2008); 322:949-953; Brambrink et al., Cell Stem Cell (2008); 2(2):151-159; Stadtfeld et al., Cell Stem Cell (2008); 2(3):230-240). Adenoviral transduction of the exogenous transcription factors sometimes requires repeated transfection because of the transient nature of the gene expression mediated by the non-integrating viral vector. In addition, the reprogramming efficiency using adenoviral method is only 0.001-0.0001% in mouse (Stadtfeld et al., Science (2008); 322:945-946) and 0.0002% in human cells (Zhou et al., Stem Cells (2009); 27:2667-2674). In the case of Sendai viral vector mediated reprogramming, multiple transduction is not necessary because this viral vector can continuously produce large amounts of exogenous protein over a long period of time creating a certain dependency on transgene expression to maintain pluripotency. Sendai virus can reprogram neonatal and adult fibroblasts as well as blood cells in about 25 days at a higher efficiency of 0.1%-1%. However, it takes about 10 passages for the virus to be completely lost from recently reprogrammed iPSCs, which is deemed as a disadvantage of Sendai-based reprogramming including increased chance of DNA integration or selection of iPSC-like clones that are supported by transgene expression and not the endogenous circuitry of pluripotent genes (Fusaki et al., Proc Jpn Acad Ser B Phys Biol Sci. (2009); 85:348-362; Seki et al., Cell Stem Cell (2010); 7:11-14; Ban et al., PNAS (2011); 108:14234-14239).

Plasmids, containing a promoter and transgene(s), have poor nuclear uptake, are not replicable, and are lost fast from transfected cells. When used for generating iPS cells, plasmid vectors, including minicircle DNA vectors (minimal plasmid, free of bacterial DNA), have been shown to result in reprogrammed cells under feeder condition with unacceptably low efficiency, and only by repeated daily transfections is efficient reprogramming seen but often resulting in host genome integration of the transfected transgenes (Okita et al., Science (2008); 322:949-953: used standard plasmid with repeated daily transfection, and observed genome integration; obtaining 1-4 integration free clones out of 10E6 cells; Narsinh et al., Nat Protoc. (2011); 6(1): 78-88: an efficiency around 0.005%).

Compared to plasmid, episome can sustain and replicate either autonomously in the cytoplasm or along with the chromosome of a dividing host cell. Episomal vector mediated cell reprogramming has been shown mostly with the application of Epstein-Barr virus (EBV) based episomal vectors. In addition to exogenous gene(s) of interest, EBV-based episomal vectors comprise polynucleotides encoding the Epstein-Barr nuclear antigen-1 (EBNA1) protein and carry the origin of replication (oriP) derived from EBV EBNA binds to cellular chromosomes, enabling nucleus localization of the vector and the tethering of oriP to sister chromatids. Therefore, a stably expressed EBNA acts jointly with oriP to replicate and retain the episomal vector in the nucleus of dividing cells, which provides a stable and long-term expression of the exogenous genes including EBNA in the cell, increasing the likelihood of transgene integration as episomal vectors typically persist for approximately 4-8 weeks (Yates et al., 1984, 1985; Reisman et al., 1985; Sugden et al., 1985). Although oriP/EBNA episomal vectors improve reprogramming efficiency in comparison to plasmid reprogramming, it is, however, still around an unsatisfying range of 0.006%-0.1% (Malik et al., Methods Mol Biol. (2013); 997:23-33).

Other than continuously expressing EBNA in the same vector as oriP, where EBNA is replicated as well as transcribed, a stably expressed EBNA can also be provided by integrating EBNA encoding sequence in the genome of the host cell to improve the transfection rate of the vector containing oriP and transgenes (Mazda et al., 1997, J. Immunol. Methods; 204:143-151). However, such a design, without additional manipulation of the cells, ultimately fails the purpose of obtaining a footprint-free pluripotent cell.

The present reprogramming system, in some embodiments, comprises at least one first plasmid and at least one second plasmid, wherein the first plasmid has a construct providing an oriP and one or more reprogramming factors, but not EBNA; wherein the second plasmid has a construct providing EBNA, but not oriP or reprogramming factors. In some embodiments, the reprogramming system comprises more than one first plasmid, wherein each first plasmid provides the same or different reprogramming factor or a combination thereof. Reprogramming using this plasmid system is different from the conventional plasmid reprogramming method known in the field, in that, there is no need of multiple transfection of the cells, no genomic integration of transgenes, yet with a much higher reprogramming efficiency. In comparison to episomal reprogramming, where the EBNA and reprogramming factor(s) are placed in the same expression cassette and with an oriP present in the same vector, the plasmid system of some embodiments does not provide EBNA replication and/or continuous expression of EBNA and transgenes in the nucleus, but only enables a transient/cytoplasmic expression for a short duration and prior to the appearance of pluripotency cell morphology and the induced expression of endogenous pluripotency genes such as OCT4. Hence, the present disclosure provides footprint-free iPSCs generated from reprogramming cells that are free of EBNA expression at an early stage (for example, around day 4-6 post transfection of a typical 21-32 day reprogramming process), eliminating the otherwise necessary positive selection or continuous passaging of the iPSCs to obtain footprint free iPSCs in episomal reprogramming. In some embodiments, the short duration for EBNA expression is about 4, 5, 6, 7, or 8 days post transfection, but no more than 14, 15, 16, 17, 18, 20, 21, 22, 22, 23, 24, or 25 days post transfection.

The replication origin (oriP) is the site at or near which DNA replication initiates and is composed of two cis-acting sequences: FR (family of repeats) serves as EBNA (Epstein-Barr nuclear antigen)-binding site and also a transcriptional enhancer for promoters in cis; and DS (dyad symmetry element) is for initiation of DNA synthesis upon EBNA binding of FR and is regulated by the host cell replication system. EBNA binding to the FR sites effects the efficient partition of oriP plasmids after replication once-per-cell cycle, which localizes the oriP plasmids to the nucleus and maintains plasmid retention in both daughter cells upon parental cell division. In one embodiment, the oriP may be a replication origin of a Papovaviridae virus, or a Herpesviridae virus. In some embodiments, the oriP may be a replication origin of a Polyomavirinae virus, a Papillomavirinae virus, or a Gammaherpesvirinae virus. In some other embodiments, the oriP may be a replication origin of SV40, BK virus (BKV), bovine papilloma virus (BPV), or Epstein-Barr virus (EBV). In one embodiment, the oriP corresponds to, or is derived from, the wild-type replication origin of EBV. In one embodiment, the EBNA is a polypeptide corresponding to, or a derivative, of a wild-type protein corresponding to EBNA-1 of EBV (UniProtKB/Swiss-Prot Accession No: P03211; SEQ ID NO: 1). A derivative of EBNA-1 is a polypeptide which, relative to a corresponding wild-type polypeptide, has a modified amino acid sequence including deletion, insertion or substitution of one or more amino acids of EBNA-1. In one embodiment, the derivative of EBNA comprises a truncation as compared to the wild-type EBNA. In one embodiment, the truncated EBNA protein has a polypeptide of SEQ ID NO: 2. In other embodiments, the derivative of EBNA-1 encodes a protein with at least 80% amino acid sequence identity to residues about 1 to about 90, residues from 1 to about 40, residues about 41 to about 90, residues about 91 to about 324 (GA rich repeat region), residues about 325 to about 377, residues about 378 to about 386, residues about 451 to about 608, and/or residues about 609 to about 641 in EBNA-1.

Reprogramming factors known for stem cell reprogramming in the field could all be used with the present reprogramming system and method. In one embodiment, the reprogramming factors include, but are not limited to, OCT4, SOX2, NANOG KLF, LIN28, c-MYC, ECAT1, UTF1, ESRRB, HESRG CDH1, TDGF1, DPPA4, DNMT3B, ZIC3, and L1TD1. Polynucleotides encoding these reprogramming factors may be comprised in the same plasmid construct containing oriP but not EBNA (i.e., the same first plasmid). Polynucleotides encoding these reprogramming factors may be comprised in at least two plasmid constructs each containing oriP but not EBNA (i.e., multiple first plasmids). Polynucleotides encoding these reprogramming factors may be comprised in a polycistronic construct (i.e., multiple coding sequences controlled by one promoter) or non-polycistronic construct (multiple coding sequences with some controlled by one promoter and some by a different promoter). The promoter may be, for example, CMV, EF1α, PGK, CAG UBC, and other suitable promoters that are constitutive, inducible, endogenously regulated, or temporal-, tissue- or cell type-specific. In one embodiment, the promoter is CAG In another embodiment, the promoter is EF1α. In some embodiments, the polycistronic construct may provide a single open reading frame (for example, multiple coding sequences are operatively linked by a self-cleaving peptide encoding sequence such as 2A) or multiple open reading frames (for example, multiple coding sequences linked by an Internal Ribosome Entry Site, or IRES).

In some embodiments of the plasmid system of the application, one or more plasmid constructs (first plasmids) collectively comprise polynucleotides encoding one or more reprogramming factors selected from the group consisting of OCT4, SOX2, NANOG KLF, LIN28, c-MYC, ECAT1, UTF1, ESRRB, HESRG CDH1, TDGF1, DPPA4, DNMT3B, ZIC3, and L1TD1. In some embodiments, only one first plasmid construct is in the system and provides all selected reprogramming factors. In some other embodiments, there are two or more first plasmid constructs in the system that provide one or more reprogramming factors, with each construct comprising the same or different reprogramming factors encoded by at least one copy of polynucleotide. In one embodiment, the one or more first plasmid constructs in the system comprise at least polynucleotides encoding OCT4. In one embodiment, the one or more first plasmid constructs collectively comprise at least two polynucleotides encoding OCT4. In another embodiment, the one or more first plasmid constructs collectively comprise polynucleotides encoding OCT4 and SOX2. In one embodiment, the one or more first plasmid constructs collectively comprise at least one polynucleotide encoding OCT4, but not c-MYC. In some embodiments, the one or more first plasmid constructs collectively comprise at least two polynucleotides encoding OCT4, and one or more polynucleotides encoding at least one of ECAT1, UTF1, ESRRB, HESRG CDH1, TDGF1, DPPA4, DNMT3B, ZIC3, and L1TD1.

When a first plasmid construct comprises more than one polynucleotides encoding reprogramming factors, the adjacent polynucleotides are operatively connected by a linker sequence encoding a self-cleaving peptide or an IRES. The self-cleaving peptide may be a 2A peptide. The 2A peptides may be derived from FMDV (foot-and-mouth disease virus), ERAV (equine rhinitis A virus), PTV-1 (porcine tescho virus-1), or TaV (thosea asigna virus), which are referred to as F2A, E2A, P2A and T2A, respectively. The multiple 2A peptides in a first plasmid construct may be the same or different. In some embodiments, two closest neighboring 2A peptides are different, for example: RF-2A1-RF-2A2-RF-2A1, where 2A1 and 2A2 are different.

A library of first plasmid construct can be pre-constructed, with each construct containing one or more polynucleotides that encode various number, type and/or combinations of reprogramming factors. Reprogramming is known to be an inefficient and stochastic process with long latency. The timing and levels of expression, and the stoichiometry of reprogramming factors drive reprogramming kinetics in different phases of reprogramming and intermediate states of the cells undergoing reprogramming and determine the completion of reprogramming. Reprogramming factor stoichiometry also affects reprogramming efficiency, and produces iPSCs with varied quality, such as primed versus ground state pluripotency, and related biological properties including clonality, self-renewal, homogeneity, and pluripotency maintenance (as opposed to spontaneous differentiation) of the iPSCs. Stoichiometry measures the quantitative relationships between reagents in a reaction process, and is used to determine the amount of reagents that are needed in a given reaction, and sometimes the amount of products produced. Stoichiometry considers both stoichiometric amount of a reagent or stoichiometric ratio of reagents, which is the optimum amount or ratio of reagent(s) to complete the reaction. One aspect of the application provides a system and method to evaluate or utilize reprogramming factor stoichiometry by allowing one or more first plasmids to be conveniently selected from the library, mix-and-matched, dosage-adjusted, and co-transfected.

The second plasmid of the present reprogramming system provides an expression cassette comprising a promoter and an EBNA encoding polynucleotide, wherein neither the expression cassette nor the second plasmid comprises any polynucleotide encoding reprogramming factors. The promoter comprised in the second plasmid may be, for example, CMV, EF1α, PGK, CAG, UBC, and other suitable promoters that are constitutive, inducible, endogenously regulated, or temporal-, tissue- or cell type-specific. In one embodiment, the promoter is CAG In another embodiment, the promoter is EF1α. By co-transfecting a non-pluripotent cell with the above described combination of at least one first plasmid and a second plasmid, the stand-alone EBNA and oriP, along with at least one reprogramming factor, are introduced to the non-pluripotent cells to initiate reprogramming.

In some embodiment, the reprogramming is initiated in the presence of a combination of small molecule compounds comprising a TGFβ receptor/ALK inhibitor, a MEK inhibitor, a GSK3 inhibitor and a ROCK inhibitor, and iPSCs are generated after a sufficient period of time. In some embodiments, the reprogramming is under a feeder-free condition. In particular embodiments, the feeder-free environment is essentially free of human feeder cells and is not pre-conditioned by feeder cells, including without limitation, mouse embryonic fibroblasts, human fibroblasts, keratinocytes, and embryonic stem cells.

In some embodiment, the cells after being induced for about 7 to 35, 10 to 32, 15 to 31 days, about 17 to 29 days, about 19 to 27 days, or about 21 to about 25 days are optionally subject to disassociation, such that the cells are dissociated into a single cell suspension, either by enzymatic or mechanical means. The dissociated cells may be resuspended in any suitable solution or media for maintaining cells or performing cell sorting. In some embodiments, the single dissociated cell suspension comprises a ROCK inhibitor. In some other embodiments, the single dissociated cell suspension comprises a GSK3 inhibitor, a MEK inhibitor and a ROCK inhibitor. In particular embodiments, the single cell suspension contains a GSK3 inhibitor, a MEK inhibitor, and a Rock inhibitor and lacks a TFGβ inhibitor. In certain embodiments, the GSK3 inhibitor is CHIR99021, the MEK inhibitor is PD0325901, and/or the Rock inhibitor is thiazovivin.

In some embodiments, the single dissociated cell suspension may be further sorted. In one embodiment, enrichment provides a method for deriving clonal iPSC colonies in a relatively short time, thereby improving the efficiency of iPSC generation. Enrichment may comprise sorting a population of cells by identifying and obtaining cells expressing markers of pluripotency, thereby obtaining a population of enriched pluripotent cells. An additional enrichment methodology comprises the depletion of cells expressing markers of differentiation, non-reprogrammed or non-pluripotent cells. In some embodiments, the cells for sorting are pluripotent cells. In some embodiments, the cells for sorting are reprogramming cells. In some embodiments, the cells for sorting have been induced to reprogram for at least 1, 2, 3, 4, 5, 6, 7, 8 or more days, but no more than 25, 26, 28, 30, 32, 35, 40 days, or any number of days in between. In some embodiment, the cells for sorting have been induced to reprogram for about 21 to 25 days, about 19 to 23 days, about 17 to 21 days, about 15 to about 19, or about 16 to about 18 days.

Cells may be sorted by any suitable method of sorting cells, such as by magnetic bead or flow cytometry (FACS) sorting. Cells may be sorted based on one or more markers of pluripotency, including without limitation, expression of SSEA3/4, TRA1-60/81, TRA1-85, TRA2-54, GCTM-2, TG343, TG30, CD9, CD29, CD133/prominin, CD140a, CD56, CD73, CD105, OCT4, NANOG, SOX2, KLF4, SSEA1 (Mouse), CD30, SSEA5, CD90 and/or CD50. In various embodiments, cells are sorted based on at least two, at least three, or at least four markers of pluripotency. In certain embodiments, cells are sorted based on expression of SSEA4, and in certain particular embodiments based on expression of SSEA4 in combination with TRA1-81 and/or TRA1-60. In certain embodiments, cells are sorted based on SSEA4, TRA1-81, or TRA1-60, and/or CD30 expression. In one embodiment, cells are sorted based on SSEA4, TRA1-81 and CD30. In another embodiment, cells are sorted based on SSEA4, TRA1-60 and CD30. In certain embodiments, cells are initially depleted for non-reprogrammed cells using one or more surface markers of differentiating cells including, but not limited to, CD13, CD26, CD34, CD45, CD31, CD46 and CD7, and then enriched for pluripotent markers such as SSEA4, TRA1-81 and/or CD30.

After reprogramming, the iPSCs are maintained, passaged and expanded. In some embodiments, the iPSCs are cultured, i.e., maintained, passaged and expanded, as single cells for an extended period in the maintenance medium, for example, the FMM as shown in Table 1. The iPSCs cultured in FMM have been shown to continue to maintain their undifferentiated, and ground or naïve, profile; genomic stability without the need for culture cleaning or selection; and are readily to give rise to all three somatic lineages, in vitro differentiation via embryoid bodies or monolayer (without formation of embryoid bodies); and in vivo differentiation by teratoma formation. See, for example, U.S. Application No. 61/947,979 and U.S. Patent Application Publication No. 20170073643, the disclosure of which is incorporated herein by reference. The cells suitable for reprogramming using the present reprogramming system and method generally include any non-pluripotent cells. Non-pluripotent cells include, but are not limited to, terminally differentiated cells; or multipotent or progenitor cells, which are not able to give rise to all three types of germ layer lineage cells. In some embodiments, the non-pluripotent cell for reprogramming is a primary cell, i.e., a cell isolated directly from human or animal tissue. In some embodiments, the non-pluripotent cell for reprogramming is a source specific cell, for example, donor-, disease-, or treatment response-specific. In some embodiments, the non-pluripotent cell for reprogramming is a primary immune cell. In some embodiments, the non-pluripotent cell for reprogramming is itself derived from a pluripotent cell, including embryonic stem cell and induced pluripotent stem cell. In some embodiments, the non-pluripotent cell for reprogramming is a derived immune cell, for example, an iPSC-derived non-natural T- or NK-like cell.

In some other embodiments, the non-pluripotent cell for reprogramming is a genomically modified primary or derived cell. The genetic modification comprised in the non-pluripotent cell include insertion, deletion or substitution in the genome, which leads to knock-in, knock-out or knock-down of a gene expression. The modified expression in the non-pluripotent cell for reprogramming may be constitutive or inducible (for example, development stage-, tissue-, cell-, or inducer-specific). In some embodiments, the insertion or substitution is a locus specific targeted integration. In some embodiments, the selected locus for integration is a safe harbor locus or an endogenous gene locus of interest. Safe harbor loci may include AAVS1, CCR5, ROSA26, collagen, HTRP, H11, beta-2 microglobulin, GAPDH, TCR or RUNX1, and other loci meeting the criteria of a genome safe harbor. For an integration site to be a potential safe harbor locus, it ideally needs to meet criteria including, but not limited to: absence of disruption of regulatory elements or genes, as judged by sequence annotation; is an intergenic region in a gene dense area, or a location at the convergence between two genes transcribed in opposite directions; keep distance to minimize the possibility of long-range interactions between vector-encoded transcriptional activators and the promoters of adjacent genes, particularly cancer-related and microRNA genes; and has apparently ubiquitous transcriptional activity, as reflected by broad spatial and temporal expressed sequence tag (EST) expression patterns, indicating ubiquitous transcriptional activity. This latter feature is especially important with regard to pluripotent cells, where during differentiation, chromatin remodeling typically leads to silencing of some loci and potential activation of others. Within the region suitable for exogenous insertion, a precise locus chosen for insertion should be devoid of repetitive elements and conserved sequences and to which primers for amplification of homology arms could easily be designed. In one example, the non-pluripotent cell for reprogramming using the present system and method is a T cell comprising a CAR at the endogenous TCR locus, and the TCR expression is disrupted as a result of the CAR integration.

In one embodiment, reprogramming of a genetically modified non-pluripotent cell is to obtain a genome engineered iPSC comprising the same genetic modification(s). As such, in some other embodiments, one or more such genomic editing may be introduced to the iPSC after reprogramming to obtain a genome-engineered iPSC. In one embodiment, the iPSC for genomic editing is a clonal line or a population of clonal iPS cells.

In some embodiments, the genome-engineered iPSCs comprising one or more targeted genetic editing are maintained, passaged and expanded in a medium comprising MEKi, GSKi, and ROCKi, and free of, or essentially free of, TGFβ receptor/ALK5 inhibitors, wherein the iPSCs retain the intact and functional targeted editing at the selected sites. In some embodiments, the genetic editing introduces one or more of a safety switch protein, a targeting modality, a receptor, a signaling molecule, a transcription factor, a pharmaceutically active protein or peptide, a drug target candidate, and a protein promoting engraftment, trafficking, homing, tumor infiltration, viability, self-renewal, persistence, and/or survival of the pluripotent cell and/or derivative cells thereof. In one embodiment, the genome engineered iPSC comprises one or more suicide gene mediated safety switch including, without limitation, caspase 9 (or caspase 3 or 7), thymidine kinase, cytosine deaminase, B-cell CD20, modified EGFR, and any combination thereof. In some embodiments, the genomically engineered iPSCs have at least one genomic modification comprising introduced or increased expression of a chimeric receptor, a homing receptor, an anti-inflammatory molecule, an immune checkpoint protein, a cytokine/chemokine decoy receptor, a growth factor, an altered pro-inflammatory cytokine receptor, a CAR, or a surface triggering receptor for coupling with bi- or multi-specific or universal engagers; or reduced or silenced expression of a co-stimulatory gene. In some embodiments, the genome-engineered iPSCs comprise a high affinity and/or non-cleavable CD16 as a targeting modality. In some other embodiments, the targeting modality comprised in the genome-engineered iPSCs is a chimeric antigen receptor (CAR) that is T cell specific, or NK cell specific, or compatible to both T and NK cells.

In some embodiments, the genome-engineered iPSC comprises one or more exogenous polynucleotides or in/dels in one or more endogenous genes. In some embodiments, the in/del comprised in an endogenous gene results in disruption of gene expression. In some embodiments, the in/del comprised in an endogenous gene results in knock-out of the edited gene. In some embodiment, the in/del comprised in an endogenous gene results in knock-down of the edited gene. In some embodiments, the genome-engineered iPSC comprising one or more exogenous polynucleotides at selected site(s) may further comprise one or more targeted editing including in/dels at selected site(s). In some embodiments, the in/del is comprised in one or more endogenous genes associated with immune response regulation and mediation. In some embodiments, the in/del is comprised in one or more endogenous check point genes. In some embodiments, the in/del is comprised in one or more endogenous T cell receptor genes. In some embodiments, the in/del is comprised in one or more endogenous MHC class I suppressor genes. In some embodiments, the in/del is comprised in one or more endogenous genes associated with the major histocompatibility complex. In one embodiment, the modified iPS cells comprise a deletion or reduced expression in at least one of B2M, TAP1, TAP2, Tapasin, NLRC5, RFXANK, CIITA, RFX5, RFXAP, and any of the HLA genes in the chromosome 6p21 region. In another embodiment, the modified iPS cells comprise an introduced or increased expression of HLA-E or HLA-G In yet some other embodiments, the genome-engineered iPS cells comprise an interrupted TCR locus.

The various targeted genetic editing methods of iPSCs, especially for effectively engineer iPSC at a single cell level with multi-gene at multi-loci targeting strategies include those depicted in, for example, International Application Publication WO 2017/079673, the disclosure of which is incorporated herein by reference.

The present invention also provides methods for identifying an agent that reprograms somatic cells to a less-differentiated state, as well as the agents thus identified. In one embodiment, the methods comprise reprogramming somatic cells using the reprogramming compositions and methods as disclosed herein, wherein at least one vector comprises a candidate agent; selecting for cells having appearance of pluripotency cell morphology and the induced expression of at least one endogenous pluripotency genes such as OCT4. The presence of cells that express the appropriate selectable marker indicates that the agent reprograms somatic cells. Such an agent is deemed as a reprogramming agent for purpose of this application. In a further embodiment, the methods comprise contacting the somatic cells with a candidate agent using the reprogramming compositions and methods as disclosed herein, selecting for cells that express the appropriate selectable marker, and assessing the cells so selected for pluripotency characteristics. The presence of a complete set of pluripotency characteristics indicates that the agent reprograms somatic cells to become pluripotent. Candidate agents used in the invention encompass numerous chemical classes, though typically they are organic molecules, including small organic compounds. Candidate agents are also found among biomolecules including peptides, saccharides, fatty acids, steroids, purines, pyrimidines, nucleic acids and derivatives, structural analogs or combinations thereof. Candidate agents may be naturally arising, recombinant or designed in the laboratory. The candidate agents may be isolated from microorganisms, animals, or plants, or may be produced recombinantly, or synthesized by chemical methods known in the art. In some embodiments, candidate agents are isolated from libraries of synthetic or natural compounds using the methods of the present invention. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, including acylation, alkylation, esterification, amidification, to produce structural analogs. There are numerous commercially available compound libraries, including, for example, the ChemBridge DIVERSet™.

The screening methods mentioned above are based on assays performed on cells. These cell-based assays may be performed in a high throughput screening (HTS) format, which has been described in the art. For example, Stockwell et al. described a high-throughput screening of small molecules in miniaturized mammalian cell-based assays involving post-translational modifications (Stockwell et al., 1999). Likewise, Qian et al. described a leukemia cell-based assay for high-throughput screening for anti-cancer agents (Qian et alt, 2001). Both references are incorporated herein in their entirety.

II. iPSC Derivative Cells Obtained In Vitro

The present invention further provides, in some embodiments, non-pluripotent cells derived from the iPSCs obtained using the system and methods as disclosed herein. In some embodiments, the iPSCs for generating derivative non-pluripotent cells are genome-engineered, either through targeted editing of iPSCs, or through reprogramming genome-engineered non-pluripotent cells having site specific integration or in/dels. In some embodiments, the iPSC-derived non-pluripotent cells are progenitor cells or fully-differentiated cells. In some embodiments, the iPSC-derived cells retaining the same targeted editing comprised in the genome-engineered iPSC are non-natural mesodermal cells, CD34 cells, hemogenic endothelium cells, hematopoietic stem or progenitor cells, hematopoietic multipotent progenitor cells, T cell progenitor, NK cell progenitor, T cells, NKT cells, NK cells, B cells, immune regulatory cells or any desired cell of any germ layer lineage. In some embodiments, the iPSC-derived non-natural immune regulatory cells comprise myeloid-derived suppressor cells (MDSCs), regulatory macrophages, regulatory dendritic cells or mesenchymal stromal cells, which are potent immune regulators of NK, B, and T cell.

In addition to producing unlimited number of cells of a certain type or subtype that are hard to come by through isolation from donor sources, it has been shown that human iPSC derived lineages exhibit the properties of fetal-stage cells, such that the reprogramming process resets not only cell fate (from specified/differentiated to pluripotent) but also the chronological age characteristic of the donor cell population independent of the age of the initial somatic cell donor. Other than fetal-like properties observed in iPSC-derived lineages including neural, cardiac, or pancreatic cells, cellular hallmarks of aging have shown measurable changes indicative of rejuvenation of redifferentiated cells from iPSC following the reprogramming process. Age-related parameters expressed in the aged donor fibroblast population were reset after iPSC induction and differentiation into iPSC-derived fibroblast-like cells (Miller et al., 2013). iPSC-derived antigen-specific T cells differentiated from iPSCs reprogrammed from a T-cell clone demonstrate rejuvenation through elongated telomeres than those in the original T cell clone. Additional changes in fully differentiated cells indicative of a rejuvenation process include, but are not limited to, global increase of heterochromatin, improved mitochondrial function (ROS reduction, reduced mtDNA mutation, presence of ultrastructure), increased DNA damage responses, telomere elongation and decrease of percentage of short telomere, and decrease in the fraction of senescent cells. (Nishimura et al., 2013). The positive reset in these various age-related aspects lead to a non-natural cell having a higher potential for proliferation, survival, persistence, and memory like functions. Hence, the reprogramming and redifferentiation mediated rejuvenation imparts many molecular, phenotypic and functional properties in a fully differentiated iPSC-derived cell, which non-natural properties set it apart from its primary-cell counterpart despite their likeness in cell lineage.

Applicable differentiation methods and compositions for obtaining iPSC-derived hematopoietic cell lineages include those depicted in, for example, International Application No. PCT/US2016/044122, the disclosure of which is incorporated herein by reference. As provided, the methods and compositions for generating hematopoietic cell lineages are through definitive hemogenic endothelium (HE) derived from pluripotent stem cells, including iPSCs under serum-free, feeder-free, and/or stromal-free conditions and in a scalable and monolayer culturing platform without the need of EB formation. Cells that may be differentiated according to the provided methods range from pluripotent stem cells, to progenitor cells that are committed to a particular terminally differentiated cell and transdifferentiated cells, cells of various lineages directly transitioned to hematopoietic fate without going through a pluripotent intermediate. Similarly, the cells produced by differentiation of stem cells range from multipotent stem or progenitor cells to terminally differentiated stem cells, and all intervening hematopoietic cell lineages.

The methods for differentiating and expanding cells of the hematopoietic lineage from pluripotent stem cells in monolayer culturing comprise contacting the pluripotent stem cells with a BMP pathway activator, and optionally, bFGF. As provided, the pluripotent stem cell-derived mesodermal cells are obtained and expanded without forming embryoid bodies from pluripotent stem cells. The mesodermal cells are then subjected to contact with a BMP pathway activator, bFGF, and a WNT pathway activator to obtain expanded mesodermal cells having definitive hemogenic endothelium (HE) potential without forming embryoid bodies from the pluripotent stem cells. By subsequent contact with bFGF, and optionally, a ROCK inhibitor, and/or a WNT pathway activator, the mesodermal cells having definitive HE potential are differentiated to definitive HE cells, which are also expanded during differentiation.

The methods provided herein for obtaining cells of the hematopoietic lineage are superior to EB-mediated pluripotent stem cell differentiation, because EB formation leads to modest to minimal cell expansion, does not allow monolayer culturing which is important for many applications requiring homogeneous expansion, and homogeneous differentiation of the cells in a population, and is laborious and low efficiency.

The provided monolayer differentiation platform facilitates differentiation towards definitive hemogenic endothelium resulting in the derivation of hematopoietic stem cells and differentiated progeny such as T, B, NKT, NK cells, and regulatory cells. The monolayer differentiation strategy combines enhanced differentiation efficiency with large-scale expansion enables the delivery of therapeutically relevant number of pluripotent stem cell-derived hematopoietic cells for various therapeutic applications. Further, the monolayer culturing using the methods provided herein leads to functional hematopoietic lineage cells that enable full range of in vitro differentiation, ex vivo modulation, and in vivo long term hematopoietic self-renewal, reconstitution and engraftment. As provided, the iPSC derived hematopoietic lineage cells include, but not limited to, definitive hemogenic endothelium, hematopoietic multipotent progenitor cells, hematopoietic stem and progenitor cells, T cell progenitors, NK cell progenitors, T cells, NK cells, NKT cells, B cells, macrophages, neutrophils, myeloid-derived suppressor cells (MDSCs), regulatory macrophages, regulatory dendritic cells, and mesenchymal stromal cells.

The method for directing differentiation of pluripotent stem cells into cells of a definitive hematopoietic lineage, wherein the method comprises: (i) contacting pluripotent stem cells with a composition comprising a BMP activator, and optionally bFGF, to initiate differentiation and expansion of mesodermal cells from the pluripotent stem cells; (ii) contacting the mesodermal cells with a composition comprising a BMP activator, bFGF, and a GSK3 inhibitor, wherein the composition is optionally free of TGFβ receptor/ALK inhibitor, to initiate differentiation and expansion of mesodermal cells having definitive HE potential from the mesodermal cells; (iii) contacting the mesodermal cells having definitive HE potential with a composition comprising a ROCK inhibitor; one or more growth factors and cytokines selected from the group consisting of bFGF, VEGF, SCF, IGF, EPO, IL6, and IL11; and optionally, a Wnt pathway activator, wherein the composition is optionally free of TGFβ receptor/ALK inhibitor, to initiate differentiation and expansion of definitive hemogenic endothelium from pluripotent stem cell-derived mesodermal cells having definitive hemogenic endothelium potential.

In some embodiments, the method further comprises contacting pluripotent stem cells with a composition comprising a MEK inhibitor, a GSK3 inhibitor, and a ROCK inhibitor, wherein the composition is free of TGFβ receptor/ALK inhibitors, to seed and expand the pluripotent stem cells. In some embodiments, the pluripotent stem cells are iPSCs, or naïve iPSCs, or iPSCs comprising one or more genetic imprints; and the one or more genetic imprints comprised in the iPSC are retained in the hematopoietic cells differentiated therefrom. In some embodiments of the method for directing differentiation of pluripotent stem cells into cells of a hematopoietic lineage, the differentiation of the pluripotent stem cells into cells of hematopoietic lineage is void of generation of embryoid bodies, and is in a monolayer culturing form.

In some embodiments of the above method, the obtained pluripotent stem cell-derived definitive hemogenic endothelium cells are CD34+. In some embodiments, the obtained definitive hemogenic endothelium cells are CD34+CD43−. In some embodiments, the definitive hemogenic endothelium cells are CD34+CD43−CXCR4−CD73−. In some embodiments, the definitive hemogenic endothelium cells are CD34+ CXCR4−CD73−. In some embodiments, the definitive hemogenic endothelium cells are CD34+CD43−CD93−. In some embodiments, the definitive hemogenic endothelium cells are CD34+CD93−. In some embodiments, the definitive hemogenic endothelium cells are CD34+ CD93−CD73−.

In some embodiments of the above method, the method further comprises (i) contacting pluripotent stem cell-derived definitive hemogenic endothelium with a composition comprising a ROCK inhibitor; one or more growth factors and cytokines selected from the group consisting of VEGF, bFGF, SCF, Flt3L, TPO, and IL7; and optionally a BMP activator; to initiate the differentiation of the definitive hemogenic endothelium to pre-T cell progenitors; and optionally, (ii) contacting the pre-T cell progenitors with a composition comprising one or more growth factors and cytokines selected from the group consisting of SCF, Flt3L, and IL7, but free of one or more of VEGF, bFGF, TPO, BMP activators and ROCK inhibitors, to initiate the differentiation of the pre-T cell progenitors to T cell progenitors or T cells. In some embodiments of the method, the pluripotent stem cell-derived T cell progenitors are CD34+CD45+CD7+. In some embodiments of the method, the pluripotent stem cell-derived T cell progenitors are CD45+CD7+. In some embodiments, the pluripotent stem cell-derived T cell comprise a fraction of γδT cells much higher than primary T cells isolated from donor sources.

In yet some embodiments of the above method for directing differentiation of pluripotent stem cells into cells of a hematopoietic lineage, the method further comprises: (i) contacting pluripotent stem cell-derived definitive hemogenic endothelium with a composition comprising a ROCK inhibitor; one or more growth factors and cytokines selected from the group consisting of VEGF, bFGF, SCF, Flt3L, TPO, IL3, IL7, and IL15; and optionally, a BMP activator, to initiate differentiation of the definitive hemogenic endothelium to pre-NK cell progenitor; and optionally, (ii) contacting pluripotent stem cells-derived pre-NK cell progenitors with a composition comprising one or more growth factors and cytokines selected from the group consisting of SCF, Flt3L, IL3, IL7, and IL15, wherein the medium is free of one or more of VEGF, bFGF, TPO, BMP activators and ROCK inhibitors, to initiate differentiation of the pre-NK cell progenitors to NK cell progenitors or NK cells. In some embodiments, the pluripotent stem cell-derived NK progenitors are CD3−CD45+CD56+CD7+. In some embodiments, the pluripotent stem cell-derived NK cells are CD3−CD45+CD56+. In some embodiments, the pluripotent stem cell-derived NK cells are optionally further defined by one or more of NKp46 (CD335), NKp30 (CD337), DNAM-1 (CD226), 2B4 (CD244), CD57 and CD16.

In another embodiment of the method, the method enables producing immune regulatory cells from contacting pluripotent stem cell-derived definitive HE with a medium comprising a ROCK inhibitor, MCSF, GMCSF, and one or more growth factors and cytokines selected from the group consisting of IL1b, IL3, IL6, IL4, IL10, IL13, TGFβ, bFGF, VEGF, SCF, and FLT3L, and optionally, one or both of an AhR antagonist and a prostaglandin pathway agonist.

In some embodiments, the derived immune regulatory cells comprise myeloid derived suppressor cells (MDSCs). In one embodiment, the population of derived immune regulatory cells comprises CD45+CD33+ cells. In some embodiments, the population of derived immune regulatory cells comprise monocytes. In some embodiments, the monocytes comprise CD45+CD33+CD14+ cells. In yet some other embodiments, the population of derived immune regulatory cells comprise CD45+CD33+PDL1+ cells. One aspect of this invention provides an enriched cell population or subpopulation of iPSC-derived immune regulatory cells comprising CD45+CD33+, CD45+CD33+CD14+, or CD45+CD33+PDL1+ cells. In some other embodiments, the population of derived immune regulatory cells comprise CD33+CD15+CD14−CD11b− cells. In some embodiments, the population of derived immune regulatory cells comprising iMDSCs comprise less than 50%, 40%, 30%, 20%, 10%, 5%, 2%, 1%, 0.1% of erythrocytes, lymphoid, granulocytes, CD45−CD235+ cells, CD45+CD7+ cells, or CD45+CD33+CD66b+ cells. In some embodiments, the population of derived immune regulatory cells is essentially free of erythrocytes, lymphoid, granulocytes, CD45−CD235+ cells, CD45+CD7+ cells, or CD45+CD33+CD66b+ cells.

III. Therapeutic Use of iPSCs and Derivative Immune Cells Therefrom

The present invention provides, in some embodiments, a composition comprising an isolated population or subpopulation of iPSCs and/or immune cells that have been derived from said iPSC using the methods and compositions as disclosed. In some embodiments, the iPSCs comprise one or more targeted genetic editing which are retainable in the iPSC-derived immune cells, wherein the genetically engineered iPSCs and derivative cells thereof are suitable for cell based adoptive therapies. In one embodiment, the isolated population or subpopulation of genetically engineered immune cell comprises iPSC derived HSC cells. In one embodiment, the isolated population or subpopulation of genetically engineered immune cell comprises iPSC derived HSC cells. In one embodiment, the isolated population or subpopulation of genetically engineered immune cell comprises iPSC derived proT or T cells. In one embodiment, the isolated population or subpopulation of genetically engineered immune cell comprises iPSC derived proNK or NK cells. In one embodiment, the isolated population or subpopulation of genetically engineered immune cell comprises iPSC derived immune regulatory cells or myeloid derived suppressor cells (MDSCs). In some embodiments, the iPSC derived genetically engineered immune cells are further modulated ex vivo for improved therapeutic potential. In one embodiment, an isolated population or subpopulation of genetically engineered immune cells that have been derived from iPSC comprises an increased number or ratio of naïve T cells, stem cell memory T cells, and/or central memory T cells. In one embodiment, the isolated population or subpopulation of genetically engineered immune cell that have been derived from iPSC comprises an increased number or ratio of type I NKT cells. In another embodiment, the isolated population or subpopulation of genetically engineered immune cell that have been derived from iPSC comprises an increased number or ratio of adaptive NK cells. In some embodiments, the isolated population or subpopulation of genetically engineered CD34 cells, HSC cells, T cells, NK cells, or myeloid derived suppressor cells derived from iPSC are allogeneic. In some other embodiments, the isolated population or subpopulation of genetically engineered CD34 cells, HSC cells, T cells, NK cells, or MDSC derived from iPSC are autogenic.

In some embodiments, the iPSC for differentiation comprises genetic imprints conveying desirable therapeutic attributes in effector cells, which genetic imprints are retained and functional in the differentiated hematopoietic cells derived from said iPSC.

In some embodiments, the genetic imprints of the pluripotent stem cells comprise (i) one or more genetically modified modalities obtained through genomic insertion, deletion or substitution in the genome of the pluripotent cells during or after reprogramming a non-pluripotent cell to iPSC; or (ii) one or more retainable therapeutic attributes of a source specific immune cell that is donor-, disease-, or treatment response-specific, and wherein the pluripotent cells are reprogrammed from the source specific immune cell, wherein the iPSC retain the source therapeutic attributes, which are also comprised in the iPSC derived hematopoietic lineage cells.

In some embodiments, the genetically modified modalities comprise one or more of: safety switch proteins, targeting modalities, receptors, signaling molecules, transcription factors, pharmaceutically active proteins and peptides, drug target candidates; or proteins promoting engraftment, trafficking, homing, viability, self-renewal, persistence, immune response regulation and modulation, and/or survival of the iPSCs or derivative cells thereof. In some other embodiments, the genetically modified modalities comprise one or more of (i) deletion or reduced expression of B2M, TAP1, TAP2, Tapasin, NLRC5, PD1, LAG3, TIM3, RFXANK, CIITA, RFX5, or RFXAP, and any gene in the chromosome 6p21 region; (ii) introduced or increased expression of HLA-E, HLA-G, HACD16, 41BBL, CD3, CD4, CD8, CD47, CD113, CD131, CD137, CD80, PDL1, A2AR, CAR, TCR, Fc receptor, or surface triggering receptors for coupling with bi- or multi-specific or universal engagers.

In still some other embodiments, the hematopoietic lineage cells comprise the therapeutic attributes of the source specific immune cell relating to one or more of (i) antigen targeting receptor expression; (ii) HLA presentation or lack thereof; (iii) resistance to tumor microenvironment; (iv) induction of bystander immune cells and immune modulations; (iv) improved on-target specificity with reduced off-tumor effect; (v) resistance to treatment such as chemotherapy; and (vi) improved homing, persistence, and cytotoxicity.

In some embodiments, the iPSC and its derivative hematopoietic cells comprise one or more of B2M null or low, HLA-E/Q PDL1, A2AR, CD47, LAG3 null or low, TIM3 null or low, TAP1 null or low, TAP2 null or low, Tapasin null or low, NLRC5 null or low, PD1 null or low, RFKANK null or low, CIITA null or low, RFX5 null or low and RFXAP null or low. These cells with modified HLA class I and/or II have increased resistance to immune detection, and therefore present improved in vivo persistence. Moreover, such cells can avoid the need for HLA matching in adoptive cell therapy and thus provide a source of universal, off-the-shelf therapeutic regimen.

In some embodiments, the iPSC and its derivative hematopoietic cells comprise one or more of hnCD16 (high-affinity non-cleavable CD16), HLA-E, HLA-Q 41BBL, CD3, CD4, CD8, CD47, CD113, CD131, CD137, CD80, PDL1, A2AR, CAR, or TCR. Such cells have improved immune effector ability.

In some embodiments, the iPSC and its derivative hematopoietic cells are antigen specific.

A variety of diseases may be ameliorated by introducing the immune cells of the invention to a subject suitable for adoptive cell therapy. Examples of diseases including various autoimmune disorders, including but not limited to, alopecia areata, autoimmune hemolytic anemia, autoimmune hepatitis, dermatomyositis, diabetes (type 1), some forms of juvenile idiopathic arthritis, glomerulonephritis, Graves' disease, Guillain-Barré syndrome, idiopathic thrombocytopenic purpura, myasthenia gravis, some forms of myocarditis, multiple sclerosis, pemphigus/pemphigoid, pernicious anemia, polyarteritis nodosa, polymyositis, primary biliary cirrhosis, psoriasis, rheumatoid arthritis, scleroderma/systemic sclerosis, Sjögren's syndrome, systemic lupus, erythematosus, some forms of thyroiditis, some forms of uveitis, vitiligo, granulomatosis with polyangiitis (Wegener's); hematological malignancies, including but not limited to, acute and chronic leukemias, lymphomas, multiple myeloma and myelodysplastic syndromes; solid tumors, including but not limited to, tumor of the brain, prostate, breast, lung, colon, uterus, skin, liver, bone, pancreas, ovary, testes, bladder, kidney, head, neck, stomach, cervix, rectum, larynx, or esophagus; and infections, including but not limited to, HIV- (human immunodeficiency virus), RSV- (Respiratory Syncytial Virus), EBV- (Epstein-Barr virus), CMV- (cytomegalovirus), adenovirus- and BK polyomavirus-associated disorders.

According to some embodiments, the present invention further provides compositions for therapeutic use comprising the pluripotent cell derived hematopoietic lineage cells made by the methods and composition disclosed herein, wherein the pharmaceutical compositions further comprise a pharmaceutically acceptable medium. In one embodiment, the composition for therapeutic use comprises the pluripotent cell derived T cells made by the methods and composition disclosed herein. In one embodiment, the composition for therapeutic use comprises the pluripotent cell derived NK cells made by the methods and composition disclosed herein. In one embodiment, the composition for therapeutic use comprises the pluripotent cell derived CD34+HE cells made by the methods and composition disclosed herein. In one embodiment, the composition for therapeutic use comprises the pluripotent cell derived HSCs made by the methods and composition disclosed herein. In one embodiment, the composition for therapeutic use comprises the pluripotent cell derived MDSC made by the methods and composition disclosed herein.

Additionally, the present invention provides, in some embodiments, therapeutic use of the above therapeutic compositions by introducing the composition to a subject suitable for adoptive cell therapy, wherein the subject has an autoimmune disorder; a hematological malignancy; a solid tumor; or an infection associated with HIV, RSV, EBV, CMV, adenovirus, or BK polyomavirus.

The isolated pluripotent stem cell derived hematopoietic lineage cells can have at least 50%, 60%, 70%, 80%, 90%, 95%, 98%, or 99% T cells, NK cells, NKT cells, proT cells, proNK cells, CD34+HE cells, HSCs, B cells, myeloid-derived suppressor cells (MDSCs), regulatory macrophages, regulatory dendritic cells or mesenchymal stromal cells. In some embodiments, the isolated pluripotent stem cell derived hematopoietic lineage cells has about 95% to about 100% T cells, NK cells, NKT cells, proT cells, proNK cells, CD34+HE cells, HSCs, B cells, myeloid-derived suppressor cells (MDSCs), regulatory macrophages, regulatory dendritic cells or mesenchymal stromal cells. In some embodiments, the present invention provides therapeutic compositions having purified T cells, NK cells, NKT cells, CD34+ HE cells, proT cells, proNK cells, HSCs, B cells, myeloid-derived suppressor cells (MDSCs), regulatory macrophages, regulatory dendritic cells, or mesenchymal stromal cells, such as a composition having an isolated population of about 95% T cells, NK cells, NKT cells, proT cells, proNK cells, CD34+HE cells, HSCs, B cells, myeloid-derived suppressor cells (MDSCs), regulatory macrophages, regulatory dendritic cells or mesenchymal stromal cells to treat a subject in need of the cell therapy.

The treatment using the derived hematopoietic lineage cells of embodiments disclosed herein could be carried out upon symptom, or for relapse prevention. The terms "treating," "treatment," and the like are used herein to generally mean obtaining a desired pharmacologic and/or physiologic effect. The effect may be prophylactic in terms of completely or partially preventing a disease and/or may be therapeutic in terms of a partial or complete cure for a disease and/or adverse effect attributable to the disease. "Treatment" as used herein covers any treatment of a disease in a mammal, and includes: preventing the disease from occurring in a subject which may be predisposed to the disease but has not yet been diagnosed as having it; inhibiting the disease, i.e., arresting its development; or relieving the disease, i.e., causing regression of the disease. The therapeutic agent or composition may be administered before, during or after the onset of a disease or an injury. The treatment of ongoing disease, where the treatment stabilizes or reduces the undesirable clinical symptoms of the patient, is also of particular interest. In particular embodiments, the subject in need of a treatment has a disease, a condition, and/or an injury that can be treated, ameliorated, and/or improved in at least one associated symptom by a cell therapy. Certain embodiments contemplate that a subject in need of cell therapy, includes, but is not limited to, a candidate for bone marrow or stem cell transplantation, a subject who has received chemotherapy or irradiation therapy, a subject who has or is at risk of having a hyperproliferative disorder or a cancer, e.g. a hyperproliferative disorder or a cancer of hematopoietic system, a subject having or at risk of developing a tumor, e.g., a solid tumor, a subject who has or is at risk of having a viral infection or a disease associated with a viral infection.

The therapeutic composition comprising derived hematopoietic lineage cells as disclosed can be administered in a subject before, during, and/or after other treatments. As such the method of a combinational therapy can involve the administration or preparation of iPSC derived immune cells before, during, and/or after the use of an additional therapeutic agent. As provided above, the one or more additional therapeutic agents comprise a peptide, a cytokine, a mitogen, a growth factor, a small RNA, a dsRNA (double stranded RNA), mononuclear blood cells, feeder cells, feeder cell components or replacement factors thereof, a vector comprising one or more polynucleic acids of interest, an antibody, a chemotherapeutic agent or a radioactive moiety, or an immunomodulatory drug (IMiD). The administration of the iPSC derived immune cells can be separated in time from the administration of an additional therapeutic agent by hours, days, or even weeks. Additionally or alternatively, the administration can be combined with other biologically active agents or modalities such as, but not limited to, an antineoplastic agent, a non-drug therapy, such as, surgery.

In some embodiments, the additional therapeutic agent comprises an antibody, or an antibody fragment. In some embodiments, the antibody is a monoclonal antibody. In some embodiments, the antibody may be a humanized antibody, a humanized monoclonal antibody, or a chimeric antibody. In some embodiments, the antibody, or antibody fragment, specifically binds to a viral antigen. In other embodiments, the antibody, or antibody fragment, specifically binds to a tumor antigen. In some embodiments, the tumor or viral specific antigen activates the administered iPSC derived hematopoietic lineage cells to enhance their killing ability. In some embodiments, the antibodies suitable for combinational treatment as an additional therapeutic agent to the administered iPSC derived hematopoietic lineage cells include, but are not limited to, anti-CD20 (retuximab, veltuzumab, ofatumumab, ublituximab, ocaratuzumab, obinutuzumab), anti-Her2 (trastuzumab), anti-CD52 (alemtuzumab), anti-EGFR (certuximab), and anti-CD38 (daratumumab, isatuximab, MOR202), and their humanized and Fc modified variants.

In some embodiments, the additional therapeutic agent comprises one or more chemotherapeutic agents or a radioactive moiety. Chemotherapeutic agent refers to cytotoxic antineoplastic agents, that is, chemical agents which preferentially kill neoplastic cells or disrupt the cell cycle of rapidly-proliferating cells, or which are found to eradicate stem cancer cells, and which are used therapeutically to prevent or reduce the growth of neoplastic cells. Chemotherapeutic agents are also sometimes referred to as antineoplastic or cytotoxic drugs or agents, and are well known in the art.

In some embodiments, the chemotherapeutic agent comprises an anthracycline, an alkylating agent, an alkyl sulfonate, an aziridine, an ethylenimine, a methylmelamine, a nitrogen mustard, a nitrosourea, an antibiotic, an antimetabolite, a folic acid analog, a purine analog, a pyrimidine analog, an enzyme, a podophyllotoxin, a platinum-containing agent, an interferon, and an interleukin. Exemplary chemotherapeutic agents include, but are not limited to, alkylating agents (cyclophosphamide, mechlorethamine, mephalin, chlorambucil, heamethylmelamine, thiotepa, busulfan, carmustine, lomustine, semustine), animetabolites (methotrexate, fluorouracil, floxuridine, cytarabine, 6-mercaptopurine, thioguanine, pentostatin), *vinca* alkaloids (vincristine, vinblastine, vindesine), epipodophyllotoxins (etoposide, etoposide orthoquinone, and teniposide), antibiotics (daunorubicin, doxorubicin, mitoxantrone, bisanthrene, actinomycin D, plicamycin, puromycin, and gramicidine D), paclitaxel, colchicine, cytochalasin B, emetine, maytansine, and amsacrine. Additional agents include aminglutethimide, cisplatin, carboplatin, mitomycin, altretamine, cyclophosphamide, lomustine (CCNU), carmustine (BCNU), irinotecan (CPT-11), alemtuzamab, altretamine, anastrozole, L-asparaginase, azacitidine, bevacizumab, bexarotene, bleomycin, bortezomib, busulfan, calusterone, capecitabine, celecoxib, cetuximab, cladribine, clofurabine, cytarabine, dacarbazine, denileukin diftitox, diethlstilbestrol, docetaxel, dromostanolone, epirubicin, erlotinib, estramustine, etoposide, ethinyl estradiol, exemestane, floxuridine, 5-flourouracil, fludarabine, flutamide, fulvestrant, gefitinib, gemcitabine, goserelin, hydroxyurea, ibritumomab, idarubicin, ifosfamide, imatinib, interferon alpha (2a, 2b), irinotecan, letrozole, leucovorin, leuprolide, levamisole, meclorethamine, megestrol, melphalin, mercaptopurine, methotrexate, methoxsalen, mitomycin C, mitotane, mitoxantrone, nandrolone, nofetumomab, oxaliplatin, paclitaxel, pamidronate, pemetrexed, pegademase, pegasparagase, pentostatin, pipobroman, plicamycin, polifeprosan, porfimer, procarbazine, quinacrine, rituximab, sargramostim, streptozocin, tamoxifen, temozolomide, teniposide, testolactone, thioguanine, thiotepa, topetecan, toremifene, tositumomab, trastuzumab, tretinoin, uracil mustard, valrubicin, vinorelbine, and zoledronate. Other suitable agents are those that are approved for human use, including those that will be approved, as chemotherapeutics or radiotherapeutics, and known in the art. Such agents can be referenced through any of a number of standard physicians' and oncologists' references (e.g. Goodman & Gilman's The Pharmacological Basis of Therapeutics, Ninth Edition, McGraw-Hill, N.Y., 1995) or through the National Cancer Institute website (fda.gov/cder/cancer/druglistframe.htm), both as updated from time to time.

Immunomodulatory drugs (IMiDs) such as thalidomide, lenalidomide, and pomalidomide stimulate both NK cells and T cells. As provided herein, IMiDs may be used with the iPSC derived therapeutic immune cells for cancer treatments.

As a person of ordinary skill in the art would understand, both autologous and allogeneic hematopoietic lineage cells derived from iPSC based on the methods and composition herein can be used in cell therapies as described above. For autologous transplantation, the isolated population of derived hematopoietic lineage cells are either complete or partial HLA-match with the patient. In another embodiment, the derived hematopoietic lineage cells are not HLA-matched to the subject.

In some embodiments, the number of derived hematopoietic lineage cells in the therapeutic composition is at least $0.1\times10^5$ cells, at least $1\times10^5$ cells, at least $5\times10^5$ cells, at least $1\times10^6$ cells, at least $5\times10^6$ cells, at least $1\times10^7$ cells, at least $5\times10^7$ cells, at least $1\times10^8$ cells, at least $5\times10^8$ cells, at least $1\times10^9$ cells, or at least $5\times10^9$ cells, per dose. In some embodiments, the number of derived hematopoietic lineage cells in the therapeutic composition is about $0.1\times10^5$ cells to about $1\times10^6$ cells, per dose; about $0.5\times10^6$ cells to about $1\times10^7$ cells, per dose; about $0.5\times10^7$ cells to about $1\times10^8$ cells, per dose; about $0.5\times10^8$ cells to about $1\times10^9$ cells, per dose; about $1\times10^9$ cells to about $5\times10^9$ cells, per dose; about $0.5\times10^9$ cells to about $8\times10^9$ cells, per dose; about $3\times10^9$ cells to about $3\times10^{10}$ cells, per dose, or any range in-between. Generally, $1\times10^8$ cells/dose translates to $1.67\times10^6$ cells/kg for a 60 kg patient.

In one embodiment, the number of derived hematopoietic lineage cells in the therapeutic composition is the number of immune cells in a partial or single cord of blood, or is at least $0.1\times10^5$ cells/kg of bodyweight, at least $0.5\times10^5$ cells/kg of bodyweight, at least $1\times10^5$ cells/kg of bodyweight, at least $5\times10^5$ cells/kg of bodyweight, at least $10\times10^5$ cells/kg of bodyweight, at least $0.75\times10^6$ cells/kg of bodyweight, at least $1.25\times10^6$ cells/kg of bodyweight, at least $1.5\times10^6$ cells/kg of bodyweight, at least $1.75\times10^6$ cells/kg of bodyweight, at least $2\times10^6$ cells/kg of bodyweight, at least $2.5\times10^6$ cells/kg of bodyweight, at least $3\times10^6$ cells/kg of bodyweight, at least $4\times10^6$ cells/kg of bodyweight, at least $5\times10^6$ cells/kg of bodyweight, at least $10\times10^6$ cells/kg of bodyweight, at least $15\times10^6$ cells/kg of bodyweight, at least $20\times10^6$ cells/kg of bodyweight, at least $25\times10^6$ cells/kg of bodyweight, at least $30\times10^6$ cells/kg of bodyweight, $1\times10^8$ cells/kg of bodyweight, $5\times10^8$ cells/kg of bodyweight, or $1\times10^9$ cells/kg of bodyweight.

In one embodiment, a dose of derived hematopoietic lineage cells is delivered to a subject. In one illustrative embodiment, the effective amount of cells provided to a subject is at least $2\times10^6$ cells/kg, at least $3\times10^6$ cells/kg, at least $4\times10^6$ cells/kg, at least $5\times10^6$ cells/kg, at least $6\times10^6$ cells/kg, at least $7\times10^6$ cells/kg, at least $8\times10^6$ cells/kg, at least $9\times10^6$ cells/kg, or at least $10\times10^6$ cells/kg, or more cells/kg, including all intervening doses of cells.

In another illustrative embodiment, the effective amount of cells provided to a subject is about $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, or about $10\times10^6$ cells/kg, or more cells/kg, including all intervening doses of cells.

In another illustrative embodiment, the effective amount of cells provided to a subject is from about $2\times10^6$ cells/kg to about $10\times10^6$ cells/kg, about $3\times10^6$ cells/kg to about $10\times10^6$ cells/kg, about $4\times10^6$ cells/kg to about $10\times10^6$ cells/kg, about $5\times10^6$ cells/kg to about $10\times10^6$ cells/kg, $2\times10^6$ cells/kg to about $6\times10^6$ cells/kg, $2\times10^6$ cells/kg to about $7\times10^6$ cells/kg, $2\times10^6$ cells/kg to about $8\times10^6$ cells/kg, $3\times10^6$ cells/kg to about $6\times10^6$ cells/kg, $3\times10^6$ cells/kg to about $7\times10^6$ cells/kg, $3\times10^6$ cells/kg to about $8\times10^6$ cells/kg, $4\times10^6$ cells/kg to about $6\times10^6$ cells/kg, $4\times10^6$ cells/kg to about $7\times10^6$ cells/kg, $4\times10^6$ cells/kg to about $8\times10^6$ cells/kg, $5\times10^6$ cells/kg to about $6\times10^6$ cells/kg, $5\times10^6$ cells/kg to about $7\times10^6$ cells/kg, $5\times10^6$ cells/kg to about $8\times10^6$ cells/kg, or $6\times10^6$ cells/kg to about $8\times10^6$ cells/kg, including all intervening doses of cells.

Some variation in dosage will necessarily occur depending on the condition of the subject being treated. The person responsible for administration will, in any event, determine the appropriate dose for the individual subject.

In some embodiments, the therapeutic use of derived hematopoietic lineage cells is a single-dose treatment. In some embodiments, the therapeutic use of derived hematopoietic lineage cells is a multi-dose treatment. In some embodiments, the multi-dose treatment is one dose every day, every 3 days, every 7 days, every 10 days, every 15 days, every 20 days, every 25 days, every 30 days, every 35 days, every 40 days, every 45 days, or every 50 days, or any number of days in-between.

The compositions comprising a population of derived hematopoietic lineage cells of the invention can be sterile, and can be suitable and ready for administration (i.e., can be administered without any further processing) to human patients. A cell based composition that is ready for administration means that the composition does not require any further treatment or manipulations prior to transplant or administration to a subject. In other embodiments, the invention provides an isolated population of derived hematopoietic lineage cells that are expanded and/or modulated prior to administration with one or more agents. For derived hematopoietic lineage cells that genetically engineered to express recombinant TCR or CAR, the cells can be activated and expanded using methods as described, for example, in U.S. Pat. No. 6,352,694.

In certain embodiments, the primary stimulatory signal and the co-stimulatory signal for the derived hematopoietic lineage cells can be provided by different protocols. For example, the agents providing each signal can be in solution or coupled to a surface. When coupled to a surface, the agents can be coupled to the same surface (i.e., in "cis" formation) or to separate surfaces (i.e., in "trans" formation). Alternatively, one agent can be coupled to a surface and the other agent in solution. In one embodiment, the agent providing the co-stimulatory signal can be bound to a cell surface and the agent providing the primary activation signal is in solution or coupled to a surface. In certain embodiments, both agents can be in solution. In another embodiment, the agents can be in soluble form, and then cross-linked to a surface, such as a cell expressing Fc receptors or an antibody or other binding agent which will bind to the agents such as disclosed in U.S. Patent Application Publication Nos. 20040101519 and 20060034810 for artificial antigen presenting cells (aAPCs) that are contemplated for use in activating and expanding T lymphocytes in embodiments of the present invention.

The therapeutic compositions suitable for administration to a patient can include one or more pharmaceutically acceptable carriers (additives) and/or diluents (e.g., pharmaceutically acceptable medium, for example, cell culture medium), or other pharmaceutically acceptable components.

Pharmaceutically acceptable carriers and/or diluents are determined in part by the particular composition being administered, as well as by the particular method used to administer the therapeutic composition. Accordingly, there is a wide variety of suitable formulations of therapeutic compositions of the present invention (see, e.g., Remington's Pharmaceutical Sciences, 17th ed. 1985, the disclosure of which is hereby incorporated by reference in its entirety).

In particular embodiments, therapeutic cell compositions having an isolated population of iPSC derived hematopoietic lineage cells also have a pharmaceutically acceptable cell culture medium, or pharmaceutically acceptable carriers and/or diluents. A therapeutic composition comprising a population of iPSC derived hematopoietic lineage cells as disclosed herein can be administered separately by intravenous, intraperitoneal, enteral, or tracheal administration methods or in combination with other suitable compounds to effect the desired treatment goals.

These pharmaceutically acceptable carriers and/or diluents can be present in amounts sufficient to maintain a PH of the therapeutic composition of between about 3 and about 10. As such, the buffering agent can be as much as about 5% on a weight to weight basis of the total composition. Electrolytes such as, but not limited to, sodium chloride and potassium chloride can also be included in the therapeutic composition. In one aspect, the PH of the therapeutic composition is in the range from about 4 to about 10. Alternatively, the PH of the therapeutic composition is in the range from about 5 to about 9, from about 6 to about 9, or from about 6.5 to about 8. In another embodiment, the therapeutic composition includes a buffer having a PH in one of said PH ranges. In another embodiment, the therapeutic composition has a PH of about 7. Alternatively, the therapeutic composition has a PH in a range from about 6.8 to about 7.4. In still another embodiment, the therapeutic composition has a PH of about 7.4.

The invention also provides, in part, the use of a pharmaceutically acceptable cell culture medium in particular compositions and/or cultures of the present invention. Such compositions are suitable for administration to human subjects. Generally speaking, any medium that supports the maintenance, growth, and/or health of the iPSC derived immune cells in accordance with embodiments of the invention are suitable for use as a pharmaceutical cell culture medium. In particular embodiments, the pharmaceutically acceptable cell culture medium is a serum free, and/or feeder-free medium. In various embodiments, the serum-free medium is animal-free, and can optionally be protein-free. Optionally, the medium can contain biopharmaceutically acceptable recombinant proteins. Animal-free medium refers to medium wherein the components are derived from non-animal sources. Recombinant proteins replace native animal proteins in animal-free medium and the nutrients are obtained from synthetic, plant or microbial sources. Protein-free medium, in contrast, is defined as substantially free of protein. One having ordinary skill in the art would appreciate that the above examples of media are illustrative and in no way limit the formulation of media suitable for use in the present invention.

Sequence Listing

Length: 641
Type: PRT
Organism: Human herpesvirus 4
SEQ ID NO: 1
MSDEGPGTGPGNGLGEKGDTSGPEGSGGSGPQRRGGDNHGRGRGRGRGRGG
GRPGAPGGSGSGPRHRDGVRRPQKRPSCIGCKGTHGGTGAGAGAGGAGAGG
AGAGGGAGAGGGAGGAGGAGGAGAGGGAGAGGGAGGAGGAGAGGGAGAGGG
AGGAGAGGGAGGAGGAGAGGGAGAGGGAGGAGAGGGAGGAGGAGAGGGAGA
GGAGGAGGAGAGGAGAGGGAGGAGGAGAGGAGAGGAGAGGAGAGGAGGAGA
GGAGGAGAGGAGGAGAGGGAGGAGAGGGAGGAGAGGAGGAGAGGAGGAGAG
GAGGAGAGGGAGAGGAGAGGGGRGRGGSGGRGRGGSGGRGRGGSGGRRGRG
RERARGGSRERARGRGRGRGEKRPRSPSSQSSSSGSPPRRPPPGRRPFFHP
VGEADYFEYHQEGGPDGEPDVPPGAIEQGPADDPGEGPSTGPRGQGDGGRR
KKGGWFGKHRGQGGSNPKFENIAEGLRALLARSHVERTTDEGTWVAGVFVY
GGSKTSLYNLRRGTALAIPQCRLTPLSRLPFGMAPGPGPQPGPLRESIVCY
FMVFLQTHIFAEVLKDAIKDLVMTKPAPTCNIRVTVCSFDDGVDLPPWFPP
MVEGAAAEGDDGDDGDEGGDGDEGEEGQE Length: 422
Type: PRT
Organism: Human herpesvirus 4
SEQ ID NO: 2
MSDEGPGTGPGNGLGEKGDTSGPEGSGGSGPQRRGGDNHGRGRGRGRGRGG
GRPGAPGGSGSGPRHRDGVRRPQKRPSCIGCKGTHGGTGAGAGAGGAGAGG
AGAGGGGRGRGGSGGRGRGGSGGRGRGGSGGRRGRGRERARGGSRERARGR
GRGRGEKRPRSPSSQSSSSGSPPRRPPPGRRPFFHPVGEADYFEYHQEGGP
DGEPDVPPGAIEQGPADDPGEGPSTGPRGQGDGGRRKKGGWFGKHRGQGGS
NPKFENIAEGLRALLARSHVERTTDEGTWVAGVFVYGGSKTSLYNLRRGTA
LAIPQCRLTPLSRLPFGMAPGPGPQPGPLRESIVCYFMVFLQTHIFAEVLK
DAIKDLVMTKPAPTCNIRVTVCSFDDGVDLPPWFPPMVEGAAAEGDDGDDG
DEGGDGDEGEEGQE

EXAMPLES

The following examples are offered by way of illustration and not by way of limitation.

Example 1—Material and Methods

Single Cell Dissociation

All reprogramming cultures were switched to FMM on day 14 post transfection. Once in FMM all reprogramming cultures were maintained and dissociated using Accutase. Single cells were then passaged on either Matrigel or Vitronectin coated surface. The single cell dissociated cells were then expanded in FMM and maintained until flow cytometry sorting.

Flow Cytometry Analysis and Sorting

Single cell dissociated reprogramming pools were resuspended in chilled staining buffer. Conjugated primary antibodies, including SSEA4-FITC, TRA181-Alexa Fluor-647 and CD30-PE (BD Biosciences), were added to the cell solution and incubated on ice for 15 min. All antibodies were used at 7-10 µL in 100 µL staining buffer per million cells. The resuspended dissociated single cells in staining buffer were spun down and resuspended in staining buffer now containing a ROCK inhibitor and maintained on ice for flow cytometry sorting. Flow cytometry sorting was performed on FACS Aria II (BD Biosciences) using gating strategy described in the Results section. The sorted cells were directly ejected into 96-well plates at concentrations of 3 and 9 events per well. Each well was prefilled with FMM. Upon completion of the sort, 96-well plates were incubated for colony formation and expansion. Seven to ten days post sort, the cells were passaged. Subsequent passages in FMM were done routinely upon 75-90% confluency. Flow cytometry analysis was performed on Guava EasyCyte 8 HT (Millipore) and analyzed using FCS Express 4 (De Novo Software).

Testing Presence of Transgenes

Genomic DNA was isolated using QIAamp® DNA Mini Kit and Proteinase K digestion (Qiagen). 100 ng of the genomic DNA was amplified using primer sets specific to transgenes including the reprogramming factors and EBNA1 using Taq PCR Master Mix Kit (Qiagen). The PCR reactions were run for 35 cycles as follows: 94° C. for 30 sec (denaturation), 60-64° C. for 30 sec (annealing) and 72° C. for 1 min (extension). Genomic DNA from fibroblasts and hiPSCs generated using lentiviral methods were used as negative controls. DNA of the episomal constructs was used as positive control.

Alkaline Phosphatase Staining

Cells were fixed in 4% v/v paraformaldehyde (Alfa Aesar), washed three times with PB S and stained with Alkaline Phosphatase Staining Kit (Millipore). Briefly, two parts Fast Red Violet, one part Naphtol AS-BI Phosphaste and one part water were mixed, added to the fixed cells and incubated at 25° C. for 15 min followed by a PBS wash.

Karyotype Analysis

Cytogenetic analysis was performed on G-banded metaphase cells by WiCell Research Institute (Madison, WI). Each karyotype analysis includes a minimum count of 20 spreads with analyses expanded to 40 spread counts when nonclonal aberrations are identified in the first 20.

Teratoma Formation

Single cell dissociated hiPSCs, at concentrations of 0.5 and 3 million cells per 200 µL solution (100 µL FMM and 100 µL Matrigel) were injected subcutaneously into NOD/SCID/γnull mice. After 5-6 weeks (3 million cells injection) and 7-8 weeks (0.5 million cells injection), teratomas were harvested, fixed, and maintained for processing. Samples were submitted to UCSD Histology Core Facility for sectioning, staining and examining.

Statistical Analysis

At least three independent experiments were performed. Values are reported as mean+SEM. Statistical analysis was done with ANOVA with p<0.05 considered significant.

Culture Media

Conventional hESC culture contains DMEM/F12 culture medium supplemented with 20% KnockOut serum replacement, 0.1 mM (or 1% v/v) non-essential amino acids, 1-2 mM L-glutamine, 0.1 mM B-mercaptoethanol and 10-100 ng/ml bFGF). In comparison, the multistage culture media additionally comprise a ROCK inhibitor, and one or more of GSK3 inhibitor, MEK inhibitor and TGFβ inhibitor. This stage-specific culture platform also supports feeder-free reprogramming and maintenance.

In certain applications, in addition to the ingredients for conventional culture, the reprogramming medium (FRM) contains SMC4: a combination of ROCK inhibitor, GSK3 inhibitor, MEK inhibitor and TGFβ inhibitor; and the maintenance medium (FMM) contains SMC3: a combination of ROCK inhibitor, GSK3 inhibitor, and MEK inhibitor.

Example 2—Reprogramming Using Transient and Temporal Reprogramming System

Both plasmid and episomal vectors are non-integrating extrachromosomal DNAs. A standard plasmid contains only a promoter and polynucleotide(s) to be expressed, and is not capable of replicating either autonomously or with the host cell chromosome. Therefore, the transgene expression mediated by a plasmid is not continuous nor stable but rather transient (cytoplasmic) and temporary (short term), and is dictated by the surviving input vector DNA which could be subject to transfection efficiency, copy number and the rate of plasmid loss. It has been shown that only by repeated daily transfections of plasmid vector was reprogramming achieved yet with unacceptably low efficiency (Okita et al., Science (2008); 322:949-953).

In comparison to a plasmid vector, episomal vector can exist and replicate either autonomously in the cytoplasm or as part of a chromosome. Therefore, transgene expression mediated by an episomal vector is continuous and stable due to the replication of the vectors. For example, in addition to the transgene(s) of interest, the EBV-based episomal vector encodes both the Epstein-Barr nuclear antigen-1 (EBNA1) protein and the origin of replication (oriP) derived from EBV, which act jointly to replicate and retain the episomal vector in the nucleus of dividing cells. The expressed EBNA in the episomal vector binds oriP and recruits cellular DNA replication complex component to allow oriP initiating the replication of the vector DNA along with the host cell chromosomal replication. EBNA-1 then tethers daughter episomes generated during S phase to host daughter chromosomes through oriP, maintaining nuclear retention of the episome, and thus continuous transgene(s) and EBNA expression (Gil et al., Gene Ther 2010 17(10): 1288-1293). The EBNA-mediated episome tethering confers segregation of the episomes to each daughter cell during mitosis, ensuring a constant number of episome per cell (Gil et al., 2010). An episomal plasmid containing both oriP and an EBNA-1 expression cassette can persist in replicating cultured human cells with ~95% episome retention per cell cycle without selection (Gil et al., 2010). The EBV-based episomal vectors provide a continuous expression of exogenous reprogramming factors for at least 12 days (a time period required to establish a self-sustaining pluripotent state, see Okita et al., Science (2008); 322:949-953; or at least 8 days to at least 30 days stated in U.S. Pat. No. 8,5546,140).

To carry out reprogramming using the transient and temporal reprogramming system of the present application, several vectors were constructed as shown in Table 1 and FIG. 1. Vector 1 (V1) is a plasmid vector containing a promoter driving expression of selected reprogramming factor(s) (RF) and an oriP. Vector 1 does not have EBNA encoding sequence, and has shortened retention time in a host cell as a result. Vector 1 is also termed as oriP/RF plasmid. In cases where Vector 1 encodes more than one reprogramming factor, the factors may be separated by a self-cleaving 2A peptide, or IRES. Multiple Vis may be used for co-transfection where different combinations of multiple reprogramming factors are desired, and stoichiometry of the reprogramming factors can be predetermined by controlling the relative copy number of each reprogramming factor in a combination of V1 s. Vector 2 (V2) is a plasmid containing a promoter and EBNA encoding sequence, which expression is driven by the promoter. More importantly, V2 lacks oriP which leads to significantly reduced V2 retention time in the transfected host cell population. Vector 2 is also called EBNA plasmid. V2 can also be replaced with EBNA mRNA or protein/peptide. The method and material for mRNA mediated reprogramming is described, for example, in Warren et al. (Cell Stem Cell (2010):7, 618-630); whereas for recombinant protein mediated reprogramming, it is described, for example, in Zhou et al. (Cell Stem Cell (2009):4, 381-384), both of which are incorporated herein by reference. Vector 3 (V3) is a vector expressing both oriP and EBNA, but does not have any reprogramming factor coding sequence. To examine whether these vectors support reprogramming, V1, V2 and V3 were transduced either alone or in different combinations to human fibroblasts (see Table 2).

TABLE 1

Vector Construction

| Vector | Vector Description | Notes |
|---|---|---|
| 1A | pCEP4-OCT4-P2A-OCT4-oriP | Does not contain EBNA; has shortened retention time in host cell as a plasmid; |
| 1B | pCEP4-NANOG-P2A-SOX2-T2A-SV40 LT-oriP | |
| 1C | pCEP4-CDH1-P2A-ZIC3-T2A-ESRG-oriP | |
| 1D | pCEP4-ECAT1-P2A-UTF1-oriP | |
| 1E | pCEP4-L1TD1-P2A-DPPA4-T2A-TDGF1-oriP | |
| 2 | pCDNA-EBNA-1 | Does not contain oriP; has shortened retention time in host cell |
| 3 | pCEP4-oriP-EBNA-1 | Contains both oriP and EBNA, significantly prolongs retention time in host cell; but does not express reprogramming factor transgene(s) |

Figure 2:
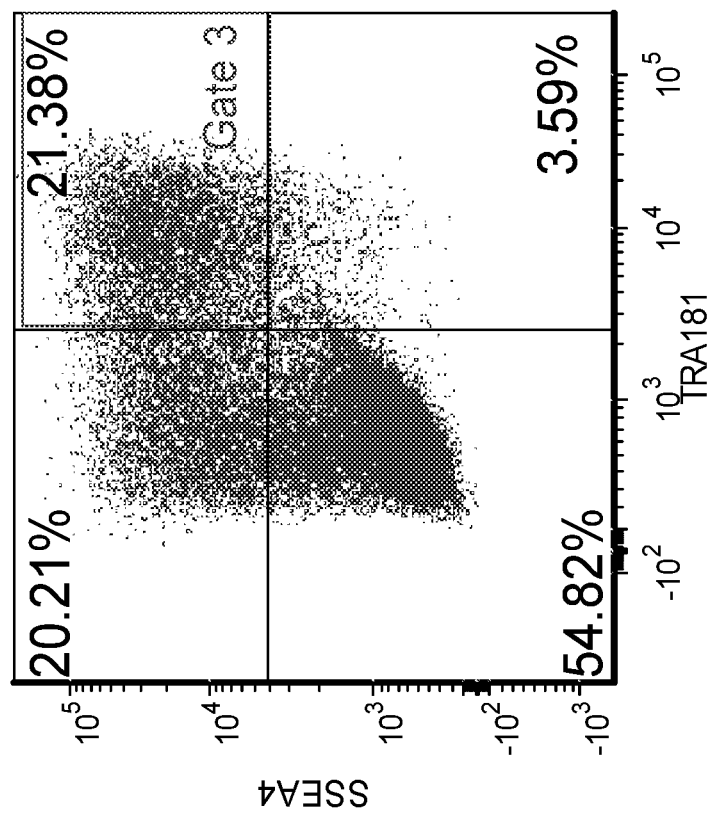
FIG. 2 shows flow cytometry analysis for SSEA4+/TRA181+ pluripotency marker expression 15 days post transfection of fibroblasts using an EmTTR system.
Figure 3:
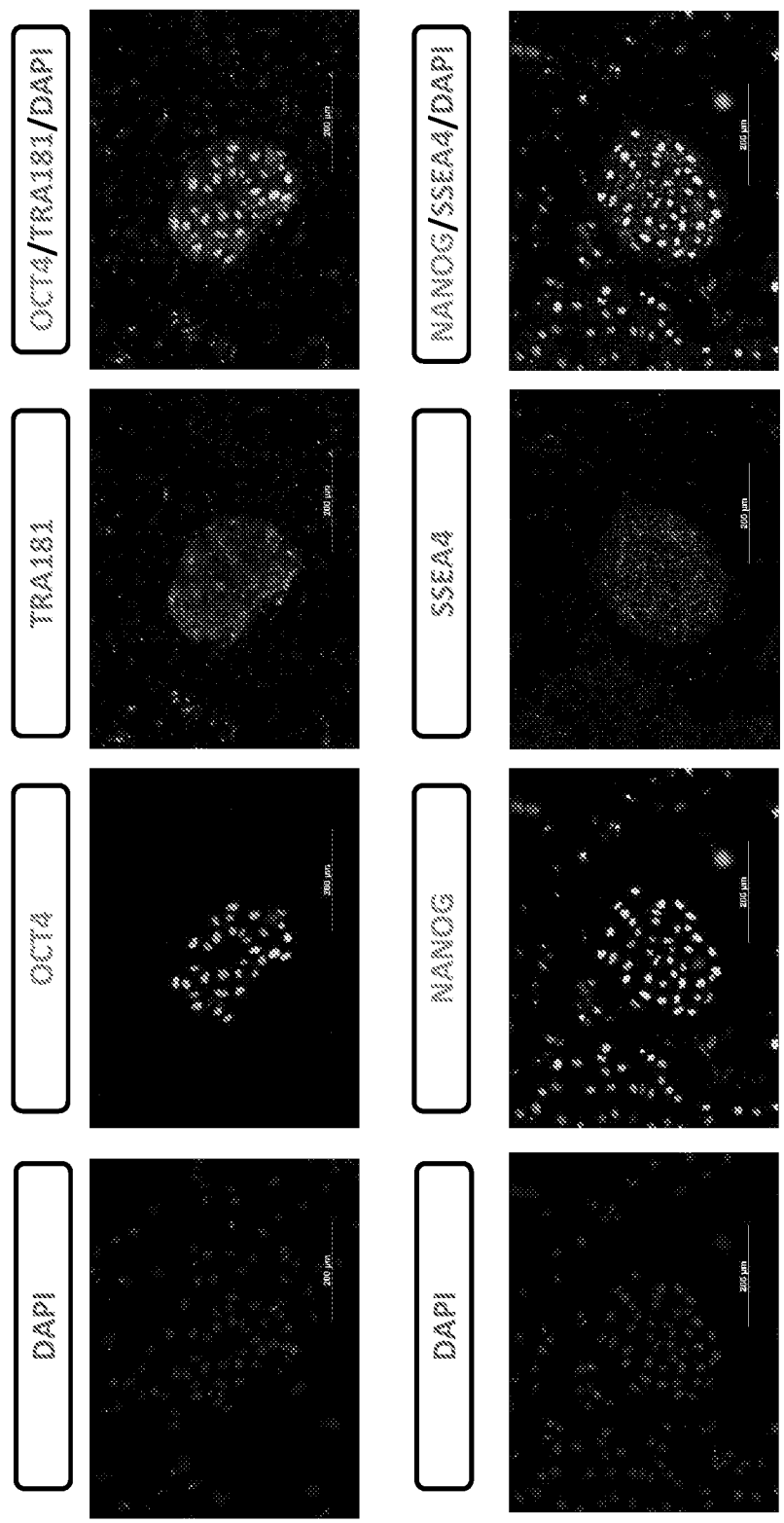
FIG. 3 shows pluripotency markers OCT4, NANOG TRA181, and SSEA4 staining 30 days post transfection to confirm the emergence of colonies expressing iPSC markers using an EmTTR system.

First tested was the combination of V1, V2 and V3 (EmTTR, EBNA-mediated Transient and Temporal Reprogramming system) to induce long-term expression of EBNA, persistent transgene retention and effective reprogramming. Reprogramming factors used in this combination included OCT4, NANOG and SOX2 (V1A and V1B). Fifteen days post transfection (D15), the reprogramming pool was sorted by flow cytometry for cells expressing both SSEA4 and TRA181, indicative of a pluripotency state. A remarkable 21.4% of the cells are double positive in these pluripotency markers (FIG. 2). Thirty days post transfection (D30), the reprogramming pool was stained for iPSC pluripotency markers TRA181, SSEA4 and CD30 (surrogate marker for NANOG) (FIG. 3). The immunofluorescent staining for OCT4 and NANOG confirms the emergence of colonies expressing iPSC pluripotency markers indicating successful reprogramming.

Figure 4:
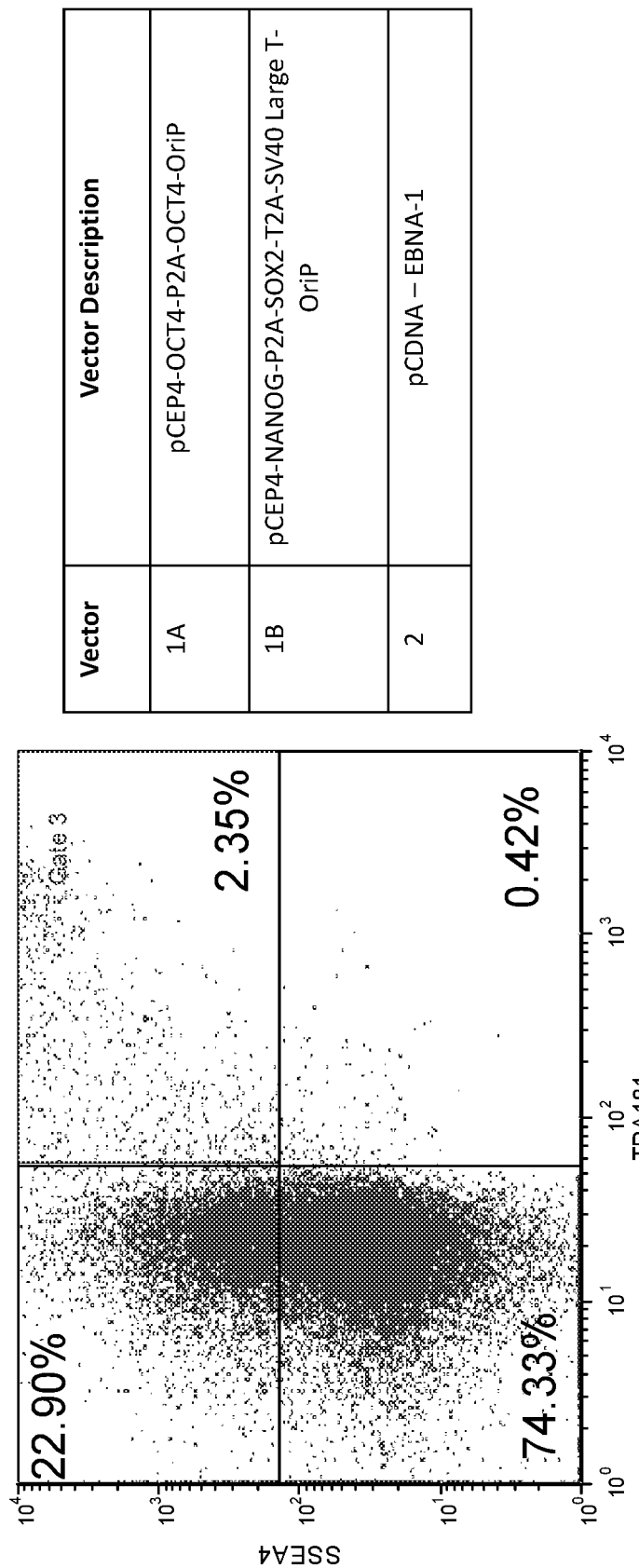
FIG. 4 shows flow cytometry analysis for SSEA4+/TRA181+ pluripotency marker expression 15 days post transfection of fibroblasts using an STTR system.
Figure 5:
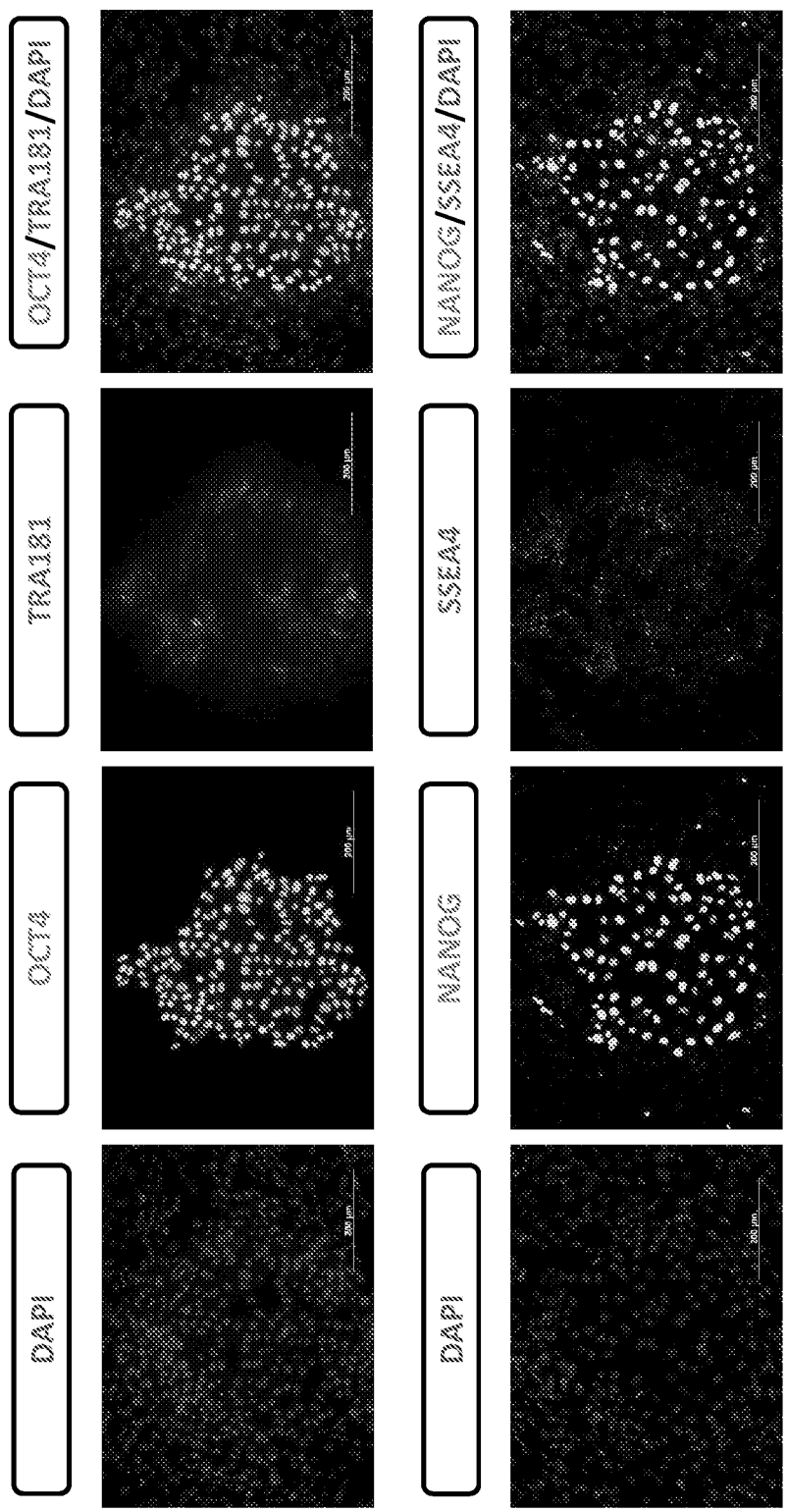
FIG. 5 shows pluripotency markers OCT4, NANOG TRA181, and SSEA4 staining 30 days post transfection to confirm the emergence of colonies expressing iPSC markers using a STTR system.

To eliminate the possibility that V3 creates in trans a super-physiological quantity of transgene expression in EmTTR system, creating cells that are overly dependent on transgene expression rather than timely transitioning to endogenous pluripotency factors in driving reprogramming, we removed V3 from the combination and transfected fibroblast with only V1 (V1A+V1B) and V2, a system termed as STTR (Short-lived Transient and Temporal Reprogramming). Surprisingly, V1 and V2 combination not only resulted in reprogramming, but also with a modest efficiency without the need of repeated transfection of V1 and V2. There were 2.35% SSEA/TRA181 double positive cells on D15 post transfection (FIG. 4). Twenty-seven days post transfection, the reprogramming pool was stained for iPSC pluripotency markers TRA181, SSEA4 and CD30. The immunofluorescent staining confirms the emergence of colonies expressing iPSC pluripotency markers indicating successful reprogramming using the STTR system (V1 and V2 only) (FIG. 5).

This was an entirely unexpected result. It was anticipated that the STTR system would not support reprogramming as the short-lived transgene expression was assumed to not be sufficient in either duration or timing.

TABLE 2

Vector Combinations for Reprogramming

| Vector(s) | D12-D15 SSEA4+/TRA181+ cells | Reprogrammed cells |
|---|---|---|
| V1A + V1B (V1 alone) | N/A | No |
| V2 alone | N/A | No |
| V3 alone | N/A | No |
| V1A + V1B + V2 + V3 (EmTTR) | 21.4% | Yes (pluripotency reverted) |
| V1A + V1B + V2 (STTR) | 2.35% | Yes (pluripotency maintained) |
| Episomal Vector (oriP/EBNA/OCT4.SOX2.-NANOG.LIN28.c-Myc.KLF4.-SV40LT)[1] | 0.0003-0.0006% AP staining[2] | Yes |

Figure 6:
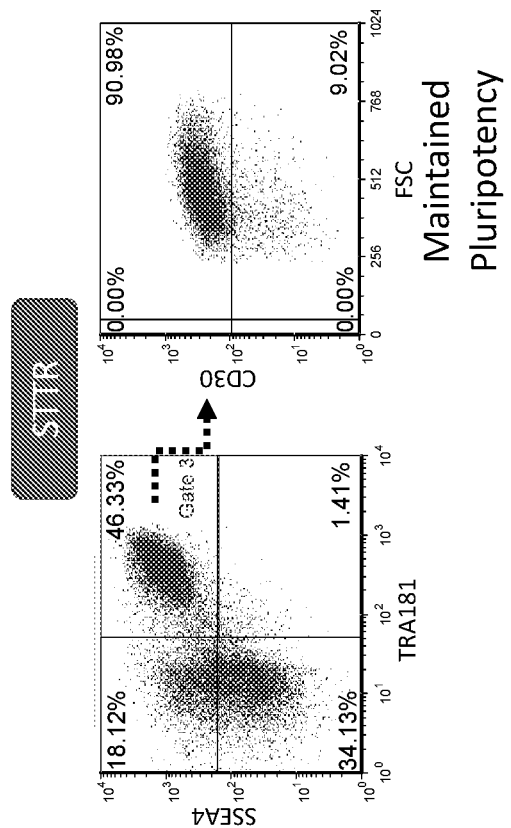
FIG. 6 shows that majority of the population derived from STTR have maintained expression of all three markers of pluripotency, whereas EmTTR induced population appears to be losing pluripotency as indicated by the major drop in CD30 expression 25 days post transfection.
Figure 6:
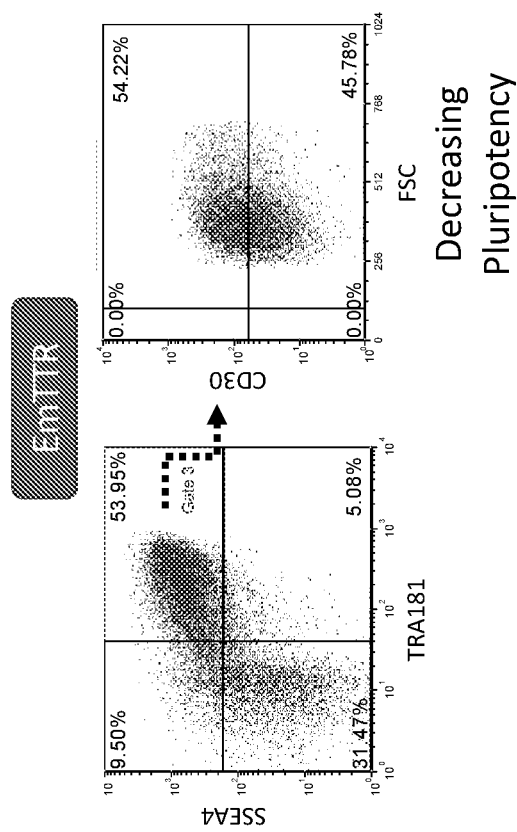
Figure 7:
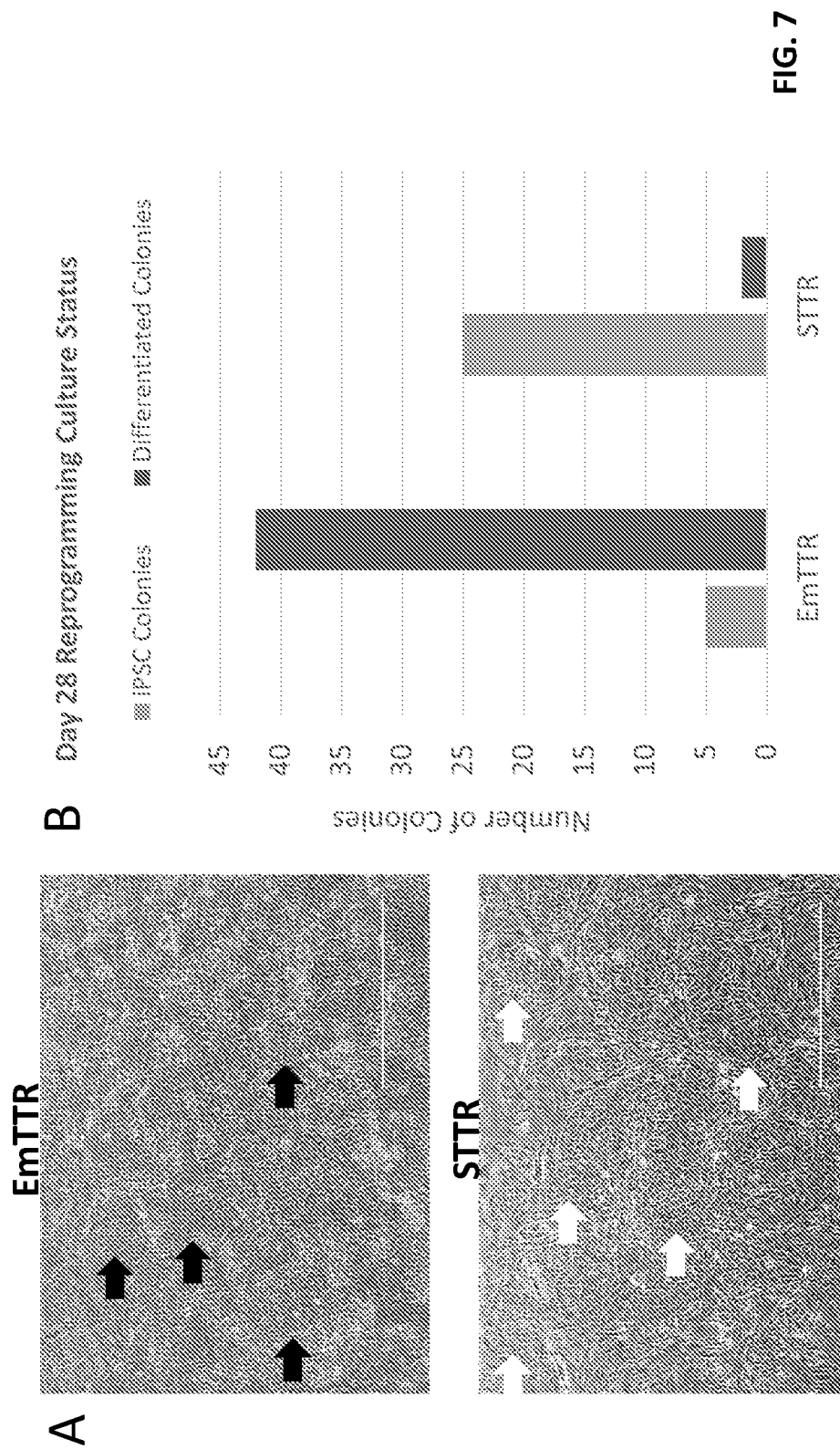
FIGS. 7A-7B show that the stability of the pluripotency is different in the iPSC colonies obtained from EmTTR and STTR after serial passaging on D28. A: Morphology of iPSC colonies and differentiated clusters in the culture in both populations. B: The STTR population maintained iPSC colonies with minimum spontaneous differentiation, while EmTTR population showed a high level of spontaneous differentiation with the presence of only few iPSC colonies.

[1]Yu et al., Science (2009); 324(5928): 797-801 (co-transfection of 3 episomal vectors to transfer 7 reprogramming factors and reprogrammed using feeder conditioned conventional hESC medium to obtain 3-6 colonies/$10^6$ input cells).
[2]AP staining is less stringent than double positive in estimating reprogramming efficiency In addition, although initial reprogramming by the EmTTR system appears much more efficient in comparison to the STTR reprogramming based on the percentage of double positive cells, STTR however better supports cellular reprogramming towards generating iPSCs having self-sustaining pluripotency and capable of being maintained for long term. Fibroblast cells induced to reprogram using EmTTR and STTR systems were respectively maintained for 25 days and assessed for expression of pluripotent markers SSEA4, TRA181 and CD30. As shown in FIG. 6, while majority of the population derived from STTR at D25 have maintained expression of all three markers of pluripotency, EmTTR induced population at D25 appears to be losing pluripotency as indicated by the major drop in CD30 expression, indicating reversion associated with a non-sustainable or unstable pluripotent state. Both populations were then passaged and the morphology of iPSC colonies and differentiated clusters in the culture was subsequently observed and compared on D28 (FIG. 7A). As initially noted with maintained coexpression of SSEA4, TRA181 and CD30, the STTR population maintained mainly as iPSC colonies with minimum spontaneous differentiation, while EmTTR population showed a high level of spontaneous differentiation (FIG. 7B).

Figure 8:
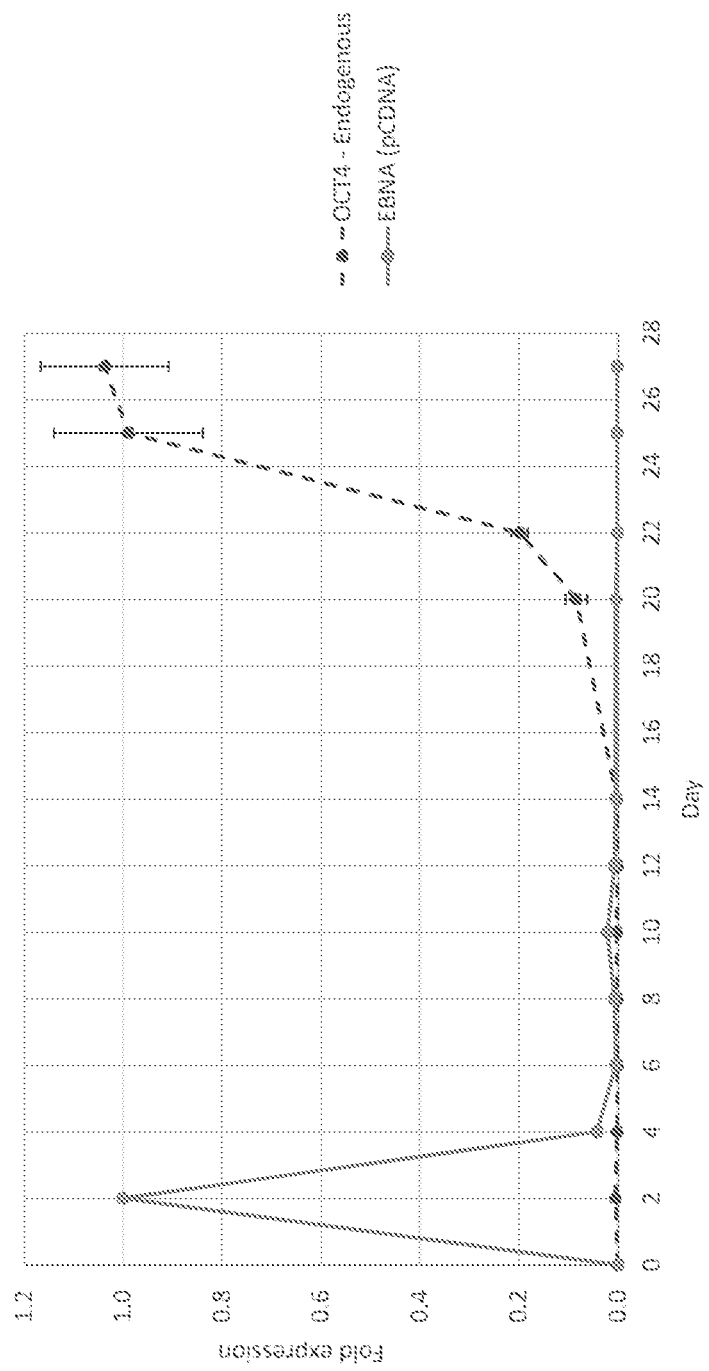
FIG. 8 shows the gene expression analysis of EBNA carried in vector 2 and endogenous OCT4 expression in the cell population during cellular reprogramming of fibroblasts using a STTR system.

To analyze the transient and temporal nature of STTR system, we analyzed the EBNA expression in the cell population post transfection using quantitative RT-PCR. Also monitored was the endogenous OCT4 expression indicative of the emergence of the pluripotency state in the cell population. As shown in FIG. 8, EBNA expression appeared after transfection, reached the highest point on D2, and then started dropping sharply to less than 1% by D4, reflecting a loss rate of the V2 plasmid more than 90% per cell division (compared to about 5% loss rate of EBV-based episomal vectors). The conventional assays eliminate selection for plasmids at the beginning of the experiment and screen for the appearance of plasmid-free cells over long-term population growth. By D6, the EBNA expression in the population is essentially non-detectable, characterizing a transitory expression system. Such a rapid loss of EBNA expression determined its extreme short-lived and temporal nature, indicating most likely a transient retention of the V2 plasmid in cytoplasm without the benefit of nucleus up-take and chromosomal tethering or genome integration. More importantly, the EBNA was lost before any iPSC morphology appeared in the culture and surely before self-sustaining pluripotent state was formed. The method provided herein reduced the EBNA-mediated plasmid retention time, and is in a clear contrast to the need for stable EBNA expression in episomal mediated reprogramming (c.f. U.S. Pat. No. 8,546, 140, requiring stable EBNA expression for at least 8 days to at least 30 days, or constitutive expression in the hosting cell in Mazda et al., 1997).

Howden et al., 2006 (Human Gene Therapy; 17:833-844) showed that co-transfecting EBNA mRNA with EBV based episomal vector increases the nuclear uptake and thus the chromosomal tethering of the EBV-based episomal vector, and thus increased the transfection efficiency by 10 fold. In the present application, the transient spike of EBNA expression by V2 plasmid transfection in the STTR system may be similar in form to that of EBNA mRNA, however, V1 plasmid herein, containing oriP alone and without expressing EBNA, lacks the tethering mechanism of an EBV-based episomal that relies on a continuous EBNA expression to retain and replicate the vector DNA long-term to meaningfully impact the transfection rate. Even if the transporting of an oriP containing plasmid such as V1 from cytoplasm to nucleus is increased by the transiently expressed EBNA plasmid V2 upon the instance of co-transfection of the two plasmids, V1 still does not support a long-term expression of reprogramming factor transgenes as indicated by a similar rate of loss between V1 and V2.

Therefore, the STTR reprogramming using V1 and V2 is through a mechanism of plasmids that is featured as truly transient (extrachromosomal and cytoplasmic) and temporal (extreme short in duration), different from an episomal reprogramming that is nucleus located and long-term in comparison. Without the need of multiple transfection, V1 and V2 mediated plasmid reprogramming is surprisingly efficient. Moreover, the plasmid reprogramming appeared to lose all EBNA plasmid by D6, at which time point no iPSC, or a pluripotency state, has been formed. Via EBNA detection, the STTR system demonstrated that the transgene loss is rapid and is significantly before establishing pluripotency state which is generally around D21-D32, with the heightened endogenous OCT4 expression level as one of the markers.

Figure 9:
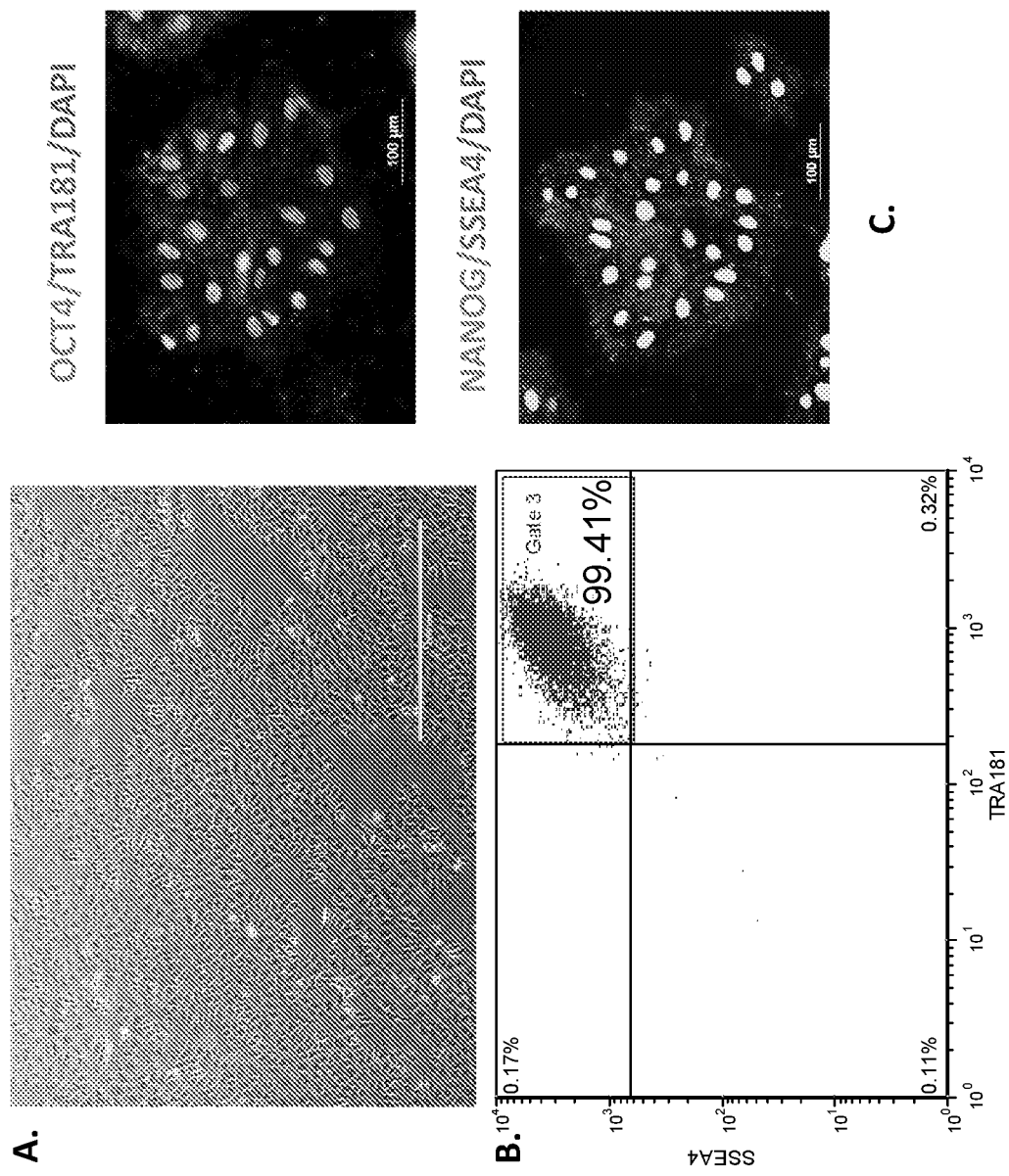
FIGS. 9A-9D show the characterization of iPSCs obtained using STTR for pluripotency expression and demonstration of teratoma formation in mice. A. A phase image of the iPSC clones. B. Flow analysis of SSEA4+/TRA181+ pluripotency marker expression. C. Immunofluorescent staining of the clone for pluripotency markers OCT4, NANOG TRA181, and SSEA4. D. The iPSC clone's ability to differentiate into the three germ layers: endoderm, mesoderm, and ectoderm.

Interestingly, although the reprogramming efficiency using STTR system was lower than EmTTR system (approximately 2% versus 21%), unlike the EmTTR system we did not detect pluripotency reversion and/or spontaneous differentiation of iPSCs in the STTR system as majority of the generated iPSCs in the STTR system maintained their iPSC status and were able to differentiate into all three germ layers: the endoderm, mesoderm and ectoderm (FIG. 9). This in part may be attributable to the short duration of transgene exposure to the cell population such that the reprogramming is more leaning towards utilizing induced endogenous developmental system and kinetics, rather than vastly being driven by exogenous reprogramming factors whose presence may be sustained by long-term expression of EBNA as seen in EmTTR.

To provide further evidence for the absence of V1 DNA in the newly formed iPSCs, we conducted a functional test in multiple iPSC lines (D25-D30) for survival in the presence of hygromycin. All tested hiPSC lines demonstrated to be clear of any genetic components of STTR and showed to be resistant to hygromycin, further evidence of complete loss of V1 DNA in the STTR system. Selected clones were continuously passaged as single cells in a feeder free environment and were demonstrated to maintain a homogeneous population of undifferentiated cells, while displaying the ability to efficiently differentiate into the three somatic lineages. Karyotype and copy number variation analysis revealed genomically stable hiPSC lines during long-term culture maintained in FMM. In addition, the selected clones demonstrated the ability to give rise to cells of the three germ layers and when directed, differentiated in a homogenous manner towards hematopoietic cells including CD34+ cells, NK cells and T cells.

Figure 10:
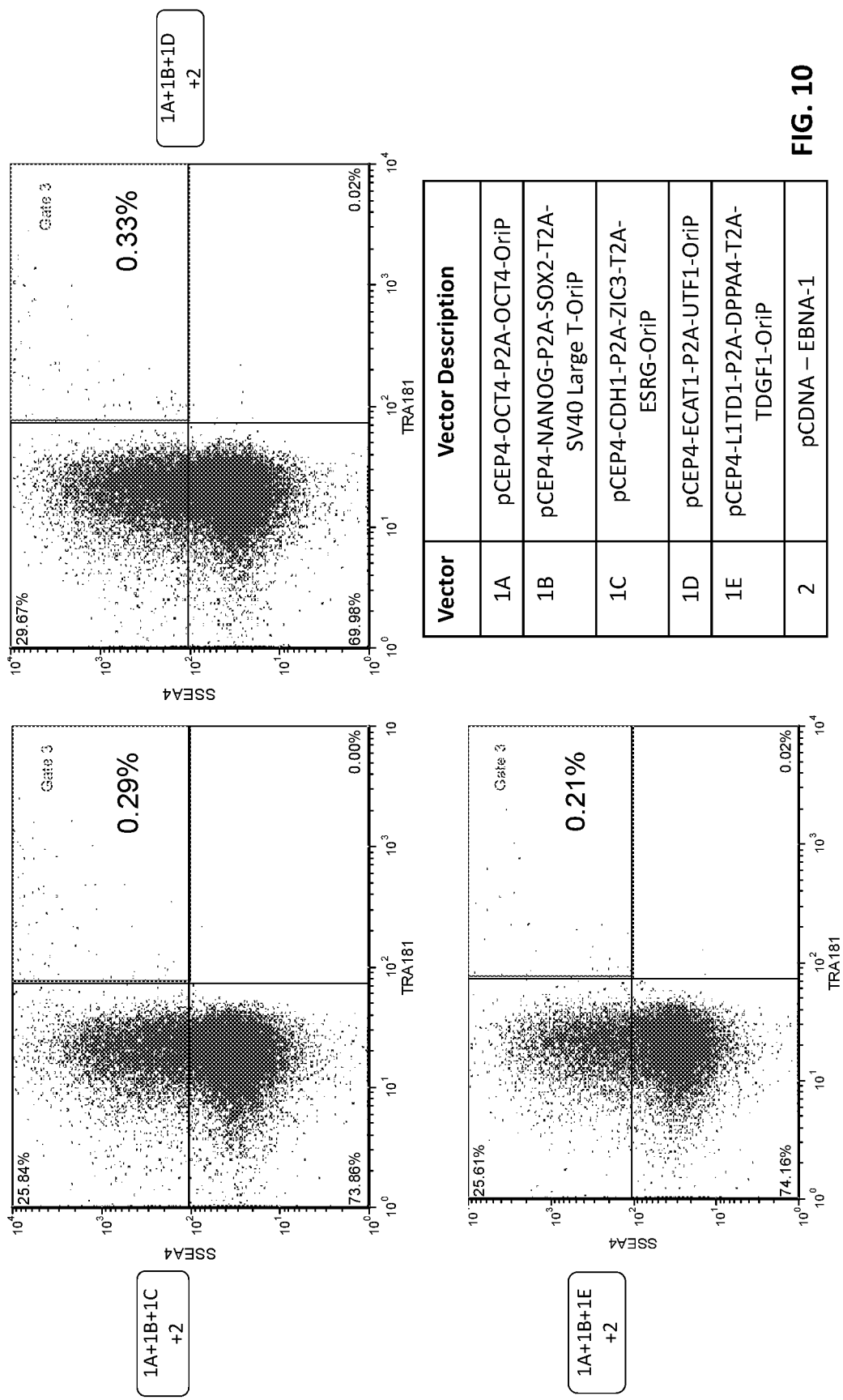
FIG. 10 shows flow cytometry analysis for SSEA4+/TRA181+ pluripotency marker expression 15 days post transfection of fibroblasts using a STTR system with additional reprogramming factors.

The STTR system was also shown to be effective in initiating reprogramming irrespective of the various reprogramming factor combinations carried by distinct V1 vectors (FIG. 10 and Table 3).

TABLE 3

Novel Reprogramming Factor Combinations Applicable for STTR System-Mediated Reprogramming

| Vector(s) | D12-D15 SSEA4+/TRA181+ cells | Reprogrammed cells |
| --- | --- | --- |
| V1A + V1B + V1C + V2 | 0.29% | Yes |
| V1A + V1B + V1D + V2 | 0.33% | Yes |
| V1A + V1B + V1E + V2 | 0.21% | Yes |

Reprogramming using the present STTR system and reprogramming using the EBV-based episomal vector generate different iPSCs in terms of exogenous DNA content. EBV-based episomal reprogramming was lauded for generating foot-print free iPSCs, but is largely dependent on a slow rate of episomal DNA loss at about 3-5% per cell division (Leight et al., Mol Cell Biol (2001); 21:4149-4161). Therefore, when an episomal vector is used for reprogramming, a footprint-free iPSC population is possible only after many rounds of iPS cell passaging. It has been shown to take at least 12-15 passages (each culture splitting every 4-7 days counts as one passage) of the initially obtained iPSCs to obtain a pluripotent stem cell population that is essentially footprint-free (Cheng et al., Cell Stem Cell (2012); 10:337-344) without selection. Until then, the iPSC population so generated is highly heterogenous in terms of their exogenous DNA content. One study showed that about two thirds of the iPSCs in the population contain the oriP/EBNA episomal vector at about 20 day post transfection (Leight et al., Mol Cell Biol (2001); 21:4149-4161; Yu et al., Science (2009); 324(5928): 797-801). For reprogrammed cells having noticeable or high spontaneous differentiation rate, obtaining footprint-free iPSCs through prolonged natural passaging process is even more inadequate.

Collectively, the data show that footprint-free hiPSCs can be readily generated by transiently and temporarily expressing reprogramming genes using the short-lived plasmid vector combinations provided herein, and the platform supports efficient and expedited generation of a substantially homogenous foot-print free iPSC population. In some embodiments, the foot-print free iPSC population is generated without the need for extensive passaging, and optionally, in a completely feeder-free environment.

Example 3—Transient and Temporal Reprogramming System for Generating Single Cell-Derived iPSC Bank as a Source of Derivative Cells for Therapeutic Uses The STTR reprogramming compositions and methods have been used to generate clonal master iPSC lines for use as renewable and reliable cell sources for off-the-shelf immunotherapies. Donor-consented fibroblasts were transfected with the plasmid combination as disclosed. Reprogramming cells were sorted at clonal density into 96-well plates, and single cell-derived iPSC clones were expanded and screened for desired attributes including pluripotency, loss of reprogramming plasmids, genomic stability and differentiation potential. Selected clonal iPSC line was manufactured and cryopreserved under strict manufacturing and process quality controls, and the line was further subject to extensive characterization and testing in order to qualify as "master cell bank" as required under relevant regulation. Manufactured iPSC banks were differentiated following current good manufacturing practices into natural killer (NK) cells to a clinically relevant scale. The derivative cells were further subject to extensive characterization and testing in order to qualify as "drug substance and drug product" as required under relevant regulation. The iPSC-derived NK cells were cryopreserved to generate a large number of doses at about $1 \times 10^8$ cells/dose for use in adoptive cell therapy for blood and solid cancers as monotherapy or in combination with immune checkpoint inhibitors. Generally, $1 \times 10^8$ cells/dose translates to $1.67 \times 10^6$ cells/kg for a 60 kg patient. The dosage form, route of administration and dosing regimen for each indication were designed and determined according to preclinical data from GLP (Good Laboratory Practice) and non-GLP studies both in vitro and in vivo.

Beyond supporting iPSC-derived immune cells to treat cancer and immune diseases, footprint-free and feeder cell-free master iPSC lines generated by the STTR reprogramming platform has the potential to enable off-the-shelf cell therapies for degenerative disorders, ranging from macular degeneration, diabetes, Parkinson's disease, blood disorders, to cardiovascular diseases.

One skilled in the art would readily appreciate that the methods, compositions, and products described herein are representative of exemplary embodiments, and not intended as limitations on the scope of the invention. It will be readily apparent to one skilled in the art that varying substitutions and modifications may be made to the present disclosure disclosed herein without departing from the scope and spirit of the invention.

All patents and publications mentioned in the specification are indicative of the levels of those skilled in the art to which the present disclosure pertains. All patents and publications are herein incorporated by reference to the same extent as if each individual publication was specifically and individually indicated as incorporated by reference.

The present disclosure illustratively described herein suitably may be practiced in the absence of any element or elements, limitation or limitations that are not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the present disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method of reprogramming non-pluripotent cells to generate pluripotent cells, a cell line or a population thereof, comprising:
   (a) introducing to first cells, wherein the first cells are non-pluripotent cells:
   one or more first plasmids, wherein each of the one or more first plasmids comprises a replication origin comprising an Epstein-Barr nuclear antigen (EBNA) binding site, and a polynucleotide encoding one or more reprogramming factors but does not encode an EBNA; wherein the one or more first plasmids comprises polynucleotides encoding reprogramming factor(s) comprising any combination of OCT4, SOX2, NANOG, KLF, LIN28, c-MYC, ECAT1, UTF1, ESRRB, HESRG, CDH1, TDGF1, DPPA4, DNMT3B, ZIC3, and L1TD1; wherein introduction of the one or more first plasmids induces a reprogramming process; and
   a second plasmid comprising a nucleotide sequence encoding an EBNA, wherein the second plasmid does not comprise a replication origin comprising an EBNA binding site or polynucleotide(s) encoding reprogramming factor(s);
   (b) culturing the cells from step (a) to generate second cells, wherein the second cells are reprogramming cells, wherein the reprogramming cells comprise a morphological change from the first cells and are essentially free of EBNA; and wherein the reprogramming cells do not comprise:
      (1) pluripotent cell morphology; and
      (2) endogenous OCT4 expression; and,
   (c) further culturing the second cells obtained in step (b) for a sufficient amount of time to generate pluripotent cells;
   wherein the method does not comprise introducing a third plasmid that comprises both of (1) a replication origin comprising an EBNA binding site, and (2) a polynucleotide encoding an EBNA; and
   wherein the pluripotent cells exhibit a reduced rate of spontaneous differentiation as compared to reprogramming non-pluripotent cells with the one or more first plasmids, the second plasmid, and the third plasmid.

2. The method of claim 1, further comprising:
dissociating the pluripotent cells to obtain single cell dissociated pluripotent cells.

3. The method of claim 2, further comprising:
suspending the single cell dissociated pluripotent cells.

4. The method of claim 2, further comprising:
sorting the single cell dissociated pluripotent cells by selecting and isolating the cells expressing one or more pluripotency markers to enrich for pluripotent cells expressing the marker(s).

5. The method of claim 1, further comprising:
culturing the pluripotent cells in the presence of a GSK3 inhibitor, a MEK inhibitor and a ROCK inhibitor to maintain pluripotency, wherein the pluripotent cells maintain pluripotency for at least 5, 10, 15, or 20 passages.

6. The method of claim 1, wherein culturing in step (b) comprises culturing in the presence of at least one of a TGFβ inhibitor, a GSK3 inhibitor, a MEK inhibitor and a ROCK inhibitor.

7. The method of claim 1, wherein the first cells are somatic cells, progenitor cells, or multipotent cells.

8. The method of claim 1, wherein the first cells are fibroblasts, and wherein the morphological change of the second cells comprises MET (mesenchymal to epithelial transition).

9. The method of claim 1, wherein the second cells are essentially free of plasmids of step (a).

10. The method of claim 1, wherein the second cells comprise reprogramming cells of about 4 to 10, 12, 14, 21, 25 days, or to any number of days in-between post the introduction of one or more first plasmids in step (a).

11. The method of claim 1, wherein the pluripotent cells are essentially free of the polynucleotides of the plasmids of step (a) without the need for selection.

12. The method of claim 1, wherein the pluripotent cells have at least one of the properties:
(1) genetic stability; and
(2) ground state pluripotency.

13. The method of claim 1, wherein the pluripotent cells comprise reactivated genes associated with extraembryonic cells.

14. The method of claim 1, wherein the second plasmid has a high rate of loss; and/or wherein the expression of EBNA is transient and temporal.

15. The method of claim 1, wherein the replication origin and/or EBNA is EBV-based.

16. The method of claim 1, wherein the first cell and second cell are under a feeder-free condition.

17. The method of claim 5, wherein the ROCK inhibitor is thiazovivin.

18. A population of non-pluripotent cells comprising:
(a) one or more first plasmids, wherein each of the one or more first plasmids comprises a replication origin comprising an EBNA binding site, and a polynucleotide encoding one or more reprogramming factors, but does not encode an EBNA; wherein the one or more first plasmids comprises polynucleotides encoding reprogramming factor(s) comprising any combination of OCT4, SOX2, NANOG, KLF, LIN28, c-MYC, ECAT1, UTF1, ESRRB, HESRG, CDH1, TDGF1, DPPA4, DNMT3B, ZIC3, and L1TD1; and
(b) a second plasmid comprising a nucleotide sequence encoding an EBNA, wherein the second plasmid does not comprise a replication origin comprising an EBNA binding site or polynucleotide(s) encoding reprogramming factor(s);
wherein the non-pluripotent cells do not comprise:
(1) pluripotent cell morphology; and
(2) endogenous OCT4 expression; and
wherein the non-pluripotent cells are capable of establishing stable or self-sustaining pluripotency given a sufficient amount of time to generate pluripotent cells;
wherein the non-pluripotent cells do not comprise a third plasmid that comprises both of (1) a replication origin comprising an EBNA binding site, and (2) a polynucleotide encoding an EBNA; and
wherein pluripotent cells generated from the non-pluripotent cells exhibit a reduced rate of spontaneous differentiation as compared to pluripotent cells generated by reprogramming non-pluripotent cells with the one or more first plasmid, the second plasmid, and the third plasmid.

19. The population of non-pluripotent cells of claim 18, wherein the non-pluripotent cells undergo a morphological change comprising MET (mesenchymal to epithelial transition) upon culturing.

20. The population of non-pluripotent cells of claim 18, wherein the pluripotent cells are essentially free of the polynucleotides of the one or more first plasmids and the second plasmid without the need for selection.

21. The population of non-pluripotent cells of claim 18, wherein the pluripotent cells have at least one of the properties:
(1) genetic stability; and
(2) ground state pluripotency.

22. The population of non-pluripotent cells of claim 18, wherein the pluripotent cells comprise reactivated genes associated with extraembryonic cells.

23. The population of non-pluripotent cells of claim 18, wherein the non-pluripotent cell is a fibroblast.

24. A composition comprising the population of non-pluripotent cells of claim 18.

25. The composition of claim 24, further comprising a medium comprising at least one of a TGFβ inhibitor, a GSK3 inhibitor, a MEK inhibitor and a ROCK inhibitor.

26. The composition of claim 25, wherein the ROCK inhibitor is thiazovivin.

27. The composition of claim 25, wherein the medium is feeder-free.

28. An isolated pluripotent cell or a pluripotent cell line produced by a method according to claim 1.

29. A genomically engineered pluripotent cell or a cell line thereof produced using an isolated pluripotent cell or cell line produced by a method according to claim 1.

30. A derived non-natural cell re-differentiated from the isolated pluripotent cell or cell line of claim 28 or from a genomically engineered pluripotent cell or cell line produced using the isolated pluripotent cell or cell line.

31. The derived non-natural cell of claim 30, wherein the cell comprises a CD34 cell, a hemogenic endothelium cell, a hematopoietic stem or progenitor cell, a hematopoietic multipotent progenitor cell, a T cell progenitor, an NK cell progenitor, a T cell, a NKT cell, an NK cell, a B cell, or an immune regulatory cell.

32. The derived non-natural cell of claim 30, wherein the cell is a rejuvenated cell comprising at least one of the following properties: global increase of heterochromatin; improved mitochondrial function; increased DNA damage responses; telomere elongation and decrease of percentage of short telomere; decrease in the fraction of senescent cells; and higher potential for proliferation, survival, persistence, or memory like functions, in comparison to its natural cell counterpart.

33. A composition for therapeutic use comprising a pluripotent cell obtained by a method according to claim 1, and optionally one or more additional therapeutic agents.

34. A composition for therapeutic use comprising a genomically engineered pluripotent cell of claim 29 or a derived non-natural cell differentiated therefrom, and optionally one or more additional therapeutic agents.

35. The composition of claim 33 for use in treating a subject in need thereof.

36. A composition for use in manufacturing a pluripotent cell for application in cell-based therapies, wherein the composition comprises a pluripotent cell produced by a method according to claim 1.

37. The composition of claim 36, wherein the pluripotent cell is allogeneic or autologous.

38. A kit for medicament use comprising a pluripotent cell obtained by a method according to claim 1.

39. A kit for medicament use comprising a genomically engineered pluripotent cell of claim 29 or a derived non-natural cell differentiated therefrom.

* * * * *

SEQUENCE LISTING

```
<160> NUMBER OF SEQ ID NOS: 2

<210> SEQ ID NO 1
<211> LENGTH: 641
<212> TYPE: PRT
<213> ORGANISM: Homo sapiense
<220> FEATURE:
<223> OTHER INFORMATION: Human herpesvirus 4

<400> SEQUENCE: 1

Met Ser Asp Glu Gly Pro Gly Thr Gly Pro Gly Asn Gly Leu Gly Glu
1               5                   10                  15

Lys Gly Asp Thr Ser Gly Pro Glu Gly Ser Gly Gly Ser Gly Pro Gln
            20                  25                  30

Arg Arg Gly Gly Asp Asn His Gly Arg Gly Arg Gly Arg Gly Arg Gly
        35                  40                  45

Arg Gly Gly Gly Arg Pro Gly Ala Pro Gly Gly Ser Gly Ser Gly Pro
    50                  55                  60

Arg His Arg Asp Gly Val Arg Arg Pro Gln Lys Arg Pro Ser Cys Ile
65                  70                  75                  80

Gly Cys Lys Gly Thr His Gly Gly Thr Gly Ala Gly Ala Gly Ala Gly
                85                  90                  95

Gly Ala Gly Ala Gly Gly Ala Gly Ala Gly Gly Gly Ala Gly Ala Gly
            100                 105                 110

Gly Gly Ala Gly Gly Ala Gly Gly Ala Gly Gly Ala Gly Ala Gly Gly
        115                 120                 125
```

Gly Ala Gly Ala Gly Gly Ala Gly Ala Gly Ala Gly Ala
    130             135             140

Gly Gly Gly Ala Gly Ala Gly Gly Ala Gly Ala Gly Ala Gly
145             150             155                 160

Gly Gly Ala Gly Ala Gly Gly Ala Gly Ala Gly Gly Ala Gly
            165             170             175

Ala Gly Gly Gly Ala Gly Gly Ala Gly Ala Gly Gly Ala Gly
        180             185             190

Ala Gly Gly Ala Gly Ala Gly Gly Ala Gly Ala Gly Ala Gly
        195             200             205

Gly Ala Gly Gly Ala Gly Ala Gly Gly Ala Gly Ala Gly Gly Ala
    210             215             220

Gly Gly Ala Gly Gly Ala Gly Ala Gly Gly Ala Gly Ala Gly Ala
225             230             235             240

Gly Ala Gly Gly Ala Gly Ala Gly Gly Ala Gly Ala Gly Ala Gly
            245             250             255

Gly Ala Gly Gly Ala Gly Ala Gly Gly Ala Gly Ala Gly Ala Gly
            260             265             270

Gly Gly Ala Gly Gly Ala Gly Ala Gly Gly Ala Gly Gly Ala Gly
    275             280             285

Ala Gly Gly Ala Gly Gly Ala Gly Ala Gly Gly Ala Gly Ala Gly
    290             295             300

Ala Gly Gly Ala Gly Ala Gly Ala Gly Gly Ala Gly Ala Gly Ala Gly
305             310             315             320

Gly Ala Gly Ala Gly Gly Gly Arg Gly Arg Gly Gly Ser Gly Gly
            325             330             335

Arg Gly Arg Gly Gly Ser Gly Gly Arg Gly Arg Gly Gly Ser Gly Gly
            340             345             350

Arg Arg Gly Arg Gly Arg Glu Arg Ala Arg Gly Gly Ser Arg Glu Arg
        355             360             365

Ala Arg Gly Arg Gly Arg Gly Arg Gly Glu Lys Arg Pro Arg Ser Pro
        370             375             380

Ser Ser Gln Ser Ser Ser Ser Gly Ser Pro Pro Arg Pro Pro Pro
385             390             395             400

Gly Arg Arg Pro Phe Phe His Pro Val Gly Glu Ala Asp Tyr Phe Glu
            405             410             415

Tyr His Gln Glu Gly Gly Pro Asp Gly Glu Pro Asp Val Pro Pro Gly
            420             425             430

Ala Ile Glu Gln Gly Pro Ala Asp Asp Pro Gly Glu Gly Pro Ser Thr
            435             440             445

Gly Pro Arg Gly Gln Gly Asp Gly Gly Arg Arg Lys Lys Gly Gly Trp
        450             455             460

Phe Gly Lys His Arg Gly Gln Gly Gly Ser Asn Pro Lys Phe Glu Asn
465             470             475             480

Ile Ala Glu Gly Leu Arg Ala Leu Leu Ala Arg Ser His Val Glu Arg
            485             490             495

Thr Thr Asp Glu Gly Thr Trp Val Ala Gly Val Phe Val Tyr Gly Gly
            500             505             510

Ser Lys Thr Ser Leu Tyr Asn Leu Arg Arg Gly Thr Ala Leu Ala Ile
            515             520             525

Pro Gln Cys Arg Leu Thr Pro Leu Ser Arg Leu Pro Phe Gly Met Ala
        530             535             540

Pro Gly Pro Gly Pro Gln Pro Gly Pro Leu Arg Glu Ser Ile Val Cys

```
                  545                 550                 555                 560

Tyr Phe Met Val Phe Leu Gln Thr His Ile Phe Ala Glu Val Leu Lys
                565                 570                 575

Asp Ala Ile Lys Asp Leu Val Met Thr Lys Pro Ala Pro Thr Cys Asn
                580                 585                 590

Ile Arg Val Thr Val Cys Ser Phe Asp Asp Gly Val Asp Leu Pro Pro
                595                 600                 605

Trp Phe Pro Pro Met Val Glu Gly Ala Ala Glu Gly Asp Asp Gly
    610                 615                 620

Asp Asp Gly Asp Glu Gly Gly Asp Gly Asp Glu Gly Glu Gly Gln
625                 630                 635                 640

Glu

<210> SEQ ID NO 2
<211> LENGTH: 422
<212> TYPE: PRT
<213> ORGANISM: Homo sapiense
<220> FEATURE:
<223> OTHER INFORMATION: Human herpesvirus 4

<400> SEQUENCE: 2

Met Ser Asp Glu Gly Pro Gly Thr Gly Pro Gly Asn Gly Leu Gly Glu
1               5                   10                  15

Lys Gly Asp Thr Ser Gly Pro Glu Gly Ser Gly Ser Gly Pro Gln
                20                  25                  30

Arg Arg Gly Gly Asp Asn His Gly Arg Gly Arg Gly Arg Gly Arg Gly
            35                  40                  45

Arg Gly Gly Arg Pro Gly Ala Pro Gly Gly Ser Gly Ser Gly Pro
    50                  55                  60

Arg His Arg Asp Gly Val Arg Arg Pro Gln Lys Arg Pro Ser Cys Ile
65                  70                  75                  80

Gly Cys Lys Gly Thr His Gly Gly Thr Gly Ala Gly Ala Gly Ala Gly
                85                  90                  95

Gly Ala Gly Ala Gly Gly Ala Gly Ala Gly Gly Gly Arg Gly Arg
            100                 105                 110

Gly Gly Ser Gly Gly Arg Gly Arg Gly Gly Ser Gly Gly Arg Gly Arg
        115                 120                 125

Gly Gly Ser Gly Gly Arg Arg Gly Arg Gly Arg Glu Arg Ala Arg Gly
    130                 135                 140

Gly Ser Arg Glu Arg Ala Arg Gly Arg Gly Arg Gly Arg Gly Glu Lys
145                 150                 155                 160

Arg Pro Arg Ser Pro Ser Ser Gln Ser Ser Ser Ser Gly Ser Pro Pro
                165                 170                 175

Arg Arg Pro Pro Pro Gly Arg Arg Pro Phe Phe His Pro Val Gly Glu
            180                 185                 190

Ala Asp Tyr Phe Glu Tyr His Gln Glu Gly Gly Pro Asp Gly Glu Pro
        195                 200                 205

Asp Val Pro Pro Gly Ala Ile Glu Gln Gly Pro Ala Asp Asp Pro Gly
    210                 215                 220

Glu Gly Pro Ser Thr Gly Pro Arg Gly Gln Gly Asp Gly Gly Arg Arg
225                 230                 235                 240

Lys Lys Gly Gly Trp Phe Gly Lys His Arg Gly Gln Gly Gly Ser Asn
                245                 250                 255

Pro Lys Phe Glu Asn Ile Ala Glu Gly Leu Arg Ala Leu Leu Ala Arg
            260                 265                 270
```

```
Ser His Val Glu Arg Thr Thr Asp Glu Gly Thr Trp Val Ala Gly Val
        275                 280                 285

Phe Val Tyr Gly Gly Ser Lys Thr Ser Leu Tyr Asn Leu Arg Arg Gly
    290                 295                 300

Thr Ala Leu Ala Ile Pro Gln Cys Arg Leu Thr Pro Leu Ser Arg Leu
305                 310                 315                 320

Pro Phe Gly Met Ala Pro Gly Pro Gly Pro Gln Pro Gly Pro Leu Arg
                325                 330                 335

Glu Ser Ile Val Cys Tyr Phe Met Val Phe Leu Gln Thr His Ile Phe
            340                 345                 350

Ala Glu Val Leu Lys Asp Ala Ile Lys Asp Leu Val Met Thr Lys Pro
            355                 360                 365

Ala Pro Thr Cys Asn Ile Arg Val Thr Val Cys Ser Phe Asp Asp Gly
    370                 375                 380

Val Asp Leu Pro Pro Trp Phe Pro Pro Met Val Glu Gly Ala Ala Ala
385                 390                 395                 400

Glu Gly Asp Asp Gly Asp Asp Gly Asp Glu Gly Gly Asp Gly Asp Glu
                405                 410                 415

Gly Glu Glu Gly Gln Glu
                420
```